US012570687B2

(12) United States Patent
Zhang et al.

(10) Patent No.: US 12,570,687 B2
(45) Date of Patent: Mar. 10, 2026

(54) TRITERPENOID COMPOUNDS, PHARMACEUTICAL COMPOSITIONS THEREOF, AND THEIR USE FOR TREATING A NUCLEAR RECEPTOR SUBFAMILY 4 GROUP A MEMBER 1-MEDIATED DISEASE

(71) Applicant: NUCMITO PHARMACEUTICALS COMPANY LIMITED, Fujian (CN)

(72) Inventors: Xiaokun Zhang, Xiamen (CN); Ying Su, Xiamen (CN); Guobin Xie, Xiamen (CN); Zhenfei Huang, Xiamen (CN); Ziwen Chen, Xiamen (CN); Yuqi Zhou, Xiamen (CN); Duo Zhang, Xiamen (CN); Zhiping Zeng, Xiamen (CN); Siwei Yan, Xiamen (CN)

(73) Assignee: NucMito Pharmaceuticals Co. Ltd., Xiamen (CN)

( * ) Notice: Subject to any disclaimer, the term of this patent is extended or adjusted under 35 U.S.C. 154(b) by 1010 days.

(21) Appl. No.: 17/753,684

(22) PCT Filed: Sep. 14, 2020

(86) PCT No.: PCT/CN2020/115070
§ 371 (c)(1),
(2) Date: Mar. 11, 2022

(87) PCT Pub. No.: WO2021/047672
PCT Pub. Date: Mar. 18, 2021

(65) Prior Publication Data
US 2022/0324903 A1    Oct. 13, 2022

Related U.S. Application Data

(60) Provisional application No. 62/899,671, filed on Sep. 12, 2019.

(51) Int. Cl.
*C07J 63/00* (2006.01)
*A61K 9/00* (2006.01)
(Continued)

(52) U.S. Cl.
CPC ........... *C07J 63/008* (2013.01); *A61K 9/0019* (2013.01); *A61K 9/16* (2013.01); *A61P 35/00* (2018.01); *C07J 71/0057* (2013.01)

(58) Field of Classification Search
None
See application file for complete search history.

(56) References Cited

FOREIGN PATENT DOCUMENTS

| | | |
|---|---|---|
| CN | 101805390 A | 8/2010 |
| WO | 2018006801 A1 | 1/2018 |
| WO | 2018006804 A1 | 1/2018 |

OTHER PUBLICATIONS

Gonzalez ("Structure and Absolute Configuration of Triterpene Dimers from Maytenus scutioides." Tetrahedron, 1996, p. 9597 (Year: 1996).*

(Continued)

*Primary Examiner* — Amy C Bonaparte
(74) *Attorney, Agent, or Firm* — Lin Yu; Juniv LLP

(57) ABSTRACT

Disclosed herein are triterpenoid compounds, for example, a compound of Formula (I), and pharmaceutical compositions thereof. Also disclosed herein are methods of their use for treat.

(Continued)

(I)

26 Claims, 1 Drawing Sheet

(51) Int. Cl.

| | |
|---|---|
| *A61K 9/16* | (2006.01) |
| *A61P 35/00* | (2006.01) |
| *C07J 71/00* | (2006.01) |

(56) References Cited

OTHER PUBLICATIONS

Shirota ("New Geometric and Stereoisomeric Triterpene Dimers from Maytenus chuchuhuasca" Chem. Pharm. Bull, 46, 1998, p. 102). (Year: 1998).*

Reyes ("Oxidation of Natural Targets by Dimethyl Dioxirane: Regio and Stereospecific Reactions on Enol Double Bond of Bioactive Nor Quinone Methide Triterpenes." Tetrahedron, 1996, p. 10667) (Year: 1996).*

FDA (Q3C—Tables and List Guidance for Industry, published Aug. 2018, downloaded from https://www.fda.gov/media/133650/ download on May 5, 2025) (Year: 2018).*

Berge et al., "Pharmaceutical salts," J. Pharm. Sci. 1977, 66, 1-19.

Chen et al., "SAR study of celastrol analogs targeting Nur77-mediated inflammatory pathway," Eur. J. Med. Chem. 2019, 177, 171-87.

Cho et al., "Nur77 agonists induce proapoptotic genes and responses in colon cancer cells through nuclear receptor-dependent and nuclear receptor-independent pathways," Cancer Res. 2007, 67, 674-83.

Lee et al., "The nuclear receptor TR3 regulates mTORC1 signaling in lung cancer cells expressing wild-type p53," Oncogene 2012, 31, 3265-76.

Pearen and Muscat, "Minireview: Nuclear hormone receptor 4A signaling: implications for metabolic disease," Mol. Endocrinol. 2010, 24, 1891-903.

Safe et al., "Minireview: role of orphan nuclear receptors in cancer and potential as drug targets," Mol. Endocrinol. 2014, 28, 157-72.

Wang et al., "Orphan nuclear receptor Nur77 promotes colorectal cancer invasion and metastasis by regulating MMP-9 and E-cadherin," Carcinogenesis 2014, 35, 2474-84.

Wu and Chen, "Characteristics of Nur77 and its ligands as potential anticancer compounds (Review)," Mol. Med. Rep. 2018, 18, 4793-801.

Zhang, "Targeting Nur77 translocation," Expert Opin. Ther. Targets 2007, 11, 69-79.

Zheng et al., "Orphan nuclear receptor TR3/Nur77 is a specific therapeutic target for hepatic cancers," J. Clin. Exp. Oncol. 2017, 6, 184.

Zhou et al., "Nuclear receptor NR4A1 promotes breast cancer invasion and metastasis by activating TGF-β signalling," Nat. Commun. 2014, 5, 3388.

* cited by examiner

1

TRITERPENOID COMPOUNDS, PHARMACEUTICAL COMPOSITIONS THEREOF, AND THEIR USE FOR TREATING A NUCLEAR RECEPTOR SUBFAMILY 4 GROUP A MEMBER 1-MEDIATED DISEASE

CROSS REFERENCE TO RELATED APPLICATION

This application is a National Stage of International Application No. PCT/CN2020/115070, filed Sep. 14, 2020; which claims the benefit of U.S. Provisional Application No. 62/899,671, filed Sep. 12, 2019; the disclosure of each of which is incorporated herein by reference in its entirety.

FIELD

Provided herein are triterpenoid compounds and pharmaceutical compositions thereof. Also provided herein are methods of their use for treating, ameliorating, or preventing a disorder, disease, or condition mediated by nuclear receptor subfamily 4 group A member 1.

BACKGROUND

Nuclear receptor subfamily 4 group A member 1 (NR4A1), also known as Nur77, NGFIB, and TR3, is an orphan member of the nuclear receptor superfamily. Zhang, *Expert Opin. Ther. Targets* 2007, 11, 69-79. Nur77 plays vital roles in cell proliferation, differentiation, apoptosis, development, metabolism, inflammation, and immunity. Id.; Wu and Chen, *Mol. Med.* Rep. 2018, 18, 4793-4801; Safe et al., *Mol. Endocrinol.* 2014, 28, 157-172; and Pearen and Muscat, *Mol. Endocrinol.* 2010, 24, 1891-1903. For example, it has been shown that Nur77 is abnormally overexpressed in a wide range of cancer types, such as breast, colon, hepatic, lung, prostate, and pancreatic cancer. Zheng et al., *J. Clin. Exp. Oncol.* 2017, 6, pii: 184; Safe et al., *Mol. Endocrinol.* 2014, 28, 157-172; Wang et al., *Carcinogenesis* 2014, 35, 2474-2484; Zhou et al., *Nat. Commun.* 2014, 5, 3388; Lee et al., *Oncogene* 2012, 31, 3265-3276; Cho et al., *Cancer Res.* 2007, 67, 674-683. Functional studies show that silencing Nur77 in breast, cervical, colon, gastric, lung, lymphoma, melanoma, ovarian, and pancreatic cancer cell lines decreases cell growth, survival, migration, and/or invasion. Safe et al., *Mol. Endocrinol.* 2014, 28, 157-172.

Therefore, there is a need for a compound as an effective therapy for treating a disorder, disease, or condition mediated by nuclear receptor subfamily 4 group A member 1, for example, a proliferative disease.

SUMMARY OF THE DISCLOSURE

Provided herein is a compound of Formula (I):

(I)

2 or a diastereomer, a mixture of two or more diastereomers, a tautomer, a mixture of two or more tautomers, or an isotopic variant thereof; or a pharmaceutically acceptable salt, solvate, hydrate, or prodrug thereof;

wherein:

$R^1$ is (i) hydrogen, deuterium, azido, cyano, halo, isocyanato, isothiocyanato, or nitro; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C($R^{1a}$) =N$R^{1b}$, —C($R^{1a}$)=NO$R^{1b}$, —C(O)$R^{1a}$, —C(O) O$R^{1a}$, —C(O)ONR$^{1b}$R$^{1c}$, —C(O)OP(OR$^{1a}$)(OR$^{1b}$), —C(O)N(CN)$R^{1b}$, —C(O)NR$^{1b}$R$^{1c}$, —C(O)N(R$^{1b}$) OR$^{1c}$, —C(O)SR$^{1a}$, —C(=NR$^{1a}$)NR$^{1b}$R$^{1c}$, —C(S) $R^{1a}$, —C(S)OR$^{1a}$, —C(S)NR$^{1b}$R$^{1c}$, —OR$^{1a}$, —OC(O) $R^{1a}$, —OC(O)OR$^{1a}$, —OC(O)NR$^{1b}$R$^{1c}$, —OC(O) SR$^{1a}$, —OC(=NR$^{1a}$)NR$^{1b}$R$^{1c}$, —OC(S)R$^{1a}$, —OC(S) OR$^{1a}$, —OC(S)NR$^{1b}$R$^{1c}$, —OP(O)(OR$^{1a}$)OR$^{1d}$, —OS (O)$R^{1a}$, —OS(O)$_2$R$^{1a}$, —OS(O)$_2$OR$^{1a}$, —OS(O) NR$^{1b}$R$^{1c}$, —OS(O)$_2$NR$^{1b}$R$^{1c}$, —NR$^{1b}$R$^{1c}$, —NR$^{1a}$C (O)$R^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O) $R^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —SC(O)R$^{1a}$, —SC (O)NR$^{1b}$R$^{1c}$, —S(O)R$^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$;

$R^2$ is heteroaryl, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$) NR$^{1b}$R$^{1c}$, —OC(S)R$^{1a}$, —OC(S)OR$^{1a}$, —OC(S) NR$^{1b}$R$^{1c}$, —OP(O)(OR$^{1a}$)OR$^{1d}$, —OS(O)R$^{1a}$, —OS (O)$_2$R$^{1a}$, —OS(O)$_2$OR$^{1a}$, —OS(O)NR$^{1b}$R$^{1c}$, or —OS (O)$_2$NR$^{1b}$R$^{1c}$; or $R^2$ and $R^3$ together with the carbon atoms to which they are attached form heterocyclylene;

$R^3$ is $C_{1-6}$ alkyl, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$) NR$^{1b}$R$^{1c}$, —OC(S)R$^{1a}$, —OC(S)OR$^{1a}$, —OC(S) NR$^{1b}$R$^{1c}$, —OP(O)(OR$^{1a}$)OR$^{1d}$, —OS(O)R$^{1a}$, —OS (O)$_2$R$^{1a}$, —OS(O)$_2$OR$^{1a}$, —OS(O)NR$^{1b}$R$^{1c}$, —OS (O)$_2$ NR$^{1b}$R$^{1c}$, —NR$^{1b}$R$^{1c}$, —NR$^{1a}$C(O)R$^{1d}$, —NR$^{1a}$C (O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S) NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, or —NR$^{1a}$S(O)$_2$NR$^{1b}$R$^{1c}$; and $R^4$ is hydrogen or $R^3$; or $R^3$ and $R^4$ together with the carbon atom to which they are attached form heterocyclylene, =CR$^{1a}$R$^{1c}$, =CR$^{1a}$CN, =CO, =NR$^{1b}$, =NOR$^{1b}$, =NNR$^{1a}$C(O)R$^{1d}$, or =NNR$^{1a}$C(O) NR$^{1b}$R$^{1c}$; or $R^3$, $R^4$, and $R^5$ together with the carbon atoms to which they are attached form unsaturated heterocyclylene; or $R^3$, $R^5$, and $R^6$ together with the carbon atoms to which they are attached form unsaturated heterocyclylene;

$R^5$ is $C_{1-6}$ alkyl, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$) NR$^{1b}$R$^{1c}$, —OC(S)R$^{1a}$, —OC(S)OR$^{1a}$, —OC(S) NR$^{1b}$R$^{1c}$, —OP(O)(OR$^{1a}$)OR$^{1d}$, —OS(O)R$^{1a}$, —OS (O)$_2$R$^{1a}$, —OS(O)$_2$OR$^{1a}$, —OS(O)NR$^{1b}$R$^{1c}$, —OS (O)$_2$ NR$^{1b}$R$^{1c}$, —NR$^{1b}$R$^{1c}$, —NR$^{1a}$C(O)R$^{1d}$, —NR$^{1a}$C (O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S) NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, or —NR$^{1a}$S(O)$_2$NR$^{1b}$R$^{1c}$; and $R^6$ is hydrogen or $R^5$; or $R^5$ and $R^6$ together with the carbon atom to which they are attached form hetero-cyclylene, $=CR^{1a}R^{1c}$, $=CR^{1a}CN$, $=CO$, $=NR^{1b}$, or $=NOR^{1b}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, heterocyclyl, and heterocyclylene is optionally substituted with one or more, in one embodiment, one, two, three, or four, substituents Q, where each Q is independently selected from (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally sub-stituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OPO$_3$R$^a$R$^d$, —OS(O)R$^a$, —OS(O)$_2$R$^a$, —OSO$_3$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from: (a) deuterium, azido, cyano, halo, isocyanato, isothiocya-nato, and nitro; (b) $C_{1-6}$ alkyl, $C_{2-6}$ alkenyl, $C_{2-6}$ alky-nyl, $C_{3-10}$ cycloalkyl, $C_{6-14}$ aryl, $C_{7-15}$ aralkyl, het-eroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)R$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

Also provided herein is a compound of Formula (I):

(I)

or a diastereomer, a mixture of two or more diastereomers, a tautomer, a mixture of two or more tautomers, or an isotopic variant thereof; or a pharmaceutically acceptable salt, solvate, hydrate, or prodrug thereof;

wherein:

$R^1$ is (i) hydrogen, deuterium, azido, cyano, halo, isocya-nato, isothiocyanato, or nitro; (ii) $C_{1-6}$ alkyl, $C_{2-6}$ alk-enyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(R$^{1a}$)=NR$^{1b}$, —C(R$^{1a}$)=NOR$^{1b}$, —C(O)R$^{1a}$, —C(O)OR$^{1a}$, —C(O)ONR$^{1b}$R$^{1c}$, —C(O)OP(OR$^{1a}$)(OR$^{1b}$), —C(O)N(CN)R$^{1b}$, —C(O)NR$^{1b}$R$^{1c}$, —C(O)N(R$^{1b}$)OR$^{1c}$, —C(O)SR$^{1a}$, —C(=NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)R$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$;

$R^2$ is heteroaryl, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, or —OS(O)$_2$NR$^{1b}$R$^{1c}$;

$R^3$ is $C_{1-6}$ alkyl, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, —OS(O)$_2$ NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, or —NR$^{1a}$S(O)$_2$NR$^{1b}$R$^{1c}$; and $R^4$ is hydrogen or $R^3$; or $R^3$ and $R^4$ together with the carbon atom to which they are attached form hetero-cyclylene, $=CR^{1a}R^{1c}$, $=CR^{1a}CN$, $=CO$, $=NR^{1b}$, or $=NOR^{1b}$;

$R^5$ is $C_{1-6}$ alkyl, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS $(O)_2R^{1a}$, $-OS(O)_2R^{1a}$, $-OS(O)NR^{1b}R^{1c}$, $-OS$ $(O)_2 NR^{1b}R^{1c}$, $-NR^{1b}R^{1c}$, $-NR^{1a}C(O)R^{1d}$, $-NR^{1a}C$ $(O)OR^{1d}$, $-NR^{1a}C(O)SR^{1d}$, $-NR^{1a}C(O)NR^{1b}R^{1c}$, $-NR^{1a}C(=NR^{1d})R^{1b}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)$ $NR^{1b}R^{1c}$, $-NR^{1a}S(O)R^{1d}$, $-NR^{1a}S(O)_2R^{1d}$, $-NR^{1a}S(O)NR^{1b}R^{1c}$, or $-NR^{1a}S(O)_2NR^{1b}R^{1c}$; and $R^6$ is hydrogen or $R^5$; or $R^5$ and $R^6$ together with the carbon atom to which they are attached form heterocyclylene, $=CR^{1a}R^{1c}$, $=CR^{1a}CN$, $=CO$, $=NR^{1b}$, or $=NOR^{1b}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, heterocyclyl, and heterocyclylene is optionally substituted with one or more, in one embodiment, one, two, three, or four, substituents Q, where each Q is independently selected from (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) $-C(O)R^a$, $-C(O)OR^a$, $-C(O)NR^{1b}R^{1c}$, $-C(O)SR^a$, $-C(NR^a)$ $NR^bR^c$, $-C(S)R^a$, $-C(S)OR^a$, $-C(S)NR^bR^c$, $-OR^a$, $-OC(O)R^a$, $-OC(O)OR^a$, $-OC(O)NR^bR^c$, $-OC$ $(O)SR^a$, $-OC(=NR^a)NR^bR^c$, $-OC(S)R^a$, $-OC(S)$ $OR^a$, $-OC(S)NR^bR^c$, $-OPO_3R^aR^d$, $-OS(O)R^a$, $-OS(O)_2R^a$, $-OSO_3R^a$, $-OS(O)NR^bR^c$, $-OS(O)_2$ $NR^bR^c$, $-NR^bR^c$, $-NR^aC(O)R^d$, $-NR^aC(O)OR^d$, $-NR^aC(O)NR^bR^c$, $-NR^aC(O)SR^d$, $-NR^aC(=NR^d)$ $NR^bR^c$, $-NR^aC(S)R^d$, $-NR^aC(S)OR^d$, $-NR^aC(S)$ $NR^bR^c$, $-NR^aS(O)R^d$, $-NR^aS(O)_2R^d$, $-NR^aS(O)$ $NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $-C(O)R^e$, $-C(O)$ $OR^e$, $-C(O)NR^fR^g$, $-C(O)SR^e$, $-C(NR^e)NR^fR^g$, $-C(S)R^e$, $-C(S)OR^e$, $-C(S)NR^fR^g$, $-OR^e$, $-OC$ $(O)R^e$, $-OC(O)OR^e$, $-OC(O)NR^fR^g$, $-OC(O)SR^e$, $-OC(=NR^e)NR^fR^g$, $-OC(S)R^e$, $-OC(S)OR^e$, $-OC(S)NR^fR^g$, $-OS(O)R^e$, $-OS(O)_2R^e$, $-OS(O)$ $NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(O)SR^f$, $-NR^eC(=NR^h)R^fR^g$, $-NR^eC(S)R^h$, $-NR^eC(S)OR^f$, $-NR^eC(S)NR^fR^g$, $-NR^eS(O)R^h$, $-NR^eS(O)_2R^h$, $-NR^eS(O)NR^fR^g$, $-NR^eS(O)_2NR^fR^g$, $-SR^e$, $-S(O)$ $R^e$, $-S(O)_2R^e$, $-S(O)NR^fR^g$, and $-S(O)_2NR^fR^g$;

wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Additionally provided herein is a pharmaceutical composition, comprising a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, and a pharmaceutically acceptable excipient.

Furthermore, provided herein is a method of treating, ameliorating, or preventing a disorder, disease, or condition mediated by nuclear receptor subfamily 4 group A member 1 in a subject, which comprises administering to the subject a compound of Formula (I), or a diastereomer, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of treating, ameliorating, or preventing a proliferative disease in a subject, which comprises administering to the subject a compound of Formula (I), or a diastereomer, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of inducing apoptosis in a cell, comprising contacting the cell with a compound of Formula (I), or a diastereomer, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of modulating the activity of nuclear receptor subfamily 4 group A member 1 in a cell, comprising contacting the cell with a compound of Formula (I), or a diastereomer, a mixture of two or more diastereomers, a tautomer, a mixture of two or more tautomers, or an isotopic variant thereof, or a pharmaceutically acceptable salt, solvate, hydrate, or prodrug thereof.

DETAILED DESCRIPTION

Figure 1:
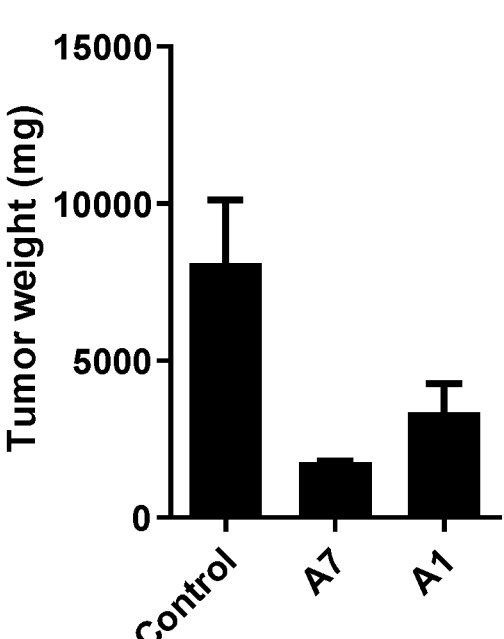
FIG. 1 shows the antiproliferative activity of compounds A1 and A7 in an MMTV-PyMT transgenic mouse model of spontaneous breast tumors.

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject"

and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, e.g., *Remington: The Science and Practice of Pharmacy,* 22nd ed.; Allen Ed.: Philadelphia, PA, 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH₃) and propargyl (—CH₂C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10

($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1] hexyl, bicyclo[2.2.1]heptyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 14 ($C_{6-14}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 15 ($C_{7-15}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclylene has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, the heterocyclylene is optionally substituted with one or more substituents Q as described herein.

The term "halogen", "halide," or "halo" refers to fluorine, chlorine, bromine, and/or iodine.

The symbol " $\equiv\equiv\equiv$ " represents a bond that can be a single bond or a double bond.

The term "optionally substituted" is intended to mean that a group or substituent, such as an alkyl, alkenyl, alkynyl, cycloalkyl, aryl, aralkyl, heteroaryl, heterocyclyl, or heterocyclylene group, may be substituted with one or more, one, two, three, or four, substituents Q, each of which is independently selected from, e.g., (a) deuterium (-D), azido ($-N_3$), cyano (—CN), halo, isocyanato (—NCO), isothiocyanato (—NCS), and nitro ($-NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OPO$_3$R$^a$R$^d$, —OS(O)R$^a$, —OS(O)$_2$R$^a$, —OSO$_3$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from: (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$ R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1$H), deuterium ($^2$H or D), and tritium ($^3$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single diastereomer or a mixture of diastereomers, as determined by a standard analytical method. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

For a divalent group described herein, no orientation is implied by the direction in which the divalent group is presented. For example, unless a particular orientation is specified, the formula —C(O)NH— represents both —C(O)NH— and —NHC(O)—.

The phrase "a diastereomer, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) a diastereomer, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of a diastereomer, a mixture of two or more diastereomers, a tautomer, a mixture of two or more tautomers, or an isotopic variant of the compound referenced therein."

Compounds

In one embodiment, provided herein is a compound of Formula (I):

(I)

or a diastereomer, a mixture of two or more diastereomers, a tautomer, a mixture of two or more tautomers, or an isotopic variant thereof; or a pharmaceutically acceptable salt, solvate, hydrate, or prodrug thereof;

wherein:

$R^1$ is (i) hydrogen, deuterium, azido, cyano, halo, isocyanato, isothiocyanato, or nitro; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C($R^{1a}$)=$NR^{1b}$, —C($R^{1a}$)=$NOR^{1b}$, —C(O)$R^{1a}$, —C(O)$OR^{1a}$, —C(O)$ONR^{1b}R^{1c}$, —C(O)OP($OR^{1a}$)($OR^{1b}$), —C(O)N(CN)$R^{1b}$, —C(O)$NR^{1b}R^{1c}$, —C(O)N($R^{1b}$)$OR^{1c}$, —C(O)$SR^{1a}$, —C(=$NR^{1a}$)$NR^{1b}R^{1c}$, —C(S)$R^{1a}$, —C(S)$OR^{1a}$, —C(S)$NR^{1b}R^{1c}$, —$OR^{1a}$, —OC(O)$R^{1a}$, —OC(O)$OR^{1a}$, —OC(O)$NR^{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OP(O)($OR^{1a}$)$OR^{1d}$, —OS(O)$R^{1a}$, —OS(O)$_2R^{1a}$, —OS(O)$_2OR^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$SR^{1d}$, —$NR^{1a}$C(O)$NR^{1b}R^{1c}$, —$NR^{1a}$C(=$NR^{1d}$)$R^{1b}$, —$NR^{1a}$C(=$NR^{1d}$)$NR^{1b}R^{1c}$, —$NR^{1a}$C(S)$R^{1d}$, —$NR^{1a}$C(S)$OR^{1d}$, —$NR^{1a}$C(S)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —$SR^{1a}$, —SC(O)$R^{1a}$, —SC(O)$NR^{1b}R^{1c}$, —S(O)$R^{1a}$, —S(O)$_2R^{1a}$, —S(O)$_2OR^{1a}$, —S(O)$NR^{1b}R^{1c}$, or —S(O)$_2NR^{1b}R^{1c}$;

$R^2$ is heteroaryl, —$OR^{1a}$, —OC(O)$R^{1a}$, —OC(O)$OR^{1a}$, —OC(O)$NR^{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OP(O)($OR^{1a}$)$OR^{1d}$, —OS(O)$R^{1a}$, —OS(O)$_2R^{1a}$, —OS(O)$_2OR^{1a}$, —OS(O)$NR^{1b}R^{1c}$, or —OS(O)$_2NR^{1b}R^{1c}$; or $R^2$ and $R^3$ together with the carbon atoms to which they are attached form heterocyclylene;

$R^3$ is $C_{1-6}$ alkyl, —$OR^{1a}$, —OC(O)$R^{1a}$, —OC(O)$OR^{1a}$, —OC(O)$NR^{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OP(O)($OR^{1a}$)$OR^{1d}$, —OS(O)$R^{1a}$, —OS(O)$_2R^{1a}$, —OS(O)$_2OR^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$SR^{1d}$, —$NR^{1a}$C(O)$NR^{1b}R^{1c}$, —$NR^{1a}$C(=$NR^{1d}$)$R^{1b}$, —$NR^{1a}$C(=$NR^{1d}$)$NR^{1b}R^{1c}$, —$NR^{1a}$C(S)$R^{1d}$, —$NR^{1a}$C(S)$OR^{1d}$, —$NR^{1a}$C(S)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, or —$NR^{1a}$S(O)$_2NR^{1b}R^{1c}$; and $R^4$ is hydrogen or $R^3$; or $R^3$ and $R^4$ together with the carbon atom to which they are attached form heterocyclylene, =CR$^{1a}R^{1b}$, =CR$^{1a}$CN, =CO, =$NR^{1b}$, =$NOR^{1b}$, =$NNR^{1a}$C(O)$R^{1d}$, or =$NNR^{1a}$C(O)$NR^{1b}R^{1c}$; or $R^3$, $R^4$, and $R^5$ together with the carbon atoms to which they are attached form unsaturated heterocyclylene; or $R^3$, $R^5$, and $R^6$ together with the carbon atoms to which they are attached form unsaturated heterocyclylene;

$R^5$ is $C_{1-6}$ alkyl, —$OR^{1a}$, —OC(O)$R^{1a}$, —OC(O)$OR^{1a}$, —OC(O)$NR^{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OP(O)($OR^{1a}$)$OR^{1d}$, —OS(O)$R^{1a}$, —OS(O)$_2R^{1a}$, —OS(O)$_2OR^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$SR^{1d}$, —$NR^{1a}$C(O)$NR^{1b}R^{1c}$, —$NR^{1a}$C(=$NR^{1d}$)$R^{1b}$, —$NR^{1a}$C(=$NR^{1d}$)$NR^{1b}R^{1c}$, —$NR^{1a}$C(S)$R^{1d}$, —$NR^{1a}$C(S)$OR^{1d}$, —$NR^{1a}$C(S)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, or —$NR^{1a}$S(O)$_2NR^{1b}R^{1c}$; and $R^6$ is hydrogen or $R^5$; or $R^5$ and $R^6$ together with the carbon atom to which they are attached form heterocyclylene, =CR$^{1a}R^{1b}$, =CR$^{1a}$CN, =CO, =$NR^{1b}$, or =$NOR^{1b}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, heterocyclyl, and heterocyclylene is optionally substituted with one or more, in one embodiment, one, two, three, or four, substituents Q, where each Q is independently selected from (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)$OR^a$, —C(O)$NR^bR^c$, —C(O)$SR^a$, —C($NR^a$)$NR^bR^c$, —C(S)$R^a$, —C(S)$OR^a$, —C(S)$NR^bR^c$, —$OR^a$, —OC(O)$R^a$, —OC(O)$OR^a$, —OC(O)$NR^bR^c$, —OC(O)$SR^a$, —OC(=$NR^a$)$NR^bR^c$, —OC(S)$R^a$, —OC(S)$OR^a$, —OC(S)$NR^bR^c$, —OPO$_3R^aR^d$, —OS(O)$R^a$, —OS(O)$_2R^a$, —OSO$_3R^a$, —OS(O)$NR^bR^c$, —OS(O)$_2NR^bR^c$, —$NR^bR^c$, —$NR^a$C(O)$R^d$, —$NR^a$C(O)$OR^d$, —$NR^a$C(O)$NR^bR^c$, —$NR^a$C(O)$SR^d$, —$NR^a$C(=$NR^d$)$NR^bR^c$, —$NR^a$C(S)$R^d$, —$NR^a$C(S)$OR^d$, —$NR^a$C(S)$NR^bR^c$, —$NR^a$S(O)$R^d$, —$NR^a$S(O)$_2R^d$, —$NR^a$S(O)$NR^bR^c$, —$NR^a$S(O)$_2NR^bR^c$, —$SR^a$, —S(O)$R^a$, —S(O)$_2R^a$, —S(O)$NR^bR^c$, and —S(O)$_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)$OR^e$, —C(O)$NR^fR^g$, —C(O)$SR^e$, —C($NR^e$)$NR^fR^g$, —C(S)$R^e$, —C(S)$OR^e$, —C(S)$NR^fR^g$, —$OR^e$, —OC(O)$R^e$, —OC(O)$OR^e$, —OC(O)$NR^fR^g$, —OC(O)$SR^e$, —OC(=$NR^e$)$NR^fR^g$, —OC(S)$R^e$, —OC(S)$OR^e$, —OC(S)$NR^fR^g$, —OS(O)$R^e$, —OS(O)$_2R^e$, —OS(O)$NR^fR^g$, —OS(O)$_2NR^fR^g$, —$NR^fR^g$, —$NR^e$C(O)$R^h$, —$NR^e$C(O)$OR^f$, —$NR^e$C(O)$NR^fR^g$, —$NR^e$C(O)$SR^f$, —$NR^e$C(=$NR^h$)$R^fR^g$, —$NR^e$C(S)$R^h$, —$NR^e$C(S)$OR^f$, —$NR^e$C(S)$NR^fR^g$, —$NR^e$S(O)$R^h$, —$NR^e$S(O)$_2R^h$, —$NR^e$S(O)$NR^fR^g$, —$NR^e$S(O)$_2NR^fR^g$, —$SR^e$, —S(O)$R^e$, —S(O)$_2R^e$, —S(O)$NR^fR^g$, and —S(O)$_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula (I):

(I)

or a diastereomer, a mixture of two or more diastereomers, a tautomer, a mixture of two or more tautomers, or an isotopic variant thereof; or a pharmaceutically acceptable salt, solvate, hydrate, or prodrug thereof;

wherein:

$R^1$ is (i) hydrogen, deuterium, azido, cyano, halo, isocyanato, isothiocyanato, or nitro; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C($R^{1a}$)═$NR^{1b}$, —C($R^{1a}$)═$NOR^{1b}$, —C(O)$R^{1a}$, —C(O)OR$^{1a}$, —C(O)ONR$^{1b}$R$^{1c}$, —C(O)OP(OR$^{1a}$)(OR$^{1b}$), —C(O)N(CN)R$^{1b}$, —C(O)NR$^{1b}$R$^{1c}$, —C(O)N(R$^{1b}$)OR$^{1c}$, —C(O)SR$^{1a}$, —C(═NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, —OS(O)$_2$NR$^{1b}$R$^{1c}$, —NR$^{1b}$R$^{1b}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(═NR$^{1d}$)R$^1$, —NR$^{1a}$C(═NR$^{1d}$)R$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$;

$R^2$ is heteroaryl, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, or —OS(O)$_2$NR$^{1b}$R$^{1c}$;

$R^3$ is $C_{1-6}$ alkyl, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, —OS(O)$_2$ NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(═NR$^{1d}$)R$^{1b}$, —NR$^{1a}$C(═NR$^{1d}$)R$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, or —NR$^{1a}$S(O)$_2$NR$^{1b}$R$^{1c}$; and $R^4$ is hydrogen or $R^3$; or $R^3$ and $R^4$ together with the carbon atom to which they are attached form heterocyclylene, ═CR$^{1a}$R$^{1c}$, ═CR$^{1a}$CN, ═CO, ═NR$^{1b}$, or ═NOR$^{1b}$;

$R^5$ is $C_{1-6}$ alkyl, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, —OS(O)$_2$ NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(═NR$^{1d}$)R$^{1b}$, —NR$^{1a}$C(═NR$^{1d}$)R$^{1b}$R$^{1c}$, —NR$^{1a}$C(S)R$^{1d}$, —NR$^{1a}$C(S)OR$^{1d}$, —NR$^{1a}$C(S) NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, or —NR$^{1a}$S(O)$_2$NR$^{1b}$R$^{1c}$; and $R^6$ is hydrogen or $R^5$; or $R^5$ and $R^6$ together with the carbon atom to which they are attached form heterocyclylene, ═CR$^{1a}$R$^{1c}$, ═CR$^{1a}$CN, ═CO, ═NR$^{1b}$, or ═NOR$^{1b}$; and each R$^{1a}$, R$^{1b}$, R$^{1c}$, and R$^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

wherein each alkyl, alkenyl, alkynyl, cycloalkyl, aryl, aralkyl, heteroaryl, heterocyclyl, and heterocyclylene is optionally substituted with one or more, in one embodiment, one, two, three, or four, substituents Q, where each Q is independently selected from (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(═NR$^a$)NR$^b$R$^c$, —OC(S)R$^a$, —OC(S)OR$^a$, —OC(S)NR$^b$R$^c$, —OPO$_3$R$^a$R$^d$, —OS(O)R$^a$, —OS(O)$_2$R$^a$, —OSO$_3$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(═NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from: (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O) OR$^e$, —C(O)NR$^f$R$^g$, —C(O)SR$^e$, —C(NR$^c$)NR$^f$R$^g$, —C(S)R$^e$, —C(S)OR$^e$, —C(S)NR$^f$R$^g$, —OR$^c$, —OC(O)R$^c$, —OC(O)OR$^c$, —OC(O)NR$^f$R$^g$, —OC(O)SR$^c$, —OC(═NR$^e$)NR$^f$R$^g$, —OC(S)R$^e$, —OC(S)OR$^c$, —OC(S)NR$^f$R$^g$, —OS(O)R$^c$, —OS(O)$_2$R$^c$, —OS(O) NR$^f$R$^g$, —OS(O)$_2$NR$^g$, —NR$^e$, —NR$^c$C(O)R$^h$, —NR$^c$C(O)OR$^f$, —NR$^e$C(O)NR$^f$R$^g$, —NR$^e$C(O)SR$^f$, —NR$^e$C(═NR$^h$)R$^f$R$^g$, —NR$^e$C(S)R$^h$, —NR$^c$C(S)OR$^f$, —NR$^c$C(S)NR$^f$R$^g$, —NR$^e$S(O)R$^h$, —NR$^c$S(O)$_2$R$^h$, —NR$^e$S(O)NR$^f$R$^g$, —NR$^e$S(O)$_2$NR$^f$R$^g$, —SR$^e$, —S(O) R$^c$, —S(O)$_2$R$^e$, —S(O)NR$^f$R$^g$, and —S(O)$_2$NR$^f$R$^g$;

wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula (II):

(II)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, $R^3$, $R^4$, $R^5$, and $R^6$ are each as defined herein.

In yet another embodiment, provided herein is a compound of Formula (III):

(III)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, $R^3$, $R^4$, $R^5$, and $R^6$ are each as defined herein.

In yet another embodiment, provided herein is a compound of Formula (IV):

(IV)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, $R^3$, $R^4$, $R^5$, and $R^6$ are each as defined herein.

In one embodiment, in any one of Formulae I to IV, $R^1$ is (i) hydrogen, deuterium, azido, cyano, halo, isocyanato, isothiocyanato, or nitro; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C($R^{1a}$) =N$R^{1b}$, —C($R^{1a}$)=NO$R^{1b}$, —C(O)$R^{1a}$, —C(O) O$R^{1a}$, —C(O)ONR$^{1b}R^{1c}$, —C(O)OP(O$R^{1a}$)(O$R^{1b}$), —C(O)N(CN)$R^{1b}$, —C(O)NR$^{1b}R^{1c}$, —C(O)N($R^{1b}$) O$R^{1c}$, —C(O)S$R^{1a}$, —C(=N$R^{1a}$)NR$^{1b}R^{1c}$, —C(S) $R^{1a}$, —C(S)O$R^{1a}$, —C(S)NR$^{1b}R^{1c}$, —O$R^{1a}$, —OC(O) $R^{1a}$, —OC(O)O$R^{1a}$, —OC(O)NR$^{1b}R^{1c}$, —OC(O) S$R^{1a}$, —OC(=N$R^{1a}$)NR$^{1b}R^{1c}$, —OC(S)$R^{1a}$, —OC(S) O$R^{1a}$, —OC(S)NR$^{1b}R^{1c}$, —OP(O)(O$R^{1a}$)O$R^{1d}$, —OS (O)$R^{1a}$, —OS(O)$_2R^{1a}$, —OS(O)$_2$O$R^{1a}$, —OS(O) NR$^{1b}R^{1c}$, —OS(O)$_2$NR$^{1b}R^{1c}$, —NR$^{1b}R^{1c}$, —NR$^{1a}$C (O)$R^{1d}$, —NR$^{1a}$C(O)O$R^{1d}$, —NR$^{1a}$C(O)S$R^{1d}$, —NR$^{1a}$C(O)NR$^{1b}R^{1c}$, —NR$^{1a}$C(=N$R^{1d}$)$R^{1b}$, —NR$^{1a}$C(=N$R^{1d}$)$R^{1b}R^{1c}$, —NR$^{1a}$C(S)$R^{1d}$, —NR$^{1a}$C (S)O$R^{1d}$, —NR$^{1a}$C(S)NR$^{1b}R^{1c}$, —NR$^{1a}$S(O)$R^{1d}$, —NR$^{1a}$S(O)$_2R^{1d}$, —NR$^{1a}$S(O)NR$^{1b}R^{1c}$, —NR$^{1a}$S (O)$_2$ NR$^{1b}R^{1c}$, —S$R^{1a}$, —SC(O)$R^{1a}$, —SC(O) NR$^{1b}R^{1c}$, —S(O)$R^{1a}$, —S(O)$_2R^{1a}$, —S(O)$_2$O$R^{1a}$, —S(O)NR$^{1b}R^{1c}$, or —S(O)$_2$NR$^{1b}R^{1c}$;

$R^2$ is heteroaryl, —O$R^{1a}$, or —OC(O)$R^{1a}$;

$R^3$ is $C_{1-6}$ alkyl, —O$R^{1a}$, —OC(O)$R^{1a}$, —OC(O)O$R^{1a}$, —OC(O)ONR$^{1b}R^{1c}$, —OP(O)(O$R^{1a}$)O$R^{1d}$, or —NR$^{1b}R^{1c}$; and $R^4$ is hydrogen, $C_{1-6}$ alkyl, —O$R^{1a}$, —OC(O)$R^{1a}$, —OC(O)O$R^{1a}$, —OC(O)ONR$^{1b}R^{1c}$, —OP(O)(O$R^{1a}$)O$R^{1d}$, or —NR$^{1b}R^{1c}$; or $R^3$ and $R^4$ together with the carbon atom to which they are attached form heterocyclylene, =C$R^{1a}R^{1c}$, =C$R^{1a}$CN, =CO, =N$R^{1b}$, or =NO$R^{1b}$;

$R^5$ is $C_{1-6}$ alkyl, —O$R^{1a}$, —OC(O)$R^{1a}$, —OC(O)O$R^{1a}$, —OC(O)ONR$^{1b}R^{1c}$, —OP(O)(O$R^{1a}$)O$R^{1d}$, or —NR$^{1b}R^{1c}$; and $R^6$ is hydrogen, $C_{1-6}$ alkyl, —O$R^{1a}$, —OC(O)$R^{1a}$, —OC(O)O$R^{1a}$, —OC(O)ONR$^{1b}R^{1c}$, —OP(O)(O$R^{1a}$)O$R^{1d}$, or —NR$^{1b}R^{1c}$; or $R^5$ and $R^6$ together with the carbon atom to which they are attached form heterocyclylene, =C$R^{1a}R^{1b}$, =C$R^{1a}$CN, =CO, =N$R^{1b}$, or =NO$R^{1b}$; and wherein each alkyl, alkenyl, alkynyl, cycloalkyl, aryl, aralkyl, heteroaryl, heterocyclyl, and heterocyclylene is optionally substituted with one or more, in one embodiment, one, two, three, or four, substituents Q; and wherein $R^{1a}$, $R^{1b}$, $R^{1c}$, $R^{1d}$, and Q are each as defined herein.

In another embodiment, in any one of Formulae I to IV,

R$^1$ is (i) hydrogen, azido, cyano, halo, isocyanato, isothiocyanato, or nitro; (ii) C$_{1-6}$ alkyl, C$_{2-6}$ alkenyl, or C$_{2-6}$ alkynyl; or (iii) —C(R$^{1a}$)—NR$^{1b}$, —C(R$^{1a}$)—NOR$^{1b}$, —C(O)R$^{1a}$, —C(O)OR$^{1a}$, —C(O)N(R$^{1b}$)CN, —C(O)NR$^{1b}$R$^{1c}$, —C(O)N(R$^{1b}$)OR$^{1c}$, —C(=NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1ba}$)NR$^{1b}$R$^{1c}$, —OC(S)NR$^{1b}$R$^{1c}$, —OP(O)(OR$^{1a}$)OR$^{1d}$, —OS(O)$_2$R$^{1a}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$S(O)$_2$R$^{1d}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, or —S(O)$_2$NR$^{1b}$R$^{1c}$;

R$^2$ is heteroaryl, —OR$^{1a}$, or —OCOR$^{1a}$;

R$^3$ is C$_{1-6}$ alkyl, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^4$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^3$ and R$^4$ together with the carbon atom to which they are attached form =CR$^{1a}$CN, =CO, =NR$^{1b}$, or =NOR$^{1b}$; and R$^5$ is —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^6$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^5$ and R$^6$ together with the carbon atom to which they are attached form =CR$^{1a}$CN, =CO, =NR$^{1b}$, or =NOR$^{1b}$;

wherein each alkyl, alkenyl, alkynyl, and heteroaryl is optionally substituted with one or more, in one embodiment, one, two, three, or four, substituents Q; and wherein R$^{1a}$, R$^{1b}$, R$^{1c}$, R$^{1d}$, and Q are each as defined herein.

In yet another embodiment, in any one of Formulae I to IV,

R$^1$ is (i) hydrogen, azido, cyano, halo, isocyanato, isothiocyanato, or nitro; (ii) methyl, ethenyl, or ethynyl, each of which is optionally substituted with one or more, in one embodiment, one, two, three, or four, substituents Q; or (iii) —C(R$^{1a}$)—NR$^{1b}$, —C(R$^{1a}$)—NOR$^{1b}$, —C(O)R$^{1a}$, —C(O)OR$^{1a}$, —C(O)N(R$^{1b}$)CN, —C(O)NR$^{1b}$R$^{1c}$, —C(O)N(H)OR$^{1c}$, —C(=NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OC(S)NR$^{1b}$R$^{1c}$, —OP(O)(OR$^{1a}$)OR$^{1d}$, —OS(O)$_2$R$^{1a}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$S(O)$_2$R$^{1d}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, or —S(O)$_2$NR$^{1b}$R$^{1c}$;

R$^2$ is (i) heteroaryl, optionally substituted with one or more, in one embodiment, one, two, three, or four, substituents Q; or (ii) —OR$^{1a}$ or —OCOR$^{1a}$;

R$^3$ is (i) C$_{1-6}$ alkyl, optionally substituted with one or more, in one embodiment, one, two, three, or four, substituents Q; or (ii) —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^4$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^3$ and R$^4$ together with the carbon atom to which they are attached form =CR$^{1a}$CN, =CO, =NR$^{1b}$, or =NOR$^{1b}$; and R$^5$ is —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^6$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^5$ and R$^6$ together with the carbon atom to which they are attached form =CR$^{1a}$CN, =CO, =NR$^{1b}$, or =NOR$^{1b}$;

wherein R$^{1a}$, R$^{1b}$, R$^{1c}$, R$^{1d}$, and Q are each as defined herein.

In yet another embodiment, in any one of Formulae I to IV,

R$^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)NR$^{1b}$R$^{1c}$, —CH$_2$C(O)OP(O)(OR$^a$)OR$^d$, —CH$_2$C(O)SR$^a$, —CH$_2$OR$^a$, —CH$_2$OC(O)NR$^b$R$^c$, —CH$_2$OP(O)(OR$^a$)OR$^d$, —CH$_2$OS(O)$_2$R$^a$, —CH$_2$OS(O)$_2$OR$^a$, —CH$_2$NR$^b$R$^c$, —CH$_2$NR$^a$COR$^d$, —CH$_2$NR$^a$C(O)OR$^d$, —CH$_2$NR$^a$C(O)NR$^b$R$^c$, —CH$_2$NR$^a$C(O)SR$^d$, —CH$_2$NR$^a$C(=NR$^d$)R$^b$R$^c$, —CH$_2$NR$^a$S(O)$_2$R$^d$, —C(H)=CHR$^a$, or —C≡C—R$^a$; or (iii) —C(R$^{1a}$)=NR$^{1b}$, —C(R$^{1a}$)=NOR$^{1b}$, —C(O)R$^{1a}$, —C(O)OR$^{1a}$, —C(O)N(R$^{1b}$)CN, —C(O)NR$^{1b}$R$^{1c}$c, —C(O)N(R$^{1a}$)OR$^{1c}$, —C(=NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OC(S)NR$^{1b}$R$^{1c}$, —OP(O)(OR$^{1a}$)OR$^{1d}$, —OS(O)$_2$R$^{1a}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$S(O)$_2$R$^{1d}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, or —S(O)$_2$NR$^{1b}$R$^{1c}$;

R$^2$ is heteroaryl, —OR$^{1a}$, or —OCOR$^{1a}$;

R$^3$ is C$_{1-6}$ alkyl, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^4$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^3$ and R$^4$ together with the carbon atom to which they are attached form =CR$^{1a}$CN, =CO, or =NOR$^{1b}$; and R$^5$ is —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^6$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^5$ and R$^6$ together with the carbon atom to which they are attached form =CR$^{1a}$CN, =CO, or =NOR$^{1b}$;

wherein each alkyl, aryl, heteroaryl, and heterocyclyl is optionally substituted with one or more, in one embodiment, one, two, three, or four, substituents Q; and wherein R$^a$, R$^b$, R$^c$, R$^d$, R$^{1a}$, R$^{1b}$, R$^{1c}$, R$^{1d}$, and Q are each as defined herein.

In yet another embodiment, in any one of Formulae I to IV,

R$^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)NR$^b$R$^c$, —CH$_2$C(O)OP(O)(OH)OR$^a$, —CH$_2$C(O)SR$^a$, —CH$_2$OR$^a$, —CH$_2$OC(O)NR$^b$R$^c$, —CH$_2$OP(O)(OH)OR$^a$, —CH$_2$OS(O)$_2$R$^a$, —CH$_2$OS(O)$_2$OR$^a$, —CH$_2$NHR$^b$, —CH$_2$NHC(O)R$^d$, —CH$_2$NR$^a$C(O)OR$^{1d}$, —CH$_2$NR$^a$C(O)NR$^b$R$^c$, —CH$_2$NR$^a$C(O)SR$^d$, —CH$_2$NHC(=NR$^d$)NR$^b$R$^c$, —CH$_2$NHS(O)$_2$R$^{1d}$, —C(H)=CHR$^a$, or —C≡C—R$^a$; or (iii) —C(H)=NR$^{1b}$, —C(H)=NOR$^{1b}$, —C(O)R$^{1a}$, —C(O)OR$^{1a}$, —C(O)N(R$^{1b}$)CN, —C(O)NHR$^{1b}$, —C(O)N(H)OR$^{1c}$, —C(=NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NH)NR$^{1b}$R$^{1c}$, —OC(S)NHR$^{1b}$, —OP(O)(OH)R$^{1a}$, —OP(O)(OR$^{1a}$)OR$^{1d}$, —OS(O)$_2$R$^{1a}$, —OS(O)$_2$NR$^{1b}$R$^{1c}$, —NHR$^{1b}$, —NHC(O)R$^{1d}$, —NR$^{1a}$C(O)OR$^{1d}$, —NHC(O)SR$^{1d}$, —NR$^{1a}$C(O)NR$^{1b}$R$^{1c}$, —NHC(=NR$^{1d}$)R$^{1b}$, —NHC(=NR$^{1d}$)NR$^{1b}$R$^{1c}$, —NR$^{1a}$C(=NH)NR$^{1b}$R$^{1c}$, —NHS(O)$_2$R$^{1d}$, —NR$^{1a}$S(O)$_2$R$^{1d}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, or —S(O)$_2$NR$^{1b}$R$^{1c}$;

R$^2$ is heteroaryl, —OR$^{1a}$, or —OCOR$^{1a}$;

R$^3$ is C$_{1-6}$ alkyl, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^4$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^3$ and R$^4$ together with the carbon atom to which they are attached form =CR$^{1a}$CN or =CO; and R$^5$ is —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^6$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^5$ and R$^6$ together with the carbon atom to which they are attached form =CR$^{1a}$CN or =CO;

wherein each alkyl, aryl, heteroaryl, and heterocyclyl is optionally substituted with one or more, in one embodiment, one, two, three, or four, substituents Q; and wherein R$^a$, R$^b$, R$^c$, R$^d$, R$^{1a}$, R$^{1b}$, R$^{1c}$, R$^{1d}$, and Q are each as defined herein.

In yet another embodiment, in any one of Formulae I to IV,

R$^1$ is (i) hydrogen, azido, cyano, isocyanato, isothiocyanato, or nitro; (ii) —CH$_2$C(O)OPO(OH)$_2$, —CH$_2$OH, —CH$_2$OPO(OH)$_2$, —CH$_2$NH$_2$, morpholin-4-ylmethyl, piperazin-1-ylmethyl, or 4-methyl-piperazin-1-ylmethyl; (iii)

or (iv) —COH, —COOH, —C(O)OCH$_3$, —COOCH$_2$CH$_3$, 1,2,3-benzotriazol-1-yloxycarbonyl, benzyloxycarbonyl, pyrrolidin-1-ylcarbonyl, —CONH$_2$, —CONHCH$_3$, —CONHCH$_2$CH$_3$, —CONHCH$_2$CH$_2$CH$_3$, —CON(CH$_3$)$_2$, —CONHOH, —CONHCN, —OH, —OPO$_3$H$_2$, —NH$_2$, —NHCONH$_2$, —NHSO$_2$NH$_2$, —SH, —SO$_2$H, or —SO$_3$H;

R$^2$ is —OH, —OCH$_3$, —OCD$_3$, —OCH$_2$CH$_3$, —OCH$_2$CF$_3$, —OCOCH$_3$, or indolyl;

R$^3$ is —CH$_2$CN, —OH, —OCOCH$_3$, —OCOCH$_2$CH$_3$, —OCOCH$_2$CH$_2$CH$_3$, —OC(O)OCH$_2$CH$_3$, —OC(O)ONHCH$_2$CH$_3$, —OP(O)(OCH$_3$)$_2$, or —OP(O)(OCH$_2$CH$_3$)$_2$; and R$^4$ is hydrogen; or R$^3$ and R$^4$ together with the carbon atom to which they are attached form =CHCN or =CO; and R$^5$ is —OH, —OCOCH$_3$, —OCOCH$_2$CH$_3$, —OCOCH$_2$CH$_2$CH$_3$, —OC(O)OCH$_2$CH$_3$, —OC(O)ONHCH$_2$CH$_3$, —OP(O)(OCH$_3$)$_2$, or —OP(O)(OCH$_2$CH$_3$)$_2$; and R$^6$ is hydrogen; or R$^5$ and R$^6$ together with the carbon atom to which they are attached form =CHCN or =CO.

In yet another embodiment, in any one of Formulae I to IV,

R$^1$ is cyano, C$_{1-6}$ alkyl, —COOR$^{1a}$, —CONR$^{1b}$R$^{1c}$, —NR$^{1b}$R$^{1c}$, or —NR$^{1a}$C(O)NR$^{1b}$R$^{1c}$;

R$^2$ is heteroaryl, —OR$^{1a}$, or —OC(O)R$^{1a}$;

R$^3$ is C$_{1-6}$ alkyl, —OR$^{1a}$, or —OC(O)R$^{1a}$; and R$^4$ is hydrogen, —OR$^{1a}$, or —OC(O)R$^{1a}$; or R$^3$ and R$^4$ together with the carbon atom to which they are attached form =CR$^{1a}$CN, =CO, =NR$^{1b}$, or =NOR$^{1b}$; and R$^5$ is —OR$^{1a}$ or —OC(O)R$^{1a}$; and R$^6$ is hydrogen, —OR$^{1a}$, or —OC(O)R$^{1a}$; or R$^5$ and R$^6$ together with the carbon atom to which they are attached form =CR$^{1a}$CN, =CO, =NR$^{1b}$, or =NOR$^{1b}$;

wherein each alkyl and heteroaryl is optionally substituted with one or more, in one embodiment, one, two, three, or four, substituents Q; and wherein R$^{1a}$, R$^{1b}$, R$^{1c}$, and Q are each as defined herein.

In yet another embodiment, in any one of Formulae I to IV,

R$^1$ is cyano, C$_{1-6}$ alkyl, —COOR$^{1a}$, —CONR$^{1b}$R$^{1c}$, —NR$^{1b}$R$^{1c}$, or —NR$^{1a}$C(O)NR$^{1b}$R$^{1c}$; wherein R$^{1a}$ is hydrogen, C$_{1-6}$ alkyl, C$_{7-15}$ aralkyl, or heteroaryl; and R$^{1b}$ and R$^{1c}$ are each independently hydrogen or C$_{1-6}$ alkyl;

R$^2$ is heteroaryl, —O—C$_{1-6}$ alkyl, or —OCO—C$_{1-6}$ alkyl;

R$^3$ is C$_{1-6}$ alkyl, —OH, —O—C$_{1-6}$ alkyl, or —OCO—C$_{1-6}$ alkyl; and R$^4$ is hydrogen, —OH, —O—C$_{1-6}$ alkyl, or —OCO—C$_{1-6}$ alkyl; or R$^3$ and R$^4$ together with the carbon atom to which they are attached form =CHCN or =CO; and R$^5$ is —OH, —O—C$_{1-6}$ alkyl, or —OCO—C$_{1-6}$ alkyl; and R$^6$ is hydrogen, —OH, —O—C$_{1-6}$ alkyl, or —OCO—C$_{1-6}$ alkyl; or R$^5$ and R$^6$ together with the carbon atom to which they are attached form =CHCN or =CO;

wherein each alkyl, aralkyl, and heteroaryl is optionally substituted with one or more, in one embodiment, one, two, three, or four, substituents Q; and wherein Q is as defined herein.

In still another embodiment, in any one of Formulae I to IV,

R$^1$ is cyano, —CH$_2$OH, —CH$_2$NH$_2$, —CHO, —COOH, —COOCH$_3$, 1,2,3-benzotriazol-1-yloxycarbonyl, benzyloxycarbonyl, —CONH$_2$, —CONHCH$_3$, —CONHCH$_2$CH$_3$, —CONHCH$_2$CH$_2$CH$_3$, —CON(CH$_3$)$_2$, —NH$_2$, or —NHCONH$_2$;

R$^2$ is —OCH$_3$, —OCD$_3$, —OCH$_2$CH$_3$, —OCOCH$_3$, or indol-3-yl;

R$^3$ is —CH$_2$CN, —OH or —OCOCH$_2$CH$_2$CH$_3$; and R$^4$ is hydrogen, —OH, or —OCOCH$_2$CH$_2$CH$_3$; or R$^3$ and R$^4$ together with the carbon atom to which they are attached form =CHCN or =CO; and R$^5$ is —OH or —OCOCH$_2$CH$_2$CH$_3$; and R$^6$ is hydrogen, —OH, or —OCOCH$_2$CH$_2$CH$_3$; or R$^5$ and R$^6$ together with the carbon atom to which they are attached form =CHCN or =CO.

In yet another embodiment, provided herein is a compound of Formula (V):

(V)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, and $R^4$ are each as defined herein.

In yet another embodiment, provided herein is a compound of Formula (VI):

(VI)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, and $R^4$ are each as defined herein.

In yet another embodiment, provided herein is a compound of Formula (VII):

(VII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, and $R^4$ are each as defined herein.

In yet another embodiment, provided herein is a compound of Formula (VIII):

(VIII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, and $R^4$ are each as defined herein.

In one embodiment, in any one of Formulae V to VIII, $R^1$ is (i) hydrogen, azido, cyano, halo, isocyanato, isothiocyanato, or nitro; (ii) $C_{1-6}$ alkyl, $C_{2-6}$ alkenyl, or $C_{2-6}$ alkynyl; or (iii) —C($R^{1a}$)=N$R^1$, —C($R^{1a}$)=NOR$^{1b}$, —C(O)$R^{1a}$, —C(O)OR$^{1a}$, —C(O)N($R^{1b}$)CN, —C(O)NR$^{1b}$R$^{1c}$, —C(O)N($R^{1b}$)OR$^{1c}$, —C(=NR$^{1a}$)NR$^{1b}$R$^{1c}$, —OR$^{1a}$, —OC(O)$R^{1a}$, —OC(O)OR$^{1a}$, —OC(O)NR$^{1b}$R$^{1c}$, —OC(=NR$^{1ba}$)NR$^{1b}$R$^{1c}$, —OC(S)NR$^{1b}$R$^{1c}$, —OP(O)(OR$^{1a}$)OR$^{1d}$, —OS(O)$_2$R$^{1a}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^d$)NR$^{1b}$R$^{1c}$, —NR$^{1a}$S(O)$_2$R$^{1d}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^a$, —S(O)$_2$OR$^{1a}$, or —S(O)$_2$NR$^{1b}$R$^{1c}$;

$R^2$ is heteroaryl, —OR$^{1a}$, or —OCOR$^{1a}$; and $R^3$ is $C_{1-6}$ alkyl, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; and R$^4$ is hydrogen, —OR$^{1a}$, —OC(O)R$^{1a}$, —OC(O)OR$^{1a}$, —OC(O)ONR$^{1b}$R$^{1c}$, or —OP(O)(OR$^{1a}$)OR$^{1d}$; or R$^3$ and R$^4$ together with the carbon atom to which they are attached form =CR$^{1a}$CN, =CO, =NR$^{1b}$, or =NOR$^{1b}$;

wherein each alkyl, alkenyl, alkynyl, and heteroaryl is optionally substituted with one or more, in one embodiment, one, two, three, or four, substituents Q; and wherein $R^{1a}$, $R^{1b}$, $R^{1c}$, $R^{1d}$, and Q are each as defined herein.

In another embodiment, in any one of Formulae V to VIII, $R^1$ is (i) hydrogen, azido, cyano, halo, isocyanato, isothiocyanato, or nitro; (ii) methyl, ethenyl, or ethynyl, each of which is optionally substituted with one or more, in one embodiment, one, two, three, or four, substituents Q; or (iii) —C($R^{1a}$)=N$R^{1b}$, —C($R^{1a}$)=NOR$^{1b}$, —C(O)$R^{1a}$, —C(O)OR$^{1a}$, —C(O)N($R^{1b}$)CN, —C(O)NR$^{1b}$R$^{1c}$, —C(O)N(H)OR$^{1c}$, —C(=NR$^{1a}$)NR$^{1b}$R$^{1c}$, —OR$^{1a}$, —OC(O)$R^{1a}$, —OC(O)OR$^{1a}$, —OC(O)NR$^{1b}$R$^{1c}$, —OC(=NR$^{1a}$)NR$^{1b}$R$^{1c}$, —OC(S)NR$^{1b}$R$^{1c}$, —OP(O)(OR$^{1a}$)OR$^{1d}$, —OS(O)$_2$R$^{1a}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$S(O)$_2$R$^{1d}$, —NR$^{1a}$S(O)$_2$ NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, or —S(O)$_2$NR$^{1b}$R$^{1c}$;

R² is (i) heteroaryl, optionally substituted with one or more, in one embodiment, one, two, three, or four, substituents Q; or (ii) —OR¹ᵃ or —OCOR¹ᵃ; and R³ is (i) C₁₋₆ alkyl, optionally substituted with one or more, in one embodiment, one, two, three, or four, substituents Q; or (ii) —OR¹ᵃ, —OC(O)R¹ᵃ, —OC(O)OR¹ᵃ, —OC(O)ONR¹ᵇR¹ᶜ, or —OP(O)(OR¹ᵃ)OR¹ᵈ; and R⁴ is hydrogen, —OR¹ᵃ, —OC(O)R¹ᵃ, —OC(O)OR¹ᵃ, —OC(O)ONR¹ᵇR¹ᶜ, or —OP(O)(OR¹ᵃ)OR¹ᵈ; or R³ and R⁴ together with the carbon atom to which they are attached form =CR¹ᵃCN, =CO, =NR¹ᵇ, or =NOR¹ᵇ;

wherein R¹ᵃ, R¹ᵇ, R¹ᶜ, R¹ᵈ, and Q are each as defined herein.

In yet another embodiment, in any one of Formulae V to VIII,

R¹ is (i) hydrogen, azido, cyano, halo, isocyanato, isothiocyanato, or nitro; (ii) —CH₂—C₆₋₁₄ aryl, —CH₂-heteroaryl, —CH₂-heterocyclyl, —CH₂C(O)NRᵇRᶜ, —CH₂C(O)OP(O)(ORᵃ)ORᵈ, —CH₂C(O)SRᵃ, —CH₂ORᵃ, —CH₂OC(O)NRᵇRᶜ, —CH₂OP(O)(ORᵃ)ORᵈ, —CH₂OS(O)₂Rᵃ, —CH₂OS(O)₂ORᵃ, —CH₂NRᵇRᶜ, —CH₂NRᵃCORᵈ, —CH₂NRᵃC(O)ORᵈ, —CH₂NRᵃC(O)NRᵇRᶜ, —CH₂NRᵃC(O)SRᵈ, —CH₂NRᵃC(=NRᵈ)RᵇRᶜ, —CH₂NRᵃS(O)₂Rᵈ, —C(H)=CHRᵃ, or —C≡C—Rᵃ; or (iii) —C(R¹ᵃ)=NR¹ᵇ, —C(R¹ᵃ)=NOR¹ᵇ, —C(O)R¹ᵃ, —C(O)OR¹ᵃ, —C(O)N(R¹ᵇ)CN, —C(O)NR¹ᵇR¹ᶜ, —C(O)N(R¹ᵃ)OR¹ᶜ, —C(=NR¹ᵃ)NR¹ᵇR¹ᶜ, —OR¹ᵃ, —OC(O)R¹ᵃ, —OC(O)OR¹ᵃ, —OC(O)NR¹ᵇR¹ᶜ, —OC(=NR¹ᵃ)NR¹ᵇR¹ᶜ, —OC(S)NR¹ᵇR¹ᶜ, —OP(O)(OR¹ᵃ)OR¹ᵈ, —OS(O)₂R¹ᵃ, —OS(O)₂NR¹ᵇR¹ᶜ, —NR¹ᵇR¹ᶜ, —NR¹ᵃC(O)R¹ᵈ, —NR¹ᵃC(O)OR¹ᵈ, —NR¹ᵃC(O)SR¹ᵈ, —NR¹ᵃC(O)NR¹ᵇR¹ᶜ, —NR¹ᵃC(=NR¹ᵈ)R¹ᵇ, —NR¹ᵃC(=NR¹ᵈ)NR¹ᵇR¹ᶜ, —NR¹ᵃS(O)₂R¹ᵈ, —NR¹ᵃS(O)₂NR¹ᵇR¹ᶜ, —SR¹ᵃ, —SC(O)R¹ᵃ, —SC(O)NR¹ᵇR¹ᶜ, —S(O)R¹ᵃ, —S(O)₂R¹ᵃ, —S(O)₂OR¹ᵃ, or —S(O)₂NR¹ᵇR¹ᶜ;

R² is heteroaryl, —OR¹ᵃ, or —OCOR¹ᵃ; and

R³ is C₁₋₆ alkyl, —OR¹ᵃ, —OC(O)R¹ᵃ, —OC(O)OR¹ᵃ, —OC(O)ONR¹ᵇR¹ᶜ, or —OP(O)(OR¹ᵃ)OR¹ᵈ; and R⁴ is hydrogen, —OR¹ᵃ, —OC(O)R¹ᵃ, —OC(O)OR¹ᵃ, —OC(O)ONR¹ᵇR¹ᶜ, or —OP(O)(OR¹ᵃ)OR¹ᵈ; or R³ and R⁴ together with the carbon atom to which they are attached form =CR¹ᵃCN, =CO, or =NOR¹ᵇ;

wherein each alkyl, aryl, heteroaryl, and heterocyclyl is optionally substituted with one or more, in one embodiment, one, two, three, or four, substituents Q; and wherein Rᵃ, Rᵇ, Rᶜ, Rᵈ, R¹ᵃ, R¹ᵇ, R¹ᶜ, R¹ᵈ, and Q are each as defined herein.

In yet another embodiment, in any one of Formulae V to VIII,

R¹ is (i) hydrogen, azido, cyano, halo, isocyanato, isothiocyanato, or nitro; (ii) —CH₂—C₆₋₁₄ aryl, —CH₂-heteroaryl, —CH₂-heterocyclyl, —CH₂C(O)NRᵇRᶜ, —CH₂C(O)OP(O)(OH)ORᵃ, —CH₂ORᵃ, —CH₂OC(O)NRᵇRᶜ, —CH₂OP(O)(OH)ORᵃ, —CH₂OS(O)₂Rᵃ, —CH₂OS(O)₂ORᵃ, —CH₂NHRᵇ, —CH₂NHC(O)Rᵈ, —CH₂NRᵃC(O)ORᵈ, —CH₂NRᵃC(O)NRᵇRᶜ, —CH₂NRᵃC(O)SRᵈ, —CH₂NHC(=NRᵈ)RᵇRᶜ, —CH₂NHS(O)₂Rᵈ, —C(H)=CHRᵃ, or —C≡C—Rᵃ; or (iii) —C(H)=NR¹ᵇ, —C(H)=NOR¹ᵇ, —C(O)R¹ᵃ, —C(O)OR¹ᵃ, —C(O)N(R¹ᵇ)CN, —C(O)NHR¹ᵇ, —C(O)N(H)OR¹ᶜ, —C(=NR¹ᵃ)NR¹ᵇR¹ᶜ, —OR¹ᵃ, —OC(O)R¹ᵃ, —OC(O)OR¹ᵃ, —OC(O)NR¹ᵇR¹ᶜ, —OC(=NH)NR¹ᵇR¹ᶜ, —OC(S)NHR¹ᵇ, —OP(O)(OH)R¹ᵃ, —OP(O)(OR¹ᵃ)

OR¹ᵈ, —OS(O)₂R¹ᵃ, —OS(O)₂NR¹ᵇR¹ᶜ, —NHR¹ᵇ, —NHC(O)R¹ᵈ, —NR¹ᵃC(O)OR¹ᵈ, —NHC(O)SR¹ᵈ, —NR¹ᵃC(O)NR¹ᵇR¹ᶜ, —NHC(=NR¹ᵈ)R¹ᵇ, —NHC(=NR¹ᵈ)R¹ᵇR¹ᶜ, —NR¹ᵃC(=NH)NR¹ᵇR¹ᶜ, —NHS(O)₂R¹ᵈ, —NR¹ᵃS(O)₂R¹ᵈ, —NR¹ᵃS(O)₂NR¹ᵇR¹ᶜ, —SR¹ᵃ, —SC(O)R¹ᵃ, —SC(O)NR¹ᵇR¹ᶜ, —S(O)R¹ᵃ, —S(O)₂R¹ᵃ, —S(O)₂OR¹ᵃ, or —S(O)₂NR¹ᵇR¹ᶜ;

R² is heteroaryl, —OR¹ᵃ, or —OCOR¹ᵃ; and

R³ is C₁₋₆ alkyl, —OR¹ᵃ, —OC(O)R¹ᵃ, —OC(O)OR¹ᵃ, —OC(O)ONR¹ᵇR¹ᶜ, or —OP(O)(OR¹ᵃ)OR¹ᵈ; and R⁴ is hydrogen, —OR¹ᵃ, —OC(O)R¹ᵃ, —OC(O)OR¹ᵃ, —OC(O)ONR¹ᵇR¹ᶜ, or —OP(O)(OR¹ᵃ)OR¹ᵈ; or R³ and R⁴ together with the carbon atom to which they are attached form =CR¹ᵃCN or =CO;

wherein each alkyl, aryl, heteroaryl, and heterocyclyl is optionally substituted with one or more, in one embodiment, one, two, three, or four, substituents Q; and wherein Rᵃ, Rᵇ, Rᶜ, Rᵈ, R¹ᵃ, R¹ᵇ, R¹ᶜ, R¹ᵈ, and Q are each as defined herein.

In yet another embodiment, in any one of Formulae V to VIII,

R¹ is (i) hydrogen, azido, cyano, isocyanato, isothiocyanato, or nitro; (ii) —CH₂C(O)OPO(OH)₂, —CH₂OH, —CH₂OPO(OH)₂, —CH₂NH₂, morpholin-4-ylmethyl, piperazin-1-ylmethyl, or 4-methyl-piperazin-1-ylmethyl; (iii)

or (iv) —COH, —COOH, —C(O)OCH₃, —COOCH₂CH₃, 1,2,3-benzotriazol-1-yloxycarbonyl, benzyloxycarbonyl, pyrrolidin-1-ylcarbonyl, —CONH₂, —CONHCH₃, —CONHCH₂CH₃, —CONHCH₂CH₂CH₃, —CON(CH₃)₂, —CONHOH, —CONHCN, —OH, —OPO₃H₂, —NH₂, —NHCONH₂, —NHSO₂NH₂, —SH, —SO₂H, or —SO₃H;

R² is —OH, —OCH₃, —OCD₃, —OCH₂CH₃, —OCH₂CF₃, —OCOCH₃, or indolyl; and

R³ is —CH₂CN, —OH, —OCOCH₃, —OCOCH₂CH₃, —OCOCH₂CH₂CH₃, —OC(O)OCH₂CH₃, —OC(O)ONHCH₂CH₃, —OP(O)(OCH₃)₂, or —OP(O)(OCH₂CH₃)₂; and R⁴ is hydrogen; or R³ and R⁴ together with the carbon atom to which they are attached form =CHCN or =CO.

In yet another embodiment, in any one of Formulae V to VIII,

R¹ is cyano, C₁₋₆ alkyl, —COOR¹ᵃ, —CONR¹ᵇR¹ᶜ, —NR¹ᵇR¹ᶜ, or —NR¹ᵃC(O)NR¹ᵇR¹ᶜ;

R² is heteroaryl, —OR¹ᵃ, or —OC(O)R¹ᵃ; and $R^3$ is $C_{1-6}$ alkyl, —$OR^{1a}$, or —$OC(O)R^{1a}$; and $R^4$ is hydrogen, —$OR^{1a}$, or —$OC(O)R^{1a}$; or $R^3$ and $R^4$ together with the carbon atom to which they are attached form =$CR^{1a}CN$, =$CO$, =$NR^{1b}$, or =$NOR^{1b}$;

wherein each alkyl and heteroaryl is optionally substituted with one or more, in one embodiment, one, two, three, or four, substituents Q; and wherein $R^{1a}$, $R^{1b}$, $R^{1c}$, and Q are each as defined herein. In yet another embodiment, in any one of Formulae V to VIII, $R^1$ is cyano, $C_{1-6}$ alkyl, —$COOR^{1a}$, —$CONR^{1b}R^{1c}$, —$NR^{1b}R^{1c}$, or —$NR^{1a}C(O)NR^{1b}R^{1c}$; wherein $R^{1a}$ is hydrogen, $C_{1-6}$ alkyl, $C_{7-15}$ aralkyl, or heteroaryl; and $R^{1b}$ and $R^{1c}$ are each independently hydrogen or $C_{1-6}$ alkyl;

$R^2$ is heteroaryl, —O—$C_{1-6}$ alkyl, or —OCO—$C_{1-6}$ alkyl; and $R^3$ is $C_{1-6}$ alkyl, —OH, —O—$C_{1-6}$ alkyl, or —OCO—$C_{1-6}$ alkyl; and $R^4$ is hydrogen, —OH, —O—$C_{1-6}$ alkyl, or —OCO—$C_{1-6}$ alkyl; or $R^3$ and $R^4$ together with the carbon atom to which they are attached form =CHCN or =CO;

wherein each alkyl, aralkyl, and heteroaryl is optionally substituted with one or more, in one embodiment, one, two, three, or four, substituents Q; and wherein Q is as defined herein. In still another embodiment, in any one of Formulae V to VIII, $R^1$ is cyano, —$CH_2OH$, —$CH_2NH_2$, —CHO, —COOH, —$COOCH_3$, 1,2,3-benzotriazol-1-yloxycarbonyl, benzyloxycarbonyl, —$CONH_2$, —$CONHCH_3$, —$CONHCH_2CH_3$, —$CONHCH_2CH_2CH_3$, —$CON(CH_3)_2$, —$NH_2$, or —$NHCONH_2$;

$R^2$ is —$OCH_3$, —$OCD_3$, —$OCH_2CH_3$, —$OCOCH_3$, or indol-3-yl; and $R^3$ is —$CH_2CN$, —OH, or —$OCOCH_2CH_2CH_3$; and $R^4$ is hydrogen, —OH, or —$OCOCH_2CH_2CH_3$; or $R^3$ and $R^4$ together with the carbon atom to which they are attached form =CHCN or =CO.

In yet another embodiment, provided herein is a compound of Formula (IX):

(IX)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$ and $R^2$ are each as defined herein.

In yet another embodiment, provided herein is a compound of Formula (X):

(X)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$ and $R^2$ are each as defined herein.

In yet another embodiment, provided herein is a compound of Formula (XI):

(XI)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$ and $R^2$ are each as defined herein.

In yet another embodiment, provided herein is a compound of Formula (XII):

(XII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$ and $R^2$ are each as defined herein.

In one embodiment, in any one of Formulae IX to XII, $R^1$ is (i) hydrogen, azido, cyano, halo, isocyanato, isothiocyanato, or nitro; (ii) $C_1$-6 alkyl, $C_{2-6}$ alkenyl, or $C_{2-6}$ alkynyl; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)N$R^{1b}R^{1c}$, —C(O)N($R^{1b}$)O$R^{1c}$, —C(=N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1ba}$)N$R^{1b}R^{1c}$, —OC(S)N$R^{1b}R^{1c}$, —OP(O)(O$R^{1a}$)O$R^{1d}$, —OS(O)$_2R^{1a}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)S$R^{1d}$, —N$R^{1a}$C(O)N$R^{1b}R^{1c}$, —N$R^{1a}$C(=N$R^{1d}$)$R^{1b}$, —N$R^{1a}$C(=N$R^{1d}$)N$R^{1b}R^{1c}$, —N$R^{1a}$S(O)$_2R^{1d}$, —N$R^{1a}$S(O)$_2$N$R^{1b}R^{1c}$, —S$R^{1a}$, —SC(O)$R^{1a}$, —SC(O)N$R^{1b}R^{1c}$, —S(O)$R^{1a}$, —S(O)$_2R^{1a}$, —S(O)$_2$O$R^{1a}$, or —S(O)$_2$N$R^{1b}R^{1c}$; and $R^2$ is heteroaryl, —O$R^{1a}$, or —OCO$R^{1a}$;

wherein the alkyl, alkenyl, alkynyl, and heteroaryl are each optionally substituted with one or more, in one embodiment, one, two, three, or four, substituents Q; and wherein $R^{1a}$, $R^{1b}$, $R^{1c}$, $R^{1d}$, and Q are each as defined herein.

In another embodiment, in any one of Formulae IX to XII, $R^1$ is (i) hydrogen, azido, cyano, halo, isocyanato, isothiocyanato, or nitro; (ii) methyl, ethenyl, or ethynyl, each of which is optionally substituted with one or more, in one embodiment, one, two, three, or four, substituents Q; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)N$R^{1b}R^{1c}$, —C(O)N(H)O$R^{1c}$, —C(=N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OC(S)N$R^{1b}R^{1c}$, —OP(O)(O$R^{1a}$)O$R^{1d}$, —OS(O)$_2R^{1a}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)S$R^{1d}$, —N$R^{1a}$C(O)N$R^{1b}R^{1c}$, —N$R^{1a}$C(=N$R^{1d}$)$R^{1b}$, —N$R^{1a}$C(=N$R^{1d}$)N$R^{1b}R^{1c}$, —N$R^{1a}$S(O)$_2R^{1d}$, —N$R^{1a}$S(O)$_2$ N$R^{1b}R^{1c}$, —S$R^{1a}$, —SC(O)$R^{1a}$, —SC(O)N$R^{1b}R^{1c}$, —S(O)$R^{1a}$, —S(O)$_2R^{1a}$, —S(O)$_2$O$R^{1a}$, or —S(O)$_2$ N$R^{1b}R^{1c}$; and $R^2$ is (i) heteroaryl, optionally substituted with one or more, in one embodiment, one, two, three, or four, substituents Q; or (ii) —O$R^{1a}$ or —OCO$R^{1a}$;

wherein $R^{1a}$, $R^{1b}$, $R^{1c}$, $R^{1d}$, and Q are each as defined herein.

In yet another embodiment, in any one of Formulae IX to XII, $R^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)N$R^bR^c$, —CH$_2$C(O)OP(O)(O$R^a$)O$R^d$, —CH$_2$C(O)S$R^a$, —CH$_2$O$R^a$, —CH$_2$OC(O)N$R^bR^c$, —CH$_2$OP(O)(O$R^a$)O$R^d$, —CH$_2$OS(O)$_2R^a$, —CH$_2$OS(O)$_2$O$R^a$, —CH$_2$N$R^bR^c$, —CH$_2$N$R^a$COR$^d$, —CH$_2$N$R^a$C(O)O$R^d$, —CH$_2$N$R^a$C(O)N$R^bR^c$, —CH$_2$N$R^a$C(O)S$R^d$, —CH$_2$N$R^a$C(=N$R^d$)$R^bR^c$, —CH$_2$N$R^a$S(O)$_2R^d$, —C(H)=CHR$^a$, or —C≡C—R$^a$; or (iii) —C(R$^{1a}$)=N$R^{1b}$, —C(R$^{1a}$)=NO$R^{1b}$, —C(O)$R^{1a}$, —C(O)O$R^{1a}$, —C(O)N(R$^{1b}$)CN, —C(O)N$R^{1b}R^{1c}$, —C(O)N(R$^{1a}$)O$R^{1c}$, —C(=N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OC(S)N$R^{1b}R^{1c}$, —OP(O)(O$R^{1a}$)O$R^{1d}$, —OS(O)$_2R^{1a}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)SR$^{1d}$, —N$R^{1a}$C(O)N$R^{1b}R^{1c}$, —N$R^{1a}$C(=N$R^{1d}$)$R^{1b}$, —N$R^{1a}$C(=N$R^{1d}$)N$R^{1b}R^{1c}$, —N$R^{1a}$S(O)$_2R^{1d}$, —N$R^{1a}$S(O)$_2$N$R^{1b}R^{1c}$, —S$R^{1a}$, —SC(O)$R^{1a}$, —SC(O)N$R^{1b}R^{1c}$, —S(O)$R^{1a}$, —S(O)$_2R^a$, —S(O)$_2$O$R^{1a}$, or —S(O)$_2$N$R^{1b}R^{1c}$; and $R^2$ is heteroaryl, —O$R^{1a}$, or —OCO$R^{1a}$;

wherein each aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae IX to XII, $R^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)N$R^bR^c$, —CH$_2$C(O)OP(O)(OH)O$R^a$, —CH$_2$C(O)S$R^a$, —CH$_2$O$R^a$, —CH$_2$OC(O)N$R^bR^c$, —CH$_2$OP(O)(OH)O$R^a$, —CH$_2$OS(O)$_2R^a$, —CH$_2$OS(O)$_2$O$R^a$, —CH$_2$NHR$^b$, —CH$_2$NHC(O)R$^d$, —CH$_2$N$R^a$C(O)O$R^d$, —CH$_2$N$R^a$C(O)N$R^bR^c$, —CH$_2$N$R^a$C(O)S$R^d$, —CH$_2$NHC(=N$R^d$)$R^bR^c$, —CH$_2$NHS(O)$_2R^d$, —C(H)=CHR$^a$, or —C≡C—R$^a$; or (iii) —C(H)=N$R^{1b}$, —C(H)=NO$R^{1b}$, —C(O)$R^{1a}$, —C(O)O$R^{1a}$, —C(O)N(R$^{1b}$)CN, —C(O)NHR$^{1b}$, —C(O)N(H)O$R^{1c}$, —C(=N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=NH)N$R^{1b}R^{1c}$, —OC(S)NHR$^{1b}$, —OP(O)(OH)$R^{1a}$, —OP(O)(O$R^{1a}$)O$R^{1d}$, —OS(O)$_2R^{1a}$, —OS(O)$_2$N$R^{1b}R^{1c}$, —NHR$^{1b}$, —NHC(O)R$^{1d}$, —N$R^{1a}$C(O)O$R^{1d}$, —NHC(O)SR$^{1d}$, —N$R^{1a}$C(O)N$R^{1b}R^{1c}$, —NHC(=N$R^{1d}$)$R^{1b}$, —NHC(=N$R^{1d}$)$R^{1b}R^{1c}$, —N$R^{1a}$C(=NH)N$R^{1b}R^{1c}$, —NHS(O)$_2R^{1d}$, —N$R^{1a}$S(O)$_2R^{1d}$, —N$R^{1a}$S(O)$_2$N$R^{1b}R^{1c}$, —S$R^{1a}$, —SC(O)$R^{1a}$, —SC(O)N$R^{1b}R^{1c}$, —S(O)$R^{1a}$, —S(O)$_2R^{1a}$, —S(O)$_2$O$R^{1a}$, or —S(O)$_2$N$R^{1b}R^{1c}$; and $R^2$ is heteroaryl, —O$R^{1a}$, or —OCO$R^{1a}$;

wherein each aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae IX to XII, $R^1$ is (i) hydrogen, azido, cyano, isocyanato, isothiocyanato, or nitro; (ii) —CH$_2$C(O)OPO(OH)$_2$, —CH$_2$OH, —CH$_2$OPO(OH)$_2$, —CH$_2$NH$_2$, morpholin-4-ylmethyl, piperazin-1-ylmethyl, or 4-methyl-piperazin-1-ylmethyl; (iii)

or (iv) —COH, —COOH, —C(O)OCH$_3$, —COOCH$_2$CH$_3$, 1,2,3-benzotriazol-1-yloxycarbonyl, benzyloxycarbonyl, pyrrolidin-1-ylcarbonyl, —CONH$_2$, —CONHCH$_3$, —CONHCH$_2$CH$_3$, —CONHCH$_2$CH$_2$CH$_3$, —CON(CH$_3$)$_2$, —CONHOH, —CONHCN, —OH, —OPO$_3$H$_2$, —NH$_2$, —NHCONH$_2$, —NHSO$_2$NH$_2$, —SH, —SO$_2$H, or —SO$_3$H; and R$^2$ is indolyl, —OH, —OCH$_3$, —OCD$_3$, —OCH$_2$CH$_3$, —OCH$_2$CF$_3$, or —OCOCH$_3$.

In yet another embodiment, in any one of Formulae IX to XII,

R$^1$ is cyano, C$_{1-6}$ alkyl, —COOR$^{1a}$, —CONR$^{1b}$R$^{1c}$, —NR$^{1b}$R$^{1c}$, or —NR$^{1a}$C(O)NR$^{1b}$R$^{1c}$; and R$^2$ is heteroaryl, —OR$^{1a}$, or —OC(O)R$^{1a}$;

wherein the alkyl and heteroaryl are each optionally substituted with one or more, in one embodiment, one, two, three, or four, substituents Q; and wherein R$^{1a}$, R$^{1b}$, R$^{1c}$, and Q are each as defined herein.

In yet another embodiment, in any one of Formulae IX to XII,

R$^1$ is cyano, C$_{1-6}$ alkyl, —COOR$^{1a}$, —CONR$^{1b}$R$^{1c}$, —NR$^{1b}$R$^{1c}$, or —NR$^{1a}$C(O)NR$^{1b}$R$^{1c}$; wherein R$^{1a}$ is hydrogen, C$_{1-6}$ alkyl, C$_{7-15}$ aralkyl, or heteroaryl; and R$^{1b}$ and R$^{1c}$ are each independently hydrogen or C$_{1-6}$ alkyl; and R$^2$ is heteroaryl, —O—C$_{1-6}$ alkyl, or —OCO—C$_{1-6}$ alkyl;

wherein each alkyl, aralkyl, and heteroaryl is optionally substituted with one or more, in one embodiment, one, two, three, or four, substituents Q; and wherein Q is as defined herein.

In still another embodiment, in any one of Formulae IX to XII,

R$^1$ is cyano, —CH$_2$OH, —CH$_2$NH$_2$, —COOH, —COOCH$_3$, 1,2,3-benzotriazol-1-yloxycarbonyl, benzyloxycarbonyl, —CONH$_2$, —CONHCH$_3$, —CONHCH$_2$CH$_3$, —CONHCH$_2$CH$_2$CH$_3$, —CON(CH$_3$)$_2$, —NH$_2$, or —NHC(O)NH$_2$; and R$^2$ is indol-3-yl, —OCH$_3$, —OCD$_3$, —OCH$_2$CH$_3$, or —OCOCH$_3$.

In certain embodiments, the compound of any one of Formulae I to XII is not methyl (2R,4aS,6aS,9S,12bR,14aS,14bR)-9-hydroxy-2,4a,6a,9,12b,14a-hexamethyl-10,11-di-oxo-1,2,3,4,4a,5,6,6a,9,10,11,12b,13,14,14a,14b-hexadeca-hydropicene-2-carboxylate.

In certain embodiments, in any one of Formulae I to XII, when R$^1$ is —COOCH$_3$, R$^2$ is not hydroxyl. In certain embodiments, in any one of Formulae I to XII, R$^2$ is not hydroxyl. In certain embodiments, in any one of Formulae I to XII, when R$^1$ is —COOCH$_3$, and R$^3$ and R$^4$ together with the carbon atom to which they are attached form ═CO, then R$^2$ is not hydroxyl. In certain embodiments, in any one of Formulae I to XII, when R$^1$ is —COOCH$_3$, and R$^5$ and R$^6$ together with the carbon atom to which they are attached form ═CO, then R$^2$ is not hydroxyl. In certain embodiments, in any one of Formulae I to XII, when R$^1$ is —COOCH$_3$, R$^3$ and R$^4$ together with the carbon atom to which they are attached form ═CO, and R$^5$ and R$^6$ together with the carbon atom to which they are attached form ═CO, then R$^2$ is not hydroxyl.

In yet another embodiment, provided herein is a compound of Formula (XIII):

(XIII)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein R$^{3a}$ is hydrogen, C$_{1-6}$ alkyl, —C(O)R$^{1a}$, —C(O)OR$^{1a}$, —C(O)ONR$^{1b}$R$^{1c}$, —C(O)SR$^{1a}$, —C(═NR$^{1a}$)NR$^{1b}$R$^{1c}$, —C(S)R$^{1a}$, —C(S)OR$^{1a}$, —C(S)NR$^{1b}$R$^{1c}$, —P(O)(OR$^{1a}$)OR$^{1d}$, —S(O)R$^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$; and wherein the alkyl is optionally substituted with one or more substituents Q; and R$^1$, R$^2$, R$^{1a}$, R$^{1b}$, R$^{1c}$, R$^{1d}$, and Q are each as defined herein.

In yet another embodiment, provided herein is a compound of Formula (XIV):

(XIV)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R$^1$, R$^2$, and R$^{3a}$ are each as defined herein.

In yet another embodiment, provided herein is a compound of Formula (XV):

(XV)

35 or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3a}$ are each as defined herein.

In yet another embodiment, provided herein is a compound of Formula (XVI):

(XVI)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3a}$ are each as defined herein.

In one embodiment, in any one of Formulae XIII to XVI, $R^1$ is (i) hydrogen, azido, cyano, halo, isocyanato, isothiocyanato, or nitro; (ii) $C_{1-6}$ alkyl, $C_{2-6}$ alkenyl, or $C_{2-6}$ alkynyl; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)NR$^{1b}$R$^{1c}$, —C(O)N($R^{1b}$)O$R^{1c}$, —C(=N$R^{1a}$)NR$^{1b}$R$^{1c}$, —O$R^{1a}$, —OC(O)$R^{1a}$, —OC(O)O$R^{1a}$, —OC(O)NR$^{1b}$R$^{1c}$, —OC(=N$R^{1ba}$)NR$^{1b}$R$^{1c}$, —OC(S)NR$^{1b}$R$^{1c}$, —OP(O)(O$R^{1a}$)O$R^{1d}$, —OS(O)$_2$R$^{1a}$, —OS(O)$_2$NR$^{1b}$R$^{1c}$, —NR$^{1b}$R$^{1c}$, —NR$^{1a}$C(O)$R^{1d}$, —NR$^{1a}$C(O)O$R^{1d}$, —NR$^{1a}$C(O)S$R^{1d}$, —NR$^{1a}$C(O)NR$^{1b}$R$^{1c}$, —NR$^{1a}$C(=N$R^{1d}$)$R^{1b}$, —NR$^{1a}$C(=N$R^{1d}$)NR$^{1b}$R$^{1c}$, —NR$^{1a}$S(O)$_2$R$^{1d}$, —NR$^{1a}$S(O)$_2$NR$^{1b}$R$^{1c}$, —SR$^{1a}$, —SC(O)$R^{1a}$, —SC(O)NR$^{1b}$R$^{1c}$, —S(O)$R^{1a}$, —S(O)$_2$R$^{1a}$, —S(O)$_2$O$R^{1a}$, or —S(O)$_2$NR$^{1b}$R$^{1c}$;

$R^2$ is heteroaryl, —O$R^{1a}$, or —OCO$R^{1a}$; and $R^{3a}$ is hydrogen, $C_{1-6}$ alkyl, —C(O)$R^{1a}$, —C(O)O$R^{1a}$, —C(O)ONR$^{1b}$R$^{1c}$, or —P(O)(O$R^{1a}$)O$R^{1d}$;

wherein each alkyl, alkenyl, alkynyl, and heteroaryl is optionally substituted with one or more, in one embodiment, one, two, three, or four, substituents Q; and wherein $R^{1a}$, $R^{1b}$, $R^{1c}$, $R^{1d}$, and Q are each as defined herein.

In another embodiment, in any one of Formulae XIII to XVI, $R^1$ is (i) hydrogen, azido, cyano, halo, isocyanato, isothiocyanato, or nitro; (ii) methyl, ethenyl, or ethynyl, each of which is optionally substituted with one or more, in one embodiment, one, two, three, or four, substituents Q; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)NR$^{1b}$R$^{1c}$, —C(O)N(H)O$R^{1c}$, —C(=N$R^{1a}$)NR$^{1b}$R$^{1c}$, —O$R^{1a}$, —OC(O)$R^{1a}$, —OC(O)O$R^{1a}$, —OC(O)NR$^{1b}$R$^{1c}$, —OC(=N$R^{1a}$)NR$^{1b}$R$^{1c}$, —OC(S)NR$^{1b}$R$^{1c}$, —OP(O)(O$R^{1a}$)O$R^{1d}$, —OS(O)$_2$R$^{1a}$, —OS(O)$_2$NR$^{1b}$R$^{1c}$, —NR$^{1b}$R$^{1c}$, —NR$^{1a}$C(O)$R^{1d}$, —NR$^{1a}$C(O)O$R^{1d}$, —NR$^{1a}$C(O)S$R^{1d}$, —NR$^{1a}$C(O)NR$^{1b}$R$^{1c}$, —NR$^{1a}$C(=N$R^{1d}$)$R^{1b}$, —NR$^{1a}$C(=N$R^{1d}$)NR$^{1b}$R$^{1c}$, —NR$^{1a}$S(O)$_2$R$^{1d}$, —NR$^{1a}$S(O)$_2$NR$^{1b}$R$^{1c}$,

36

—SR$^{1a}$, —SC(O)$R^{1a}$, —SC(O)NR$^{1b}$R$^{1c}$, —S(O)$R^{1a}$, —S(O)$_2$R$^{1a}$, —S(O)$_2$O$R^{1a}$, or —S(O)$_2$NR$^{1b}$R$^{1c}$;

$R^2$ is (i) heteroaryl, optionally substituted with one or more, in one embodiment, one, two, three, or four, substituents Q; or (ii) —O$R^{1a}$ or —OCO$R^{1a}$; and $R^{3a}$ is hydrogen, $C_{1-6}$ alkyl, —C(O)$R^{1a}$, —C(O)O$R^{1a}$, —C(O)ONR$^{1b}$R$^{1c}$, or —P(O)(O$R^{1a}$)O$R^{1d}$; wherein the alkyl is optionally substituted with one or more, in one embodiment, one, two, three, or four, substituents Q;

wherein $R^{1a}$, $R^{1b}$, $R^{1c}$, $R^{1d}$, and Q are each as defined herein.

In yet another embodiment, in any one of Formulae XIII to XVI, $R^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)NR$^b$R$^c$, —CH$_2$C(O)OP(O)(O$R^a$)O$R^d$, —CH$_2$C(O)S$R^a$, —CH$_2$O$R^a$, —CH$_2$OC(O)NR$^b$R$^c$, —CH$_2$OP(O)(O$R^a$)O$R^d$, —CH$_2$OS(O)$_2$R$^a$, —CH$_2$OS(O)$_2$O$R^a$, —CH$_2$NR$^b$R$^c$, —CH$_2$NR$^a$CO$R^d$, —CH$_2$NR$^a$C(O)O$R^d$, —CH$_2$NR$^a$C(O)NR$^b$R$^c$, —CH$_2$NR$^a$C(O)S$R^d$, —CH$_2$NR$^a$C(=N$R^d$)NR$^b$R$^c$, —CH$_2$NR$^a$S(O)$_2$R$^d$, —C(H)=CH$R^a$, or —C≡C—$R^a$; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)NR$^{1b}$R$^{1c}$, —C(O)N($R^{1a}$)O$R^{1c}$, —C(=N$R^{1a}$)NR$^{1b}$R$^{1c}$, —O$R^{1a}$, —OC(O)$R^{1a}$, —OC(O)O$R^{1a}$, —OC(O)NR$^{1b}$R$^{1c}$, —OC(=N$R^{1a}$)NR$^{1b}$R$^{1c}$, —OC(S)NR$^{1b}$R$^{1c}$, —OP(O)(O$R^{1a}$)O$R^{1d}$, —OS(O)$_2$R$^{1a}$, —OS(O)$_2$NR$^{1b}$R$^{1c}$, —NR$^{1b}$R$^{1c}$, —NR$^{1a}$C(O)$R^{1d}$, —NR$^{1a}$C(O)O$R^{1d}$, —NR$^{1a}$C(O)S$R^{1d}$, —NR$^{1a}$C(O)NR$^{1b}$R$^{1c}$, —NR$^{1a}$C(=N$R^{1d}$)$R^{1b}$, —NR$^{1a}$C(=N$R^{1d}$)NR$^{1b}$R$^{1c}$, —NR$^{1a}$S(O)$_2$R$^{1d}$, —NR$^{1a}$S(O)$_2$NR$^{1b}$R$^{1c}$, —SR$^{1a}$, —SC(O)$R^{1a}$, —SC(O)NR$^{1b}$R$^{1c}$, —S(O)$R^{1a}$, —S(O)$_2$R$^{1a}$, —S(O)$_2$O$R^{1a}$, or —S(O)$_2$NR$^{1b}$R$^{1c}$;

$R^2$ is heteroaryl, —O$R^{1a}$, or —OCO$R^{1a}$; and $R^{3a}$ is hydrogen, $C_{1-6}$ alkyl, —C(O)$R^{1a}$, —C(O)O$R^{1a}$, —C(O)ONR$^{1b}$R$^{1c}$, or —P(O)(O$R^{1a}$)O$R^{1d}$;

wherein each alkyl, aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae XIII to XVI, $R^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)NR$^b$R$^c$, —CH$_2$C(O)OP(O)(OH)O$R^a$, —CH$_2$C(O)S$R^a$, —CH$_2$O$R^a$, —CH$_2$OC(O)NR$^b$R$^c$, —CH$_2$OP(O)(OH)O$R^a$, —CH$_2$OS(O)$_2$R$^a$, —CH$_2$OS(O)$_2$O$R^a$, —CH$_2$NHR$^b$, —CH$_2$NHC(O)$R^d$, —CH$_2$NR$^a$C(O)O$R^d$, —CH$_2$NR$^a$C(O)NR$^b$R$^c$, —CH$_2$NR$^a$C(O)S$R^d$, —CH$_2$NHC(=N$R^d$)R$^b$R$^c$, —CH$_2$NHS(O)$_2$R$^d$, —C(H)=CH$R^a$, or —C≡C—$R^a$; or (iii) —C(H)=N$R^{1b}$, —C(H)=NO$R^{1b}$, —C(O)$R^{1a}$, —C(O)O$R^{1a}$, —C(O)N($R^{1b}$)CN, —C(O)NHR$^{1b}$, —C(O)N(H)O$R^{1c}$, —C(=N$R^{1a}$)NR$^{1b}$R$^{1c}$, —O$R^{1a}$, —OC(O)$R^{1a}$, —OC(O)O$R^{1a}$, —OC(O)NR$^{1b}$R$^{1c}$, —OC(=NH)NR$^{1b}$R$^{1c}$, —OC(S)NHR$^{1b}$, —OP(O)(OH)$R^{1a}$, —OP(O)(O$R^{1a}$)O$R^{1d}$, —OS(O)$_2$R$^{1a}$, —OS(O)$_2$NR$^{1b}$R$^{1c}$, —NHR$^{1b}$, —NHC(O)$R^{1d}$, —NR$^{1a}$C(O)O$R^{1d}$, —NHC(O)S$R^{1d}$, —NR$^{1a}$C(O)NR$^{1b}$R$^{1c}$, —NHC(=N$R^{1d}$)$R^{1b}$, —NHC(=N$R^{1d}$)R$^{1b}$R$^{1c}$, —NR$^{1a}$C(=NH)NR$^{1b}$R$^{1c}$, —NHS(O)$_2$R$^{1d}$, —NR$^{1a}$S(O)$_2$R$^{1d}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, or —S(O)$_2$NR$^{1b}$R$^{1c}$;

R$^2$ is heteroaryl, —OR$^{1a}$, or —OCOR$^{1a}$; and

R$^{3a}$ is hydrogen, C$_{1-6}$ alkyl, —C(O)R$^{1a}$, —C(O)OR$^{1a}$, —C(O)ONR$^{1b}$R$^{1c}$, or —P(O)(OR$^{1a}$)OR$^{1d}$;

wherein each alkyl, aryl, heteroaryl, and heterocyclyl is optionally substituted with one or more, in one embodiment, one, two, three, or four, substituents Q; and wherein R$^a$, R$^b$, R$^c$, R$^d$, R$^{1a}$, R$^{1b}$, R$^{1c}$, R$^{1d}$, and Q are each as defined herein.

In yet another embodiment, in any one of Formulae XIII to XVI,

R$^1$ is (i) hydrogen, azido, cyano, isocyanato, isothiocyanato, or nitro; (ii) —CH$_2$C(O)OPO(OH)$_2$, —CH$_2$OH, —CH$_2$OPO(OH)$_2$, —CH$_2$NH$_2$, morpholin-4-ylmethyl, piperazin-1-ylmethyl, or 4-methyl-piperazin-1-ylmethyl; (iii)

or (iv) —COH, —COOH, —C(O)OCH$_3$, —COOCH$_2$CH$_3$, 1,2,3-benzotriazol-1-yloxycarbonyl, benzyloxycarbonyl, pyrrolidin-1-ylcarbonyl, —CONH$_2$, —CONHCH$_3$, —CONHCH$_2$CH$_3$, —CONHCH$_2$CH$_2$CH$_3$, —CON(CH$_3$)$_2$, —CONHOH, —CONHCN, —OH, —OPO$_3$H$_2$, —NH$_2$, —NHCONH$_2$, —NHSO$_2$NH$_2$, —SH, —SO$_2$H, or —SO$_3$H;

R$^2$ is —OH, —OCH$_3$, —OCD$_3$, —OCH$_2$CH$_3$, —OCH$_2$CF$_3$, —OCOCH$_3$, or indolyl; and R$^{3a}$ is hydrogen, —COCH$_3$, —COCH$_2$CH$_3$, —COCH$_2$CH$_2$CH$_3$, —C(O)OCH$_2$CH$_3$, —C(O)ONHCH$_2$CH$_3$, —P(O)(OCH$_3$)$_2$, or —P(O)(OCH$_2$CH$_3$)$_2$.

In yet another embodiment, in any one of Formulae XIII to XVI,

R$^1$ is cyano, C$_{1-6}$ alkyl, —COOR$^{1a}$, —CONR$^{1b}$R$^{1c}$, —NR$^{1b}$R$^{1c}$, or —NR$^{1a}$C(O)NR$^{1b}$R$^{1c}$;

R$^2$ is heteroaryl, —OR$^{1a}$, or —OC(O)R$^{1a}$; and

R$^{3a}$ is hydrogen or —C(O)R$^{1a}$;

wherein the alkyl and heteroaryl are each optionally substituted with one or more, in one embodiment, one, two, three, or four, substituents Q; and wherein R$^{1a}$, R$^{1b}$, R$^{1c}$, and Q are each as defined herein.

In yet another embodiment, in any one of Formulae XIII to XVI,

R$^1$ is cyano, C$_{1-6}$ alkyl, —COOR$^{1a}$, —CONR$^{1b}$R$^{1c}$, —NR$^{1b}$R$^{1c}$, or —NR$^{1a}$C(O)NR$^{1b}$R$^{1c}$; wherein R$^{1a}$ is hydrogen, C$_{1-6}$ alkyl, C$_{7-15}$ aralkyl, or heteroaryl; and R$^{1b}$ and R$^{1c}$ are each independently hydrogen or C$_{1-6}$ alkyl;

R$^2$ is heteroaryl, —O—C$_{1-6}$ alkyl, or —OCO—C$_{1-6}$ alkyl; and

R$^{3a}$ is hydrogen or —CO—C$_{1-6}$ alkyl;

wherein each alkyl, aralkyl, and heteroaryl is optionally substituted with one or more, in one embodiment, one, two, three, or four, substituents Q; and wherein Q is as defined herein.

In still another embodiment, in any one of Formulae XIII to XVI,

R$^1$ is cyano, —CH$_2$OH, —CH$_2$NH$_2$, —CHO, —COOH, —COOCH$_3$, 1,2,3-benzotriazol-1-yloxycarbonyl, benzyloxycarbonyl, —CONH$_2$, —CONHCH$_3$, —CONHCH$_2$CH$_3$, —CONHCH$_2$CH$_2$CH$_3$, —CON(CH$_3$)$_2$, —NH$_2$, or —NHC(O)NH$_2$;

R$^2$ is —OCH$_3$, —OCD$_3$, —OCH$_2$CH$_3$, —OCOCH$_3$, or indol-3-yl; and

R$^{3a}$ is hydrogen or —COCH$_2$CH$_2$CH$_3$.

In yet another embodiment, provided herein is a compound of Formula (XIX):

(XIX)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein R$^{5a}$ is hydrogen, C$_{1-6}$ alkyl, —C(O)R$^{1a}$, —C(O)OR$^{1a}$, —C(O)ONR$^{1b}$R$^{1c}$, —C(O)SR$^{1a}$, —C(=NR$^{1a}$)NR$^{1b}$R$^{1c}$, —C(S)R$^{1a}$, —C(S)OR$^{1a}$, —C(S)NR$^{1b}$R$^{1c}$, —P(O)(OR$^{1a}$)OR$^{1d}$, —S(O)R$^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$;

wherein the alkyl is optionally substituted with one or more substituents Q; and R$^1$, R$^2$, R$^{1a}$, R$^{1b}$, R$^{1c}$, R$^{1d}$, R$^{3a}$, and Q are each as defined herein.

In yet another embodiment, provided herein is a compound of Formula (XX):

(XX)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^{3a}$, and $R^{5a}$ are each as defined herein.

In yet another embodiment, provided herein is a compound of Formula (XXI):

(XXI)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^{3a}$, and $R^{5a}$ are each as defined herein.

In yet another embodiment, provided herein is a compound of Formula (XXII):

(XXII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^{3a}$, and $R^{5a}$ are each as defined herein.

In one embodiment, in any one of Formulae XIX to XXII, $R^1$ is (i) hydrogen, azido, cyano, halo, isocyanato, isothiocyanato, or nitro; (ii) $C_{1\text{-}6}$ alkyl, $C_{2\text{-}6}$ alkenyl, or $C_{2\text{-}6}$ alkynyl; or (iii) —$C(R^{1a})$=$NR^{1b}$, —$C(R^{1a})$=$NOR^{1b}$, —$C(O)R^{1a}$, —$C(O)OR^{1a}$, —$C(O)N(R^{1b})CN$, —$C(O)NR^{1b}R^{1c}$, —$C(O)N(R^{1b})OR^{1c}$, —$C(=NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1ba})NR^{1b}R^{1c}$, —$OC(S)NR^{1b}R^{1c}$, —$OP(O)(OR^{1a})OR^{1d}$, —$OS(O)_2R^{1a}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)SR^{1d}$, —$NR^{1a}C(O)NR^{1b}R^{1c}$, —$NR^{1a}C(=NR^{1d})R^{1b}$, —$NR^{1a}C(=NR^{1d})NR^{1b}R^{1c}$, —$NR^{1a}S(O)_2R^{1d}$, —$NR^{1a}S(O)_2NR^{1b}R^{1c}$, —$SR^{1a}$, —$SC(O)R^{1a}$, —$SC(O)NR^{1b}R^{1c}$, —$S(O)R^{1a}$, —$S(O)_2R^a$, —$S(O)_2OR^{1a}$, or —$S(O)_2NR^{1b}R^{1c}$;

$R^2$ is heteroaryl, —$OR^{1a}$, or —$OCOR^{1a}$; and $R^{3a}$ and $R^{5a}$ are each independently hydrogen, $C_{1\text{-}6}$ alkyl, —$C(O)R^{1a}$, —$C(O)OR^{1a}$, —$C(O)ONR^{1b}R^{1c}$, or —$P(O)(OR^{1a})OR^{1d}$;

wherein each alkyl, alkenyl, alkynyl, and heteroaryl is optionally substituted with one or more, in one embodiment, one, two, three, or four, substituents Q; and wherein $R^{1a}$, $R^{1b}$, $R^{1c}$, $R^{1d}$, and Q are each as defined herein.

In another embodiment, in any one of Formulae XIX to XXII, $R^1$ is (i) hydrogen, azido, cyano, halo, isocyanato, isothiocyanato, or nitro; (ii) methyl, ethenyl, or ethynyl, each of which is optionally substituted with one or more, in one embodiment, one, two, three, or four, substituents Q; or (iii) —$C(R^{1a})$=$NR^{1b}$, —$C(R^{1a})$=$NOR^{1b}$, —$C(O)R^{1a}$, —$C(O)OR^{1a}$, —$C(O)N(R^{1b})CN$, —$C(O)NR^{1b}R^{1c}$, —$C(O)N(H)OR^{1c}$, —$C(=NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OC(S)NR^{1b}R^{1c}$, —$OP(O)(OR^{1a})OR^{1d}$, —$OS(O)_2R^{1a}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)SR^{1d}$, —$NR^{1a}C(O)NR^{1b}R^{1c}$, —$NR^{1a}C(=NR^{1d})R^{1b}$, —$NR^{1a}C(=NR^{1d})NR^{1b}R^{1c}$, —$NR^{1a}S(O)_2R^{1d}$, —$NR^{1a}S(O)_2NR^{1b}R^{1c}$, —$SR^{1a}$, —$SC(O)R^{1a}$, —$SC(O)NR^{1b}R^{1c}$, —$S(O)R^{1a}$, —$S(O)_2R^{1a}$, —$S(O)_2OR^{1a}$, or —$S(O)_2NR^{1b}R^{1c}$;

$R^2$ is (i) heteroaryl, optionally substituted with one or more, in one embodiment, one, two, three, or four, substituents Q; or (ii) —$OR^{1a}$ or —$OCOR^{1a}$; and $R^{3a}$ and $R^{5a}$ are each independently hydrogen, $C_{1\text{-}6}$ alkyl, —$C(O)R^{1a}$, —$C(O)OR^{1a}$, —$C(O)ONR^{1b}R^{1c}$, or —$P(O)(OR^{1a})OR^{1d}$; where the alkyl is optionally substituted with one or more, in one embodiment, one, two, three, or four, substituents Q;

wherein $R^{1a}$, $R^{1b}$, $R^{1c}$, $R^{1d}$, and Q are each as defined herein.

In yet another embodiment, in any one of Formulae XIX to XXII, $R^1$ is (i) hydrogen, azido, cyano, halo, isocyanato, isothiocyanato, or nitro; (ii) —$CH_2$—$C_{6\text{-}14}$ aryl, —$CH_2$-heteroaryl, —$CH_2$-heterocyclyl, —$CH_2C(O)NR^bR^c$, —$CH_2C(O)OP(O)(OR^a)OR^d$, —$CH_2C(O)SR^a$, —$CH_2OR^a$, —$CH_2OC(O)NR^bR^c$, —$CH_2OP(O)(OR^a)OR^d$, —$CH_2OS(O)_2R^a$, —$CH_2OS(O)_2OR^a$, —$CH_2NR^bR^c$, —$CH_2NR^aCOR^d$, —$CH_2NR^aC(O)OR^d$, —$CH_2NR^aC(O)NR^bR^c$, —$CH_2NR^aC(O)SR^d$, —$CH_2NR^aC(=NR^d)R^bR^c$, —$CH_2NR^aS(O)_2R^d$, —$C(H)$=$CHR^a$, or —$C$≡$C$—$R^a$; or (iii) —$C(R^{1a})$=$NR^{1b}$, —$C(R^{1a})$=$NOR^{1b}$, —$C(O)R^{1a}$, —$C(O)OR^{1a}$, —$C(O)N(R^{1b})CN$, —$C(O)NR^{1b}R^{1c}$, —$C(O)N(R^{1a})OR^{1c}$, —$C(=NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OC(S)NR^{1b}R^{1c}$, —$OP(O)(OR^{1a})OR^{1d}$, —$OS(O)_2R^{1a}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)SR^{1d}$, —$NR^{1a}C(O)NR^{1b}R^{1c}$, —$NR^{1a}C(=NR^{1d})R^{1b}$, —$NR^{1a}C(=NR^{1d})NR^{1b}R^{1c}$, —$NR^{1a}S(O)_2R^{1d}$, —$NR^{1a}S(O)_2NR^{1b}R^{1c}$, —$SR^{1a}$, —$SC(O)R^{1a}$, —$SC(O)NR^{1b}R^{1c}$, —$S(O)R^{1a}$, —$S(O)_2R^{1a}$, —$S(O)_2OR^{1a}$, or —$S(O)_2NR^{1b}R^{1c}$;

$R^2$ is heteroaryl, —$OR^{1a}$, or —$OCOR^{1a}$; and $R^{3a}$ and $R^{5a}$ are each independently hydrogen, $C_{1\text{-}6}$ alkyl, —$C(O)R^{1a}$, —$C(O)OR^{1a}$, —$C(O)ONR^{1b}R^{1c}$, or —$P(O)(OR^{1a})OR^{1d}$;

wherein each alkyl, aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae XIX to XXII, $R^1$ is (i) hydrogen, azido, cyano, halo, isocyanato, isothiocyanato, or nitro; (ii) —$CH_2$—$C_{6-14}$ aryl, —$CH_2$-heteroaryl, —$CH_2$-heterocyclyl, —$CH_2C(O)NR^bR^c$, —$CH_2C(O)OP(O)(OH)OR^a$, —$CH_2C(O)SR^a$, —$CH_2OR^a$, —$CH_2OC(O)NR^bR^c$, —$CH_2OP(O)(OH)OR^a$, —$CH_2OS(O)_2R^a$, —$CH_2OS(O)_2OR^a$, —$CH_2NHR^b$, —$CH_2NHC(O)R^d$, —$CH_2NR^aC(O)OR^d$, —$CH_2NR^aC(O)NR^bR^c$, —$CH_2NR^aC(O)SR^d$, —$CH_2NHC(=NR^d)^bR^c$, —$CH_2NHS(O)_2R^d$, —$C(H)=CHR^a$, or —$C\equiv C$—$R^a$; or (iii) —$C(H)=NR^{1b}$, —$C(H)=NOR^{1b}$, —$C(O)R^{1a}$, —$C(O)OR^{1a}$, —$C(O)N(R^{1b})CN$, —$C(O)NHR^{1b}$, —$C(O)N(H)OR^{1c}$, —$C(=NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NH)NR^{1b}R^{1c}$, —$OC(S)NHR^{1b}$, —$OP(O)(OH)R^{1a}$, —$OP(O)(OR^{1a})OR^{1d}$, —$OS(O)_2R^{1a}$, —$OS(O)_2NR^{1b}R^{1c}$, —$NHR^{1b}$, —$NHC(O)R^{1d}$, —$NR^{1a}C(O)OR^{1d}$, —$NHC(O)SR^{1d}$, —$NR^{1a}C(O)NR^{1b}R^{1c}$, —$NHC(=NR^{1d})R^{1b}$, —$NHC(=NR^{1d})NR^{1b}R^{1c}$, —$NR^{1a}C(=NH)NR^{1b}R^{1c}$, —$NHS(O)_2R^{1d}$, —$NR^{1a}S(O)_2R^{1d}$, —$NR^{1a}S(O)_2NR^{1b}R^{1c}$, —$SR^{1a}$, —$SC(O)R^{1a}$, —$SC(O)NR^{1b}R^{1c}$, —$S(O)R^{1a}$, —$S(O)_2R^{1a}$, —$S(O)_2OR^{1a}$, or —$S(O)_2NR^{1b}R^{1c}$;

$R^2$ is heteroaryl, —$OR^{1a}$, or —$OCOR^{1a}$; and $R^{3a}$ and $R^{5a}$ are each independently hydrogen, $C_{1-6}$ alkyl, —$C(O)R^{1a}$, —$C(O)OR^{1a}$, —$C(O)ONR^{1b}R^{1c}$, or —$P(O)(OR^{1a})OR^{1d}$;

wherein each alkyl, aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae XIX to XXII, $R^1$ is (i) hydrogen, azido, cyano, isocyanato, isothiocyanato, or nitro; (ii) —$CH_2C(O)OPO(OH)_2$, —$CH_2OH$, —$CH_2OPO(OH)_2$, —$CH_2NH_2$, morpholin-4-ylmethyl, piperazin-1-ylmethyl, or 4-methyl-piperazin-1-ylmethyl; (iii)

(structures)

or (iv) —COH, —COOH, —$C(O)OCH_3$, —$COOCH_2CH_3$, 1,2,3-benzotriazol-1-yloxycarbonyl, benzyloxycarbonyl, pyrrolidin-1-ylcarbonyl, —$CONH_2$, —$CONHCH_3$, —$CONHCH_2CH_3$, —$CONHCH_2CH_2CH_3$, —$CON(CH_3)_2$, —CONHOH, —CONHCN, —OH, —$OPO_3H_2$, —$NH_2$, —$NHCONH_2$, —$NHSO_2NH_2$, —SH, —$SO_2H$, or —$SO_3H$;

$R^2$ is —OH, —$OCH_3$, —$OCD_3$, —$OCH_2CH_3$, —$OCH_2CF_3$, —$OCOCH_3$, or indolyl; and $R^{3a}$ and $R^{5a}$ are each independently hydrogen, —$COCH_3$, —$COCH_2CH_3$, —$COCH_2CH_2CH_3$, —$C(O)OCH_2CH_3$, —$C(O)ONHCH_2CH_3$, —$P(O)(OCH_3)_2$, or —$P(O)(OCH_2CH_3)_2$.

In yet another embodiment, in any one of Formulae XIX to XXII, $R^1$ is cyano, $C_{1-6}$ alkyl, —$COOR^{1a}$, —$CONR^{1b}R^{1c}$, —$NR^{1b}R^{1c}$, or —$NR^{1a}C(O)NR^{1b}R^{1c}$;

$R^2$ is heteroaryl, —$OR^{1a}$, or —$OC(O)R^{1a}$; and $R^{3a}$ and $R^{5a}$ are each independently hydrogen or —$C(O)R^{1a}$;

wherein the alkyl and heteroaryl are each optionally substituted with one or more, in one embodiment, one, two, three, or four, substituents Q; and wherein $R^{1a}$, $R^{1b}$, $R^{1c}$, and Q are each as defined herein.

In yet another embodiment, in any one of Formulae XIX to XXII, $R^1$ is cyano, $C_{1-6}$ alkyl, —$COOR^{1a}$, or —$CONR^{1b}R^{1c}$, —$NR^{1b}R^{1c}$, or —$NR^{1a}C(O)NR^{1b}R^{1c}$; wherein $R^{1a}$ is hydrogen, $C_{1-6}$ alkyl, $C_{7-15}$ aralkyl, or heteroaryl; and $R^{1b}$ and $R^{1c}$ are each independently hydrogen or $C_{1-6}$ alkyl;

$R^2$ is heteroaryl, —O—$C_{1-6}$ alkyl, or —OCO—$C_{1-6}$ alkyl; and $R^{3a}$ and $R^{5a}$ are each independently hydrogen or —CO—$C_{1-6}$ alkyl;

wherein each alkyl, aralkyl, and heteroaryl is optionally substituted with one or more, in one embodiment, one, two, three, or four, substituents Q; and wherein Q is as defined herein.

In still another embodiment, in any one of Formulae XIX to XXII, $R^1$ is cyano, —$CH_2OH$, —$CH_2NH_2$, —CHO, —COOH, —$COOCH_3$, 1,2,3-benzotriazol-1-yloxycarbonyl, benzyloxycarbonyl, —$CONH_2$, —$CONHCH_3$, —$CONHCH_2CH_3$, —$CONHCH_2CH_2CH_3$, —$CON(CH_3)_2$, —$NH_2$, or —$NHC(O)NH_2$;

$R^2$ is —$OCH_3$, —$OCD_3$, —$OCH_2CH_3$, —$OCOCH_3$, or indol-3-yl; and $R^{3a}$ and $R^{5a}$ are each independently hydrogen or —$COCH_2CH_2CH_3$.

In yet another embodiment, provided herein is a compound of Formula (XXIII):

(XXIII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^{3b}$ is (i)

hydrogen or deuterium; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and $R^1$, $R^2$, and Q are each as defined herein.

In one embodiment, provided herein is a compound of Formula (XXIIIa):

(XXIIIa)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In another embodiment, provided herein is a compound of Formula (XXIIIb):

(XXIIIb)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In yet another embodiment, provided herein is a compound of Formula (XXIV):

(XXIV)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In one embodiment, provided herein is a compound of Formula (XXIVa):

(XXIVa)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In another embodiment, provided herein is a compound of Formula (XXIVb):

(XXIVb)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In yet another embodiment, provided herein is a compound of Formula (XXV):

(XXV)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In one embodiment, provided herein is a compound of Formula (XXVa):

(XXVa)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In another embodiment, provided herein is a compound of Formula (XXVb):

(XXVb)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In yet another embodiment, provided herein is a compound of Formula (XXVI):

(XXVI)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In one embodiment, provided herein is a compound of Formula (XXVIa):

(XXVIa)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In another embodiment, provided herein is a compound of Formula (XXVIb):

(XXVIb)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^{3b}$ are each as defined herein.

In one embodiment, in any one of Formulae XXIII to XXVI, XXIIIa to XXVIa, and XXIIIb to XXVIb, $R^1$ is (i) hydrogen, azido, cyano, halo, isocyanato, isothiocyanato, or nitro; (ii) $C_{1-6}$ alkyl, $C_{2-6}$ alkenyl, or $C_{2-6}$ alkynyl; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)NR$^{1b}$R$^{1c}$, —C(O)N($R^{1b}$)O$R^{1c}$, —C(=N$R^{1a}$)NR$^{1b}$R$^{1c}$, —O$R^{1a}$, —OC(O)$R^{1a}$, —OC(O)O$R^{1a}$, —OC(O)NR$^{1b}$R$^{1c}$, —OC(=N$R^{1ba}$)NR$^{1b}$R$^{1c}$, —OC(S)NR$^{1b}$R$^{1c}$, —OP(O)(O$R^{1a}$)O$R^{1d}$, —OS(O)$_2$R$^{1a}$, —OS(O)$_2$NR$^{1b}$R$^{1c}$, —NR$^{1b}$R$^{1c}$, —N$R^{1a}$C(O)$R^{1d}$, —N$R^{1a}$C(O)O$R^{1d}$, —N$R^{1a}$C(O)S$R^{1d}$, —N$R^{1a}$C(O)NR$^{1b}$R$^{1c}$, —N$R^{1a}$C(=N$R^{1d}$)$R^{1b}$, —N$R^{1a}$C(=N$R^{1d}$)NR$^{1b}$R$^{1c}$, —N$R^{1a}$S(O)$_2$R$^{1d}$, —N$R^{1a}$S(O)$_2$NR$^{1b}$R$^{1c}$, —S$R^{1a}$, —SC(O)$R^{1a}$, —SC(O)NR$^{1b}$R$^{1c}$, —S(O)$R^{1a}$, —S(O)$_2$R$^a$, —S(O)$_2$O$R^{1a}$, or —S(O)$_2$NR$^{1b}$R$^{1c}$;

$R^2$ is heteroaryl, —O$R^{1a}$, or —OCOR$^{1a}$; and $R^{3b}$ is (i) hydrogen or deuterium; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

wherein each alkyl, alkenyl, alkynyl, and heteroaryl is optionally substituted with one or more, in one embodiment, one, two, three, or four, substituents Q; and wherein $R^{1a}$, $R^{1b}$, $R^{1c}$, $R^{1d}$, and Q are each as defined herein.

In another embodiment, in any one of Formulae XXIII to XXVI, XXIIIa to XXVIa, and XXIIIb to XXVIb, $R^1$ is (i) hydrogen, azido, cyano, halo, isocyanato, isothiocyanato, or nitro; (ii) methyl, ethenyl, or ethynyl, each of which is optionally substituted with one or more, in one embodiment, one, two, three, or four, substituents Q; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)NR$^{1b}$R$^{1c}$, —C(O)N(H)O$R^{1c}$, —C(=N$R^{1a}$)NR$^{1b}$R$^{1c}$, —O$R^{1a}$, —OC(O)$R^{1a}$, —OC(O)O$R^{1a}$, —OC(O)NR$^{1b}$R$^{1c}$, —OC(=N$R^{1a}$)NR$^{1b}$R$^{1c}$, —OC(S)NR$^{1b}$R$^{1c}$, —OP(O)(O$R^{1a}$)O$R^{1d}$, —OS(O)$_2$R$^{1a}$, —OS(O)$_2$NR$^{1b}$R$^{1c}$, —NR$^{1b}$R$^{1c}$, —N$R^{1a}$C(O)$R^{1d}$, —N$R^{1a}$C(O)O$R^{1d}$, —N$R^{1a}$C(O)S$R^{1d}$, —N$R^{1a}$C(O)NR$^{1b}$R$^{1c}$, —N$R^{1a}$C(=N$R^{1d}$)$R^{1b}$, —N$R^{1a}$C(=N$R^{1d}$)NR$^{1b}$R$^{1c}$, —N$R^{1a}$S(O)$_2$R$^{1d}$, —N$R^{1a}$S(O)$_2$ NR$^{1b}$R$^{1c}$, —S$R^{1a}$, —SC(O)$R^{1a}$, —SC(O)NR$^{1b}$R$^{1c}$, —S(O)$R^{1a}$, —S(O)$_2$R$^{1a}$, —S(O)$_2$O$R^{1a}$, or —S(O)$_2$ NR$^{1b}$R$^{1c}$;

$R^2$ is (i) heteroaryl, optionally substituted with one or more, in one embodiment, one, two, three, or four, substituents Q; or (ii) —O$R^{1a}$ or —OCOR$^{1a}$; and $R^{3b}$ is (i) hydrogen or deuterium; or (ii) $C_{1-6}$ alkyl, optionally substituted with one or more, in one embodiment, one, two, three, or four, substituents Q;

wherein $R^{1a}$, $R^{1b}$, $R^{1c}$, $R^{1d}$, and Q are each as defined herein.

In yet another embodiment, in any one of Formulae XXIII to XXVI, XXIIIa to XXVIa, and XXIIIb to XXVIb, $R^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)NR$^b$R$^c$, —CH$_2$C(O)OP(O)(OR$^a$)OR$^d$, —CH$_2$C(O)SR$^a$, —CH$_2$OR$^a$, —CH$_2$OC(O)NR$^b$R$^c$, —CH$_2$OP(O)(OR$^a$) OR$^d$, —CH$_2$OS(O)$_2$R$^a$, —CH$_2$OS(O)$_2$OR$^a$, —CH$_2$NR$^b$R$^c$, —CH$_2$NR$^a$COR$^d$, —CH$_2$NR$^a$C(O) OR$^d$, —CH$_2$NR$^a$C(O)NR$^b$R$^c$, —CH$_2$NR$^a$C(O)SR$^d$, —CH$_2$NR$^a$C(=NR$^d$)R$^b$R$^c$, —CH$_2$NR$^a$S(O)$_2$R$^d$, —C(H)=CHR$^a$, or —C≡C—R$^a$; or (iii) —C($R^{1a}$)=N$R^{1b}$, —C($R^{1a}$)=NO$R^{1b}$, —C(O)$R^{1a}$, —C(O)O$R^{1a}$, —C(O)N($R^{1b}$)CN, —C(O)NR$^{1b}$R$^{1c}$, —C(O)N($R^{1a}$)O$R^{1c}$, —C(=N$R^{1a}$)NR$^{1b}$R$^{1c}$, —O$R^{1a}$, —OC(O) $R^{1a}$, —OC(O)O$R^{1a}$, —OC(O)NR$^{1b}$R$^{1c}$, —OC(=N$R^{1a}$)NR$^{1b}$R$^{1c}$, —OC(S)NR$^{1b}$R$^{1c}$, —OP(O)(O$R^{1a}$) O$R^{1d}$, —OS(O)$_2$R$^{1a}$, —OS(O)$_2$NR$^{1b}$R$^{1c}$, —NR$^{1b}$R$^{1c}$, —N$R^{1a}$C(O)$R^{1d}$, —N$R^{1a}$C(O)O$R^{1d}$, —N$R^{1a}$C(O) S$R^{1d}$, —N$R^{1a}$C(O)NR$^{1b}$R$^{1c}$, —N$R^{1a}$C(=N$R^{1d}$)$R^{1b}$, —N$R^{1a}$C(=N$R^{1d}$)NR$^{1b}$R$^{1c}$, —N$R^{1a}$S(O)$_2$R$^{1d}$, —N$R^{1a}$S(O)$_2$NR$^{1b}$R$^{1c}$, —S$R^{1a}$, —SC(O)$R^{1a}$, —SC (O)NR$^{1b}$R$^{1c}$, —S(O)$R^{1a}$, —S(O)$_2$R$^a$, —S(O)$_2$O$R^{1a}$, or —S(O)$_2$NR$^{1b}$R$^{1c}$; and $R^2$ is heteroaryl, —O$R^{1a}$, or —OCOR$^{1a}$; and $R^{3b}$ is hydrogen, deuterium, or $C_{1-6}$ alkyl;

wherein each alkyl, aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae XXIII to XXVI, XXIIIa to XXVIa, and XXIIIb to XXVIb, $R^1$ is (i) hydrogen, azido, cyano, halo, isocyanato, isothiocyanato, or nitro; (ii) —CH$_2$—C$_{6-14}$ aryl, —CH$_2$-heteroaryl, —CH$_2$-heterocyclyl, —CH$_2$C(O)NR$^b$R$^c$, —CH$_2$C(O)OP(O)(OH)OR$^a$, —CH$_2$C(O)SR$^a$, —CH$_2$OR$^a$, —CH$_2$OC(O)NR$^b$R$^c$, —CH$_2$OP(O)(OH) OR$^a$, —CH$_2$OS(O)$_2$R$^a$, —CH$_2$OS(O)$_2$OR$^a$, —CH$_2$NHR$^b$, —CH$_2$NHC(O)R$^d$, —CH$_2$NR$^a$C(O) OR$^d$, —CH$_2$NR$^a$C(O)NR$^b$R$^c$, —CH$_2$NR$^a$C(O)SR$^d$, —CH$_2$NHC(=NR$^d$)NR$^b$R$^c$, —CH$_2$NHS(O)$_2$R$^d$, —C(H)=CHR$^a$, or —C≡C—R$^a$; or (iii) —C(H)=N$R^{1b}$, —C(H)=NO$R^{1b}$, —C(O)$R^{1a}$, —C(O)O$R^{1a}$, —C(O)N($R^{1b}$)CN, —C(O)NHR$^{1b}$, —C(O)N(H)O$R^{1c}$, —C(=N$R^{1a}$)NR$^{1b}$R$^{1c}$, —O$R^{1a}$, —OC(O)$R^{1a}$, —OC (O)O$R^{1a}$, —OC(O)NR$^{1b}$R$^{1c}$, —OC(=NH)NR$^{1b}$R$^{1c}$, —OC(S)NHR$^{1b}$, —OP(O)(OH)R$^{1a}$, —OP(O)(O$R^{1a}$) O$R^{1d}$, —OS(O)$_2$R$^{1a}$, —OS(O)$_2$NR$^{1b}$R$^{1c}$, —NHR$^{1b}$, —NHC(O)R$^{1d}$, —N$R^{1a}$C(O)O$R^{1d}$, —NHC(O)SR$^{1d}$, —N$R^{1a}$C(O)NR$^{1b}$R$^{1c}$, —NHC(=N$R^{1d}$)R$^{1b}$, —NHC (=N$R^{1d}$)NR$^{1b}$R$^{1c}$, —N$R^{1a}$C(=NH)NR$^{1b}$R$^{1c}$, —NHS (O)$_2$R$^{1d}$, —N$R^{1a}$S(O)$_2$R$^{1d}$, —N$R^{1a}$S(O)$_2$NR$^{1b}$R$^{1c}$, —SR$^{1a}$, —SC(O)$R^{1a}$, —SC(O)NR$^{1b}$R$^{1c}$, —S(O)$R^{1a}$, —S(O)$_2$R$^{1a}$, —S(O)$_2$O$R^{1a}$, or —S(O)$_2$NR$^{1b}$R$^{1c}$;

$R^2$ is heteroaryl, —O$R^{1a}$, or —OCOR$^{1a}$; and $R^{3b}$ is hydrogen, deuterium, or $C_{1-6}$ alkyl;

wherein each alkyl, aryl, heteroaryl, and heterocyclyl is optionally substituted with one or more, in one embodiment, one, two, three, or four, substituents Q; and wherein $R^a$, $R^b$, $R^c$, $R^d$, $R^{1a}$, $R^{1b}$, $R^{1c}$, $R^{1d}$, and Q are each as defined herein.

In yet another embodiment, in any one of Formulae XXIII to XXVI, XXIIIa to XXVIa, and XXIIIb to XXVIb, $R^1$ is (i) hydrogen, azido, cyano, isocyanato, isothiocyanato, or nitro; (ii) —CH$_2$C(O)OPO(OH)$_2$, —CH$_2$OH, —CH$_2$OPO(OH)$_2$, —CH$_2$NH$_2$, morpholin-4-ylmethyl, piperazin-1-ylmethyl, or 4-methyl-piperazin-1-ylmethyl; (iii)

-continued or (iv) —COH, —COOH, —C(O)OCH₃, —COOCH₂CH₃,
1,2,3-benzotriazol-1-yloxycarbonyl, benzyloxycarbonyl,
pyrrolidin-1-ylcarbonyl, —CONH₂, —CONHCH₃,
—CONHCH₂CH₃, —CONHCH₂CH₂CH₃, —CON(CH₃)₂,
—CONHOH, —CONHCN, —OH, —OPO₃H₂, —NH₂,
—NHCONH₂, —NHSO₂NH₂, —SH, —SO₂H, or —SO₃H;

R² is indolyl, —OH, —OCH₃, —OCD₃, —OCH₂CH₃, —OCH₂CF₃, or —OCOCH₃; and

R³ᵇ is hydrogen or deuterium.

In yet another embodiment, in any one of Formulae XXIII to XXVI, XXIIIa to XXVIa, and XXIIIb to XXVIb, R¹ is cyano, $C_{1-6}$ alkyl, —COOR¹ᵃ, —CONR¹ᵇR¹ᶜ, —NR¹ᵇR¹ᶜ, or —NR¹ᵃC(O)NR¹ᵇR¹ᶜ;

R² is heteroaryl, —OR¹ᵃ, or —OC(O)R¹ᵃ; and

R³ᵇ is hydrogen, deuterium, or $C_{1-6}$ alkyl;

wherein each alkyl and heteroaryl is optionally substituted with one or more, in one embodiment, one, two, three, or four, substituents Q; and wherein R¹ᵃ, R¹ᵇ, R¹ᶜ, and Q are each as defined herein.

In yet another embodiment, in any one of Formulae XXIII to XXVI, XXIIIa to XXVIa, and XXIIIb to XXVIb, R¹ is cyano, $C_{1-6}$ alkyl, —COOR¹ᵃ, —CONR¹ᵇR¹ᶜ, —NR¹ᵇR¹ᶜ, or —NR¹ᵃC(O)NR¹ᵇR¹ᶜ; wherein R¹ᵃ is hydrogen, $C_{1-6}$ alkyl, $C_{7-15}$ aralkyl, or heteroaryl; and R¹ᵇ and R¹ᶜ are each independently hydrogen or $C_{1-6}$ alkyl;

R² is heteroaryl, —O—$C_{1-6}$ alkyl, or —OCO—$C_{1-6}$ alkyl; and

R³ᵇ is hydrogen, deuterium, or $C_{1-6}$ alkyl;

wherein each alkyl, aralkyl, and heteroaryl is optionally substituted with one or more, in one embodiment, one, two, three, or four, substituents Q; and wherein Q is as defined herein.

In still another embodiment, in any one of Formulae XXIII to XXVI, XXIIIa to XXVIa, and XXIIIb to XXVIb, R¹ is cyano, —CH₂OH, —CH₂NH₂, —COOH, —COOCH₃, 1,2,3-benzotriazol-1-yloxycarbonyl, benzyloxycarbonyl, —CONH₂, —CONHCH₃, —CONHCH₂CH₃, —CONHCH₂CH₂CH₃, —CON(CH₃)₂, —NH₂, or —NHC(O)NH₂;

R² is indol-3-yl, —OCH₃, —OCD₃, —OCH₂CH₃, or —OCOCH₃; and

R³ᵇ is hydrogen or deuterium.

In yet another embodiment, provided herein is a compound of Formula (XXVII):

(XXVII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R¹, R², and R⁶ are each as defined herein.

In yet another embodiment, provided herein is a compound of Formula (XXVIII):

(XXVIII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R¹, R², and R⁶ are each as defined herein.

In yet another embodiment, provided herein is a compound of Formula (XXIX):

(XXIX)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^6$ are each as defined herein.

In still another embodiment, provided herein is a compound of Formula (XXX):

(XXX)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, and $R^6$ are each as defined herein.

The groups, $R^1$, $R^2$, $R^3$, $R^4$, $R^5$, $R^6$, $R^{3a}$, $R^{3b}$, and $R^{5a}$, in formulae described herein, including Formulae I to XXX, XXIIIa to XXVIa, and XXIIIb to XXVIb, are further defined in the embodiments described herein. All combinations of the embodiments provided herein for such groups are within the scope of this disclosure.

In certain embodiments, $R^1$ is hydrogen. In certain embodiments, $R^1$ is deuterium. In certain embodiments, $R^1$ is azido. In certain embodiments, $R^1$ is cyano. In certain embodiments, $R^1$ is halo. In certain embodiments, $R^1$ is isocyanate. In certain embodiments, $R^1$ is isothiocyanato. In certain embodiments, $R^1$ is nitro. In certain embodiments, $R^1$ is $C_{1-6}$ alkyl, optionally substituted with one or more substituents Q. In certain embodiments, $R^1$ is methyl, optionally substituted with one or more substituents Q. In certain embodiments, $R^1$ is —CH$_2$OH. In certain embodiments, $R^1$ is —CH$_2$NH$_2$. In certain embodiments, $R^1$ is $C_{2-6}$ alkenyl, optionally substituted with one or more substituents Q. In certain embodiments, $R^1$ is $C_{2-6}$ alkynyl, optionally substituted with one or more substituents Q. In certain embodiments, $R^1$ is $C_{3-10}$ cycloalkyl, optionally substituted with one or more substituents Q. In certain embodiments, $R^1$ is $C_{6-14}$ aryl, optionally substituted with one or more substituents Q. In certain embodiments, $R^1$ is $C_{7-15}$ aralkyl, optionally substituted with one or more substituents Q. In certain embodiments, $R^1$ is heteroaryl, optionally substituted with one or more substituents Q. In certain embodiments, $R^1$ is heterocyclyl, optionally substituted with one or more substituents Q.

In certain embodiments, $R^1$ is —C($R^{1a}$)=N$R^{1b}$, wherein $R^{1a}$ and $R^{1b}$ are each as defined herein. In certain embodiments, $R^1$ is —C($R^{1a}$)=NO$R^{1b}$, wherein $R^{1a}$ and $R^{1b}$ are each as defined herein. In certain embodiments, $R^1$ is —C(O)$R^{1a}$, wherein $R^{1a}$ is as defined herein. In certain embodiments, $R^1$ is —CHO. In certain embodiments, $R^1$ is —C(O)O$R^{1a}$, wherein $R^{1a}$ is as defined herein. In certain embodiments, $R^1$ is —C(O)O—$C_{1-6}$ alkyl, optionally substituted with one or more substituents Q. In certain embodiments, $R^1$ is —C(O)O—$C_{7-15}$ aralkyl, optionally substituted with one or more substituents Q. In certain embodiments, $R^1$ is —C(O)OH, —C(O)OCH$_3$, or —C(O)OCH$_2$Ph. In certain embodiments, $R^1$ is —C(O)O— heterocyclyl, optionally substituted with one or more substituents Q. In certain embodiments, $R^1$ is —C(O)O-monocyclic heterocyclyl, optionally substituted with one or more substituents Q. In certain embodiments, $R^1$ is morpholin-4-ylcarbonyl, optionally substituted with one or more substituents Q. In certain embodiments, $R^1$ is —C(O)ON$R^{1b}R^{1c}$, wherein $R^{1b}$ and $R^{1c}$ are each as defined herein. In certain embodiments, $R^1$ is —C(O)N(CN)$R^{1b}$, wherein $R^{1b}$ is as defined herein. In certain embodiments, $R^1$ is —C(O)N$R^{1b}R^{1c}$, wherein $R^{1b}$ and $R^{1c}$ are each as defined herein. In certain embodiments, $R^1$ is —C(O)N$R^{1b}R^{1c}$, wherein $R^{1b}$ and $R^{1c}$ are each independently hydrogen or $C_{1-6}$ alkyl, optionally substituted with one or more substituents Q. In certain embodiments, $R^1$ is —C(O)NH$_2$, —C(O)NHCH$_3$, —C(O)NHCH$_2$CH$_3$, —C(O)NHCH$_2$CH$_2$CH$_3$, or —C(O)N(CH$_3$)$_2$. In certain embodiments, $R^1$ is —C(O)NH$_2$, —C(O)NHCH$_3$, —C(O)NHCH$_2$CH$_3$, —C(O)NHCH$_2$CH$_2$OH, —C(O)NHCH$_2$CH$_2$CH$_3$, or —C(O)N(CH$_3$)$_2$. In certain embodiments, $R^1$ is —C(O)N($R^{1b}$)O$R^{1c}$, wherein $R^{1b}$ and $R^{1c}$ are each as defined herein. In certain embodiments, $R^1$ is —C(O)NHOH. In certain embodiments, $R^1$ is —C(O)S$R^{1a}$, wherein $R^{1a}$ is as defined herein. In certain embodiments, $R^1$ is —C(=N$R^{1a}$)N$R^{1b}R^{1c}$, wherein $R^{1a}$, $R^{1b}$, and $R^{1c}$ are each as defined herein. In certain embodiments, $R^1$ is —C(S)$R^{1a}$, wherein $R^{1a}$ is as defined herein. In certain embodiments, $R^1$ is —C(S)O$R^{1a}$, wherein $R^{1a}$ is as defined herein. In certain embodiments, $R^1$ is —C(S)N$R^{1b}R^{1c}$, wherein $R^{1b}$ and $R^{1c}$ are each as defined herein. In certain embodiments, $R^1$ is —O$R^{1a}$, wherein $R^{1a}$ is as defined herein. In certain embodiments, $R^1$ is —OC(O)$R^{1a}$, wherein $R^{1a}$ is as defined herein. In certain embodiments, $R^1$ is —OC(O)O$R^{1a}$, wherein $R^{1a}$ is as defined herein. In certain embodiments, $R^1$ is —OC(O)N$R^{1b}R^{1c}$, wherein $R^{1b}$ and $R^{1c}$ are each as defined herein. In certain embodiments, $R^1$ is —OC(O)S$R^{1a}$, wherein $R^{1a}$ is as defined herein. In certain embodiments, $R^1$ is —OC(=N$R^{1a}$)N$R^{1b}R^{1c}$, wherein $R^{1a}$, $R^{1b}$, and $R^{1c}$ are each as defined herein. In certain embodiments, $R^1$ is —OC(S)$R^{1a}$, wherein $R^a$ is as defined herein. In certain embodiments, $R^1$ is —OC(S)O$R^{1a}$, wherein $R^{1a}$ is as defined herein. In certain embodiments, $R^1$ is —OC(S)N$R^{1b}R^{1c}$, wherein $R^{1b}$ and $R^{1c}$ are each as defined herein. In certain embodiments, $R^1$ is —OP(O)(O$R^{1a}$)O$R^{1d}$, wherein $R^{1a}$ and $R^{1d}$ are each as defined herein. In certain embodiments, $R^1$ is —OS(O)$R^{1a}$, wherein $R^{1a}$ is as defined herein. In certain embodiments, $R^1$ is —OS(O)$_2R^{1a}$, wherein $R^{1a}$ is as defined herein. In certain embodiments, $R^1$ is —OS(O)$_2$O$R^{1a}$, wherein $R^{1a}$ is as defined herein. In certain embodiments, $R^1$ is —OS(O)N$R^{1b}R^{1c}$, wherein $R^{1b}$ and $R^{1c}$ are each as defined herein. In certain embodiments, $R^1$ is —OS(O)$_2$N$R^{1b}R^{1c}$, wherein $R^{1b}$ and $R^{1c}$ are each as defined herein. In certain embodiments, $R^1$ is —N$R^{1b}R^{1c}$, wherein $R^{1b}$ and $R^{1c}$ are each as defined herein. In certain embodiments, $R^1$ is —NH$_2$. In certain embodiments, $R^1$ is —N$R^{1a}$C(O)$R^{1d}$, wherein $R^{1a}$ and $R^{1d}$ are each as defined herein. In certain embodiments, $R^1$ is —N$R^{1a}$C(O)O$R^{1d}$, wherein $R^{1a}$ an $R^{1d}$ are each as defined herein. In certain embodiments, $R^1$ is —N$R^{1a}$C(O)S$R^{1d}$, wherein $R^{1a}$ and $R^{1d}$ are each as defined herein. In certain embodiments, $R^1$ is —N$R^{1a}$C(O)N$R^{1b}R^{1c}$, wherein $R^{1a}$, $R^{1b}$ and $R^{1c}$ are each as defined herein. In certain embodiments, $R^1$ is —NHC(O)NH$_2$. In certain embodiments, $R^1$ is —N$R^{1a}$C(=N$R^{1d}$)$R^{1b}$, wherein $R^{1a}$, $R^{1b}$, and $R^{1d}$ are each as defined herein. In certain embodiments, $R^1$ is —N$R^{1a}$C(=N$R^{1d}$)$R^{1b}R^{1c}$, wherein $R^{1a}$, $R^{1b}$, $R^{1c}$ and $R^{1d}$ are each as defined herein. In certain embodiments, $R^1$ is —N$R^{1a}$C(S)$R^{1d}$, wherein $R^{1a}$ and $R^{1d}$ are each as defined herein. In certain embodiments, $R^1$ is —N$R^{1a}$C(S)O$R^{1d}$, wherein $R^{1a}$ and $R^{1d}$ are each as defined herein. In certain embodiments, $R^1$ is —$NR^{1a}C(S)NR^{1b}R^{1c}$, wherein $R^{1a}$, $R^{1b}$, and $R^{1c}$ are each as defined herein. In certain embodiments, $R^1$ is —$NR^{1a}S(O)R^{1d}$, wherein $R^{1a}$ and $R^{1d}$ are each as defined herein. In certain embodiments, $R^1$ is —$NR^{1a}S(O)_2R^{1d}$, wherein $R^{1a}$ and $R^{1d}$ are each as defined herein. In certain embodiments, $R^1$ is —$NR^{1a}S(O)NR^{1b}R^{1c}$, wherein $R^{1a}$, $R^{1b}$ and $R^{1c}$ are each as defined herein. In certain embodiments, $R^1$ is —$NR^{1a}S(O)_2NR^{1b}R^{1c}$, wherein $R^{1a}$, $R^{1b}$, and $R^{1c}$ are each as defined herein. In certain embodiments, $R^1$ is —$SR^{1a}$, wherein $R^{1a}$ is as defined herein. In certain embodiments, $R^1$ is —$SC(O)R^{1a}$, wherein $R^{1a}$ is as defined herein. In certain embodiments, $R^1$ is —$SC(O)NR^{1b}R^{1c}$, wherein $R^{1b}$ and $R^{1c}$ are each as defined herein. In certain embodiments, $R^1$ is —$S(O)R^{1a}$, wherein $R^{1a}$ is as defined herein. In certain embodiments, $R^1$ is —$S(O)_2R^{1a}$, wherein $R^{1a}$ is as defined herein. In certain embodiments, $R^1$ is —$S(O)_2OR^{1a}$, wherein $R^{1a}$ is as defined herein. In certain embodiments, $R^1$ is —$S(O)NR^{1b}R^{1c}$, wherein $R^{1b}$ and $R^{1c}$ are each as defined herein. In certain embodiments, $R^1$ is —$S(O)_2NR^{1b}R^{1c}$, wherein $R^{1b}$ and $R^{1c}$ are each as defined herein.

In certain embodiments, $R^2$ is heteroaryl, optionally substituted with one or more substituents Q. In certain embodiments, $R^2$ is bicyclic heteroaryl, optionally substituted with one or more substituents Q. In certain embodiments, $R^2$ is 5,6-fused bicyclic heteroaryl, optionally substituted with one or more substituents Q. In certain embodiments, $R^2$ is indolyl, optionally substituted with one or more substituents Q. In embodiments, $R^2$ is indol-3-yl, optionally substituted with one or more substituents Q. In certain embodiments, $R^2$ is —$OR^{1a}$, wherein $R^{1a}$ is as defined herein. In certain embodiments, $R^2$ is —O—$C_{1-6}$ alkyl, optionally substituted with one or more substituents Q. In certain embodiments, $R^2$ is —OH, —$OCH_3$, —$OCD_3$, or —$OCH_2CH_3$. In certain embodiments, $R^2$ is —$OC(O)R^{1a}$, wherein $R^{1a}$ is as defined herein. In certain embodiments, $R^2$ is —OC(O)—$C_{1-6}$ alkyl, optionally substituted with one or more substituents Q. In certain embodiments, $R^2$ is —$OC(O)CH_3$. In certain embodiments, $R^2$ is —$OC(O)OR^{1a}$, wherein $R^{1a}$ is as defined herein. In certain embodiments, $R^2$ is —$OC(O)NR^{1b}R^{1c}$, wherein $R^{1b}$ and $R^{1c}$ are each as defined herein. In certain embodiments, $R^2$ is —$OC(O)SR^{1a}$, wherein $R^{1a}$ is as defined herein. In certain embodiments, $R^2$ is —$OC(=NR^{1a})NR^{1b}R^{1c}$, wherein $R^{1a}$, $R^{1b}$, and $R^{1c}$ are each as defined herein. In certain embodiments, $R^2$ is —$OC(S)R^{1a}$, wherein $R^{1a}$ is as defined herein. In certain embodiments, $R^2$ is —$OC(S)OR^{1a}$, wherein $R^{1a}$ is as defined herein. In certain embodiments, $R^2$ is —$OC(S)NR^{1b}R^{1c}$, wherein $R^{1b}$ and $R^{1c}$ are each as defined herein. In certain embodiments, $R^2$ is —$OP(O)(OR^{1a})OR^{1d}$, wherein $R$ a and $R^{1d}$ are each as defined herein. In certain embodiments, $R^2$ is —$OS(O)R^{1a}$, wherein $R^{1a}$ is as defined herein. In certain embodiments, $R^2$ is —$OS(O)_2R^{1a}$, wherein $R^{1a}$ is as defined herein. In certain embodiments, $R^2$ is —$OS(O)_2OR^{1a}$, wherein $R^{1a}$ is as defined herein. In certain embodiments, $R^2$ is —$OS(O)NR^{1b}R^{1c}$, wherein $R^{1b}$ and $R^{1c}$ are each as defined herein. In certain embodiments, $R^2$ is —$OS(O)_2NR^{1b}R^{1c}$, wherein $R^{1b}$ and $R^{1c}$ are each as defined herein.

In certain embodiments, $R^2$ and $R^3$ together with the carbon atom to which they are attached form heterocyclylene, optionally substituted with one or more substituents Q. In certain embodiments, $R^2$ and $R^3$ together with the carbon atom to which they are attached form monocyclic heterocyclylene, optionally substituted with one or more substituents Q. In certain embodiments, $R^2$ and $R^3$ together with the carbon atom to which they are attached form 5- or 6-membered heterocyclylene, each optionally substituted with one or more substituents Q. In certain embodiments, $R^2$ and $R^3$ together with the carbon atom to which they are attached form 1,4-dioxandiyl, optionally substituted with one or more substituents Q. In certain embodiments, $R^2$ and $R^3$ together with the carbon atom to which they are attached form 1,4-dioxan-2,3-diyl, optionally substituted with one or more substituents Q.

In certain embodiments, $R^3$ is $C_{1-6}$ alkyl, optionally substituted with one or more substituents Q. In certain embodiments, $R^3$ is —$CH_2CN$. In certain embodiments, $R^3$ is —$OR^{1a}$, wherein $R^{1a}$ is as defined herein. In certain embodiments, $R^3$ is —OH. In certain embodiments, $R^3$ is —$OC(O)R^{1a}$, wherein $R^{1a}$ is as defined herein. In certain embodiments, $R^3$ is —OC(O)—$C_{1-6}$ alkyl, optionally substituted with one or more substituents Q. In certain embodiments, $R^3$ is —$OC(O)CH_2CH_2CH_3$. In certain embodiments, $R^3$ is —$OC(O)OR^{1a}$, wherein $R^{1a}$ is as defined herein. In certain embodiments, $R^3$ is —$OC(O)NR^{1b}R^{1c}$, wherein $R^{1b}$ and $R^{1c}$ are each as defined herein. In certain embodiments, $R^3$ is —$OC(O)SR^{1a}$, wherein $R^{1a}$ is as defined herein. In certain embodiments, $R^3$ is —$OC(=NR^{1a})NR^{1b}R^{1c}$, wherein $R^{1a}$, $R^{1b}$, and $R^{1c}$ are each as defined herein. In certain embodiments, $R^3$ is —$OC(S)R^{1a}$, wherein $R^{1a}$ is as defined herein. In certain embodiments, $R^3$ is —$OC(S)OR^{1a}$, wherein $R^{1a}$ is as defined herein. In certain embodiments, $R^3$ is —$OC(S)NR^{1b}R^{1c}$, wherein $R^{1b}$ and $R^{1c}$ are each as defined herein. In certain embodiments, $R^3$ is —$OP(O)(OR^{1a})OR^{1d}$, wherein $R^{1a}$ and $R^{1d}$ a each as defined herein. In certain embodiments, $R^3$ is —$OS(O)R^{1a}$, wherein $R^{1a}$ is as defined herein. In certain embodiments, $R^3$ is —$OS(O)_2R^{1a}$, wherein $R^{1a}$ is as defined herein. In certain embodiments, $R^3$ is —$OS(O)_2OR^{1a}$, wherein $R^{1a}$ is as defined herein. In certain embodiments, $R^3$ is —$OS(O)NR^{1b}R^{1c}$, wherein $R^{1b}$ and $R^{1c}$ are each as defined herein. In certain embodiments, $R^3$ is —$OS(O)_2NR^{1b}R^{1c}$, wherein $R^{1b}$ and $R^{1c}$ are each as defined herein. In certain embodiments, $R^3$ is —$NR^{1b}R^{1c}$, wherein $R^{1b}$ and $R^{1c}$ are each as defined herein. In certain embodiments, $R^3$ is —$NR^{1b}R^{1c}$, wherein $R^{1b}$ and $R^{1c}$ are each independently hydrogen or $C_{1-6}$ alkyl, optionally substituted with one or more substituents Q. In certain embodiments, $R^3$ is —$NHCH_3$. In certain embodiments, $R^3$ is —$NR^{1a}C(O)R^{1d}$, wherein $R^{1a}$ and $R^{1d}$ are each as defined herein. In certain embodiments, $R^3$ is $NR^{1a}C(O)OR^{1d}$, wherein $R^{1a}$ and $R^{1d}$ are each as defined herein. In certain embodiments, $R^3$ is —$NR^{1a}C(O)SR^{1d}$, wherein $R^{1a}$ and $R^{1d}$ are each as defined herein. In certain embodiments, $R^3$ is —$NR^{1a}C(O)NR^{1b}R^{1c}$, wherein $R^{1a}$, $R^{1b}$, and $R^{1c}$ are each as defined herein. In certain embodiments, $R^3$ is —$NR^{1a}C(=NR^{1d})R^{1b}$, wherein $R^{1a}$, $R^{1b}$, and $R^{1d}$ are each as defined herein. In certain embodiments, $R^3$ is —$NR^{1a}C(=NR^{1d})R^{1b}R^{1c}$, wherein $R^{1a}$, $R^{1b}$, $R^{1c}$ and $R^{1d}$ are each as defined herein. In certain embodiments, $R^3$ is —$NR^{1a}C(S)R^{1d}$, wherein $R^{1a}$ and $R^{1d}$ are each as defined herein. In certain embodiments, $R^3$ is —$NR^{1a}C(S)OR^{1d}$, wherein $R^{1a}$ and $R^{1d}$ are each as defined herein. In certain embodiments, $R^3$ is —$NR^{1a}C(S)NR^{1b}R^{1c}$, wherein $R^{1a}$, $R^{1b}$, and $R^{1c}$ are each as defined herein. In certain embodiments, $R^3$ is —$NR^{1a}S(O)R^d$, wherein $R^{1a}$ and $R^{1d}$ are each as defined herein. In certain embodiments, $R^3$ is —$NR^{1a}S(O)_2R^{1d}$, wherein $R^{1a}$ and $R^{1d}$ are each as defined herein. In certain embodiments, $R^3$ is —$NR^{1a}S(O)NR^{1b}R^{1c}$, wherein $R^{1a}$, $R^{1b}$, and $R^{1c}$ are each as defined herein. In certain embodiments, $R^3$ is —$NR^{1a}S(O)_2NR^{1b}R^{1c}$, wherein $R^{1a}$, $R^{1b}$, and $R^{1c}$ are each as defined herein.

In certain embodiments, $R^4$ is hydrogen. In certain embodiments, $R^4$ is $C_{1-6}$ alkyl, optionally substituted with one or more substituents Q. In certain embodiments, $R^4$ is —OR$^{1a}$, wherein R$^{1a}$ is as defined herein. In certain embodiments, R$^4$ is —OH. In certain embodiments, R$^4$ is —OC(O) R$^{1a}$, wherein R$^{1a}$ is as defined herein. In certain embodiments, R$^4$ is —OC(O)—C$_{1-6}$ alkyl, optionally substituted with one or more substituents Q. In certain embodiments, R$^4$ is —OC(O)CH$_2$CH$_2$CH$_3$. In certain embodiments, R$^4$ is —OC(O)OR$^{1a}$, wherein R$^{1a}$ is as defined herein. In certain embodiments, R$^4$ is —OC(O)NR$^{1b}$R$^{1c}$, wherein R$^{1b}$ and R$^{1c}$ are each as defined herein. In certain embodiments, R$^4$ is —OC(O)SR$^{1a}$, wherein R$^{1a}$ is as defined herein. In certain embodiments, R$^4$ is —OC(=NR$^{1a}$)NR$^{1b}$R$^{1c}$, wherein R$^{1a}$, R$^{1b}$, and R$^{1c}$ are each as defined herein. In certain embodiments, R$^4$ is —OC(S)R$^{1a}$, wherein R$^{1a}$ is as defined herein. In certain embodiments, R$^4$ is —OC(S)OR$^{1a}$, wherein R$^{1a}$ is as defined herein. In certain embodiments, R$^4$ is —OC(S) NR$^{1b}$R$^{1c}$, wherein R$^{1b}$ and R$^{1c}$ are each as defined herein. In certain embodiments, R$^4$ is —OP(O)(OR$^{1a}$)OR$^{1d}$, wherein R$^{1a}$ and R$^{1d}$ are each as defined herein. In certain embodiments, R$^4$ is —OS(O)R$^{1a}$, wherein R$^{1a}$ is as defined herein. In certain embodiments, R$^4$ is —OS(O)$_2$R$^{1a}$, wherein R$^{1a}$ is as defined herein. In certain embodiments, R$^4$ is —OS(O) $_2$OR$^{1a}$, wherein R$^{1a}$ is as defined herein. In certain embodiments, R$^4$ is —OS(O)NR$^{1b}$R$^{1c}$, wherein R$^{1b}$ and R$^{1c}$ are each as defined herein. In certain embodiments, R$^4$ is —OS (O)$_2$NR$^{1b}$R$^{1c}$, wherein R$^{1b}$ and R$^{1c}$ are each as defined herein. In certain embodiments, R$^4$ is —NR$^{1b}$R$^{1c}$, wherein R$^{1b}$ and R$^{1c}$ are each as defined herein. In certain embodiments, R$^4$ is —NR$^{1b}$R$^{1c}$, wherein R$^{1b}$ and R$^{1c}$ are each independently hydrogen or C$_{1-6}$ alkyl, optionally substituted with one or more substituents Q. In certain embodiments, R$^4$ is —NHCH$_3$. In certain embodiments, R$^4$ is —NR$^{1a}$C(O) R$^{1d}$, wherein R$^{1a}$ and R$^{1d}$ are each as defined herein. In certain embodiments, R$^4$ is NR$^{1a}$C(O)OR$^{1d}$, wherein R$^{1a}$ and R$^{1d}$ are each as defined herein. In certain embodiments, R$^4$ is —NR$^{1a}$C(O)SR$^{1d}$, wherein R$^{1a}$ and R$^{1d}$ are each as defined herein. In certain embodiments, R$^4$ is —NR$^{1a}$C(O) NR$^{1b}$R$^{1c}$, wherein R$^{1a}$, R$^{1b}$, and R$^{1c}$ are each as defined herein. In certain embodiments, R$^4$ is —NR$^{1a}$C(=NR$^{1d}$) R$^{1b}$, wherein R$^{1a}$, R$^{1b}$, and R$^{1d}$ are each as defined herein. In certain embodiments, R$^4$ is —NR$^{1a}$C(=NR$^{1d}$)R$^{1b}$R$^{1c}$, wherein R$^{1a}$, R$^{1b}$, R$^{1c}$, and R$^{1d}$ are each as defined herein. In certain embodiments, R$^4$ is —NR$^{1a}$C(S)R$^{1d}$, wherein R$^{1a}$ and R$^{1d}$ are each as defined herein. In certain embodiments, R$^4$ is —NR$^{1a}$C(S)OR$^{1d}$, wherein R$^{1a}$ and R$^{1d}$ are each as defined herein. In certain embodiments, R$^4$ is —NR$^{1a}$C(S) NR$^{1b}$R$^{1c}$, wherein R$^{1a}$, R$^{1b}$, and R$^{1c}$ are each as defined herein. In certain embodiments, R$^4$ is —NR$^{1a}$S(O)R$^{1d}$, wherein R$^{1a}$ and R$^{1d}$ are each as defined herein. In certain embodiments, R$^4$ is —NR$^{1a}$S(O)$_2$R$^{1d}$, wherein R$^{1a}$ and R$^{1d}$ are each as defined herein. In certain embodiments, R$^4$ is —NR$^{1a}$S(O)NR$^{1b}$R$^{1c}$, wherein R$^{1a}$, R$^{1b}$, and R$^{1c}$ are each as defined herein. In certain embodiments, R$^4$ is —NR$^{1a}$S(O) $_2$NR$^{1b}$R$^{1c}$, wherein R$^{1a}$, R$^{1b}$, and R$^{1c}$ are each as defined herein.

In certain embodiments, R$^3$ and R$^4$ together with the carbon atom to which they are attached form heterocyclylene, optionally substituted with one or more substituents Q. In certain embodiments, R$^3$ and R$^4$ together with the carbon atom to which they are attached form monocyclic heterocyclylene, optionally substituted with one or more substituents Q. In certain embodiments, R$^3$ and R$^4$ together with the carbon atom to which they are attached form 5- or 6-membered heterocyclylene, each optionally substituted with one or more substituents Q. In certain embodiments, R$^3$ and R$^4$ together with the carbon atom to which they are attached form 1,3-dioxolandiyl, optionally substituted with one or more substituents Q. In certain embodiments, R$^3$ and R$^4$ together with the carbon atom to which they are attached form 1,3-dioxolan-2,2-diyl, optionally substituted with one or more substituents Q. In certain embodiments, R$^3$ and R$^4$ together with the carbon atom to which they are attached form =CR$^{1a}$R$^{1c}$, wherein R$^{1a}$ and R$^{1c}$ are each as defined herein. In certain embodiments, R$^3$ and R$^4$ together with the carbon atom to which they are attached form =CR$^{1a}$CN, wherein R$^{1a}$ is as defined herein. In certain embodiments, R$^3$ and R$^4$ together with the carbon atom to which they are attached form =CHCN. In certain embodiments, R$^3$ and R$^4$ together with the carbon atom to which they are attached form =CO. In certain embodiments, R$^3$ and R$^4$ together with the carbon atom to which they are attached form =NR$^{1b}$, wherein R$^{1b}$ is as defined herein. In certain embodiments, R$^3$ and R$^4$ together with the carbon atom to which they are attached form =NOR$^{1b}$, wherein R$^{1b}$ is as defined herein. In certain embodiments, R$^3$ and R$^4$ together with the carbon atom to which they are attached form =NNR$^{1a}$C (O)R$^{1d}$, wherein R$^{1a}$ and R$^{1d}$ are each as defined herein. In certain embodiments, R$^3$ and R$^4$ together with the carbon atom to which they are attached form =NNHC(O)R$^{1d}$, wherein R$^{1d}$ is C$_{1-6}$ alkyl, C$_{6-14}$ aryl, or heteroaryl, each of which is optionally substituted with one or more substituents Q. In certain embodiments, R$^3$ and R$^4$ together with the carbon atom to which they are attached form =NNHC(O) R$^{1d}$, wherein R$^{1d}$ is methyl, phenyl, or pyridine-4-yl. In certain embodiments, R$^3$ and R$^4$ together with the carbon atom to which they are attached form =NNR$^{1a}$C(O) NR$^{1b}$R$^{1c}$, wherein R$^{1a}$, R$^{1b}$, and R$^{1c}$ are each as defined herein. In certain embodiments, R$^3$ and R$^4$ together with the carbon atom to which they are attached form =NNHC(O) NH$_2$.

In certain embodiments, R$^5$ is C$_{1-6}$ alkyl, optionally substituted with one or more substituents Q. In certain embodiments, R$^5$ is —CH$_2$CN. In certain embodiments, R$^5$ is —OR$^{1a}$, wherein R$^{1a}$ is as defined herein. In certain embodiments, R$^5$ is —OH. In certain embodiments, R$^5$ is —OC(O) R$^{1a}$, wherein R$^{1a}$ is as defined herein. In certain embodiments, R$^5$ is —OC(O)—C$_{1-6}$ alkyl, optionally substituted with one or more substituents Q. In certain embodiments, R$^5$ is —OC(O)CH$_2$CH$_2$CH$_3$. In certain embodiments, R$^5$ is —OC(O)OR$^{1a}$, wherein R$^{1a}$ is as defined herein. In certain embodiments, R$^5$ is —OC(O)NR$^{1b}$R$^{1c}$, wherein R$^{1b}$ and R$^{1c}$ are each as defined herein. In certain embodiments, R$^5$ is —OC(O)SR$^{1a}$, wherein R$^{1a}$ is as defined herein. In certain embodiments, R$^5$ is —OC(=NR$^{1a}$)NR$^{1b}$R$^{1c}$, wherein R$^{1a}$, R$^{1b}$, and R$^{1c}$ are each as defined herein. In certain embodiments, R$^a$ is —OC(S)R$^{1a}$, wherein R$^{1a}$ is as defined herein. In certain embodiments, R$^5$ is —OC(S)OR$^{1a}$, wherein R$^{1a}$ is as defined herein. In certain embodiments, R$^5$ is —OC(S) NR$^{1b}$R$^{1c}$, wherein R$^{1b}$ and R$^{1c}$ are each as defined herein. In certain embodiments, R$^5$ is —OP(O)(OR$^{1a}$)OR$^{1d}$, wherein R$^{1a}$ and R$^{1d}$ a each as defined herein. In certain embodiments, R$^5$ is —OS(O)R$^{1a}$, wherein R$^{1a}$ is as defined herein. In certain embodiments, R$^5$ is —OS(O)$_2$R$^{1a}$, wherein R$^{1a}$ is as defined herein. In certain embodiments, R$^5$ is —OS(O) $_2$OR$^{1a}$, wherein R$^{1a}$ is as defined herein. In certain embodiments, R$^5$ is —OS(O)NR$^{1b}$R$^{1c}$, wherein R$^{1b}$ and R$^{1c}$ are each as defined herein. In certain embodiments, R$^5$ is —OS (O)$_2$NR$^{1b}$R$^{1c}$, wherein R$^{1b}$ and R$^{1c}$ are each as defined herein. In certain embodiments, R$^5$ is —NR$^{1b}$R$^{1c}$, wherein R$^{1b}$ and R$^{1c}$ are each as defined herein. In certain embodiments, R$^5$ is —NR$^{1b}$R$^{1c}$, wherein R$^{1b}$ and R$^{1c}$ are each independently hydrogen or C$_{1-6}$ alkyl, optionally substituted with one or more substituents Q. In certain embodiments, R$^5$ is —NHCH$_3$. In certain embodiments, R$^5$ is —NR$^{1a}$C(O) R$^{1d}$, wherein R$^{1a}$ and R$^{1d}$ are each as defined herein. In certain embodiments, $R^5$ is —$NR^{1a}C(O)OR^{1d}$, wherein $R^{1a}$ and $R^{1d}$ are each as defined herein. In certain embodiments, $R^5$ is —$NR^{1a}C(O)SR^{1d}$, wherein $R^{1a}$ and $R^{1d}$ are each as defined herein. In certain embodiments, $R^5$ is —$NR^{1a}C(O)NR^{1b}R^{1c}$, wherein $R^{1a}$, $R^{1b}$, and $R^{1c}$ are each as defined herein. In certain embodiments, $R^5$ is —$NR^{1a}C(=NR^{1d})R^{1b}$, wherein $R^{1a}$, $R^{1b}$, and $R^{1d}$ are each as defined herein. In certain embodiments, $R^5$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^5$ is —$NR^{1a}C(S)R^{1d}$, wherein $R^{1a}$ and $R^{1d}$ are each as defined herein. In certain embodiments, $R^5$ is —$NR^{1a}C(S)OR^{1d}$, wherein $R^{1a}$ and $R^{1d}$ are each as defined herein. In certain embodiments, $R^5$ is —$NR^{1a}C(S)NR^{1b}R^{1c}$, wherein $R^{1a}$, $R^{1b}$, and $R^{1c}$ are each as defined herein. In certain embodiments, $R^5$ is —$NR^{1a}S(O)R^{1d}$, wherein $R^{1a}$ and $R^{1d}$ are each as defined herein. In certain embodiments, $R^5$ is —$NR^{1a}S(O)_2R^{1d}$, wherein $R^{1a}$ and $R^{1d}$ are each as defined herein. In certain embodiments, $R^5$ is —$NR^{1a}S(O)NR^{1b}R^{1c}$, wherein $R^{1a}$, $R^{1b}$ and $R^{1c}$ are each as defined herein. In certain embodiments, $R^5$ is —$NR^{1a}S(O)_2NR^{1b}R^{1c}$, wherein $R^{1a}$, $R^{1b}$, and $R^{1d}$ are each as defined herein.

In certain embodiments, $R^6$ is hydrogen. In certain embodiments, $R^6$ is $C_{1-6}$ alkyl, optionally substituted with one or more substituents Q. In certain embodiments, $R^6$ is —$OR^{1a}$, wherein $R^{1a}$ is as defined herein. In certain embodiments, $R^6$ is —OH. In certain embodiments, $R^6$ is —$OC(O)R^{1a}$, wherein $R^{1a}$ is as defined herein. In certain embodiments, $R^6$ is —$OC(O)$—$C_{1-6}$ alkyl, optionally substituted with one or more substituents Q. In certain embodiments, $R^6$ is —$OC(O)CH_2CH_2CH_3$. In certain embodiments, $R^6$ is —$OC(O)OR^{1a}$, wherein $R^{1a}$ is as defined herein. In certain embodiments, $R^6$ is —$OC(O)NR^{1b}R^{1c}$, wherein $R^{1b}$ and $R^{1c}$ are each as defined herein. In certain embodiments, $R^6$ is —$OC(O)SR^{1a}$, wherein $R^{1a}$ is as defined herein. In certain embodiments, $R^6$ is —$OC(=NR^{1a})NR^{1b}R^{1c}$, wherein $R^{1a}$, $R^{1b}$, and $R^{1c}$ are each as defined herein. In certain embodiments, $R^6$ is —$OC(S)R^{1a}$, wherein $R^{1a}$ is as defined herein. In certain embodiments, $R^6$ is —$OC(S)OR^{1a}$, wherein $R^{1a}$ is as defined herein. In certain embodiments, $R^6$ is —$OC(S)NR^{1b}R^{1c}$, wherein $R^{1b}$ and $R^{1c}$ are each as defined herein. In certain embodiments, $R^6$ is —$OP(O)(OR^{1a})OR^{Id}$, wherein $R^{1a}$ and $R^{1d}$ are each as defined herein. In certain embodiments, $R^6$ is —$OS(O)R^{1a}$, wherein $R^{1a}$ is as defined herein. In certain embodiments, $R^6$ is —$OS(O)_2R^{1a}$, wherein $R^{1a}$ is as defined herein. In certain embodiments, $R^6$ is —$OS(O)_2OR^{1a}$, wherein $R^{1a}$ is as defined herein. In certain embodiments, $R^6$ is —$OS(O)NR^{1b}R^{1c}$, wherein $R^{1b}$ and $R^{1c}$ are each as defined herein. In certain embodiments, $R^6$ is —$OS(O)_2NR^{1b}R^{1c}$, wherein $R^{1b}$ and $R^{1c}$ are each as defined herein. In certain embodiments, $R^6$ is —$NR^{1b}R^{1c}$, wherein $R^{1b}$ and $R^c$ are each as defined herein. In certain embodiments, $R^6$ is —$NR^{1b}R^{1c}$, wherein $R^{1b}$ and $R^{1c}$ are each independently hydrogen or $C_{1-6}$ alkyl, optionally substituted with one or more substituents Q. In certain embodiments, $R^6$ is —$NHCH_3$. In certain embodiments, $R^6$ is —$NR^{1a}C(O)R^{1d}$, wherein $R^{1a}$ and $R^{1d}$ are each as defined herein. In certain embodiments, $R^6$ is $NR^{1a}C(O)OR^{1d}$, wherein $R^{1a}$ and $R^{1d}$ are each as defined herein. In certain embodiments, $R^6$ is —$NR^{1a}C(O)SR^{1d}$, wherein $R^{1a}$ and $R^{1d}$ are each as defined herein. In certain embodiments, $R^6$ is —$NR^{1a}C(O)NR^{1b}R^{1c}$, wherein $R^{1a}$, $R^{1b}$, and $R^{1c}$ are each as defined herein. In certain embodiments, $R^6$ is —$NR^{1a}C(=NR^{1d})R^{1b}$, wherein $R^{1a}$, $R^{1b}$, and $R^{1d}$ are each as defined herein. In certain embodiments, $R^6$ is —$NR^{1a}C(=NR^{1d})R^{1b}R^{1c}$, wherein $R^{1a}$, $R^{1b}$, $R^{1c}$ and $R^{1d}$ are each as defined herein. In certain embodiments, $R^6$ is —$NR^{1a}C(S)R^{1d}$, wherein $R^{1a}$ and $R^{1d}$ are each as defined herein. In certain embodiments, $R^6$ is —$NR^{1a}C(S)OR^{1d}$, wherein $R^{1a}$ and $R^{1d}$ are each as defined herein. In certain embodiments, $R^6$ is —$NR^{1a}C(S)NR^{1b}R^{1c}$, wherein $R^{1a}$, $R^{1b}$, and $R^{1c}$ are each as defined herein. In certain embodiments, $R^6$ is —$NR^{1a}S(O)R^{1d}$, wherein $R^{1a}$ and $R^{1d}$ are each as defined herein. In certain embodiments, $R^6$ is —$NR^{1a}S(O)_2R^{1d}$, wherein $R^{1a}$ and $R^d$ are each as defined herein. In certain embodiments, $R^6$ is —$NR^{1a}S(O)NR^{1b}R^{1c}$, wherein $R^{1a}$, $R^{1b}$, and $R^{1c}$ are each as defined herein. In certain embodiments, $R^6$ is —$NR^{1a}S(O)_2NR^{1b}R^{1c}$, wherein $R^{1a}$, $R^{1b}$, and $R^{1c}$ are each as defined herein.

In certain embodiments, $R^5$ and $R^6$ together with the carbon atom to which they are attached form heterocyclylene, optionally substituted with one or more substituents Q. In certain embodiments, $R^5$ and $R^6$ together with the carbon atom to which they are attached form monocyclic heterocyclylene, optionally substituted with one or more substituents Q. In certain embodiments, $R^5$ and $R^6$ together with the carbon atom to which they are attached form 5- or 6-membered heterocyclylene, each optionally substituted with one or more substituents Q. In certain embodiments, $R^5$ and $R^6$ together with the carbon atom to which they are attached form 1,3-dioxolandiyl, optionally substituted with one or more substituents Q. In certain embodiments, $R^5$ and $R^6$ together with the carbon atom to which they are attached form 1,3-dioxolan-2,2-diyl, optionally substituted with one or more substituents Q. In certain embodiments, $R^5$ and $R^6$ together with the carbon atom to which they are attached form =$CR^{1a}R^{1c}$, wherein $R^{1a}$ and $R^{1c}$ are each as defined herein. In certain embodiments, $R^5$ and $R^6$ together with the carbon atom to which they are attached form =$CR^{1a}CN$, wherein $R^{1a}$ is as defined herein. In certain embodiments, $R^5$ and $R^6$ together with the carbon atom to which they are attached form =CHCN. In certain embodiments, $R^5$ and $R^6$ together with the carbon atom to which they are attached form =CO. In certain embodiments, $R^5$ and $R^6$ together with the carbon atom to which they are attached form =$NR^{1b}$, wherein $R^{1b}$ is as defined herein. In certain embodiments, $R^5$ and $R^6$ together with the carbon atom to which they are attached form =$NOR^{1b}$, wherein $R^{1b}$ is as defined herein. In certain embodiments, $R^5$ and $R^6$ together with the carbon atom to which they are attached form =NOH.

In certain embodiments, $R^3$, $R^4$, and $R^5$ together with the carbon atoms to which they are attached form unsaturated heterocyclylene, optionally substituted with one or more substituents Q. In certain embodiments, $R^3$, $R^4$, and $R^5$ together with the carbon atoms to which they are attached form unsaturated monocyclic heterocyclylene, optionally substituted with one or more substituents Q. In certain embodiments, $R^3$, $R^4$, and $R^5$ together with the carbon atoms to which they are attached form unsaturated 5- or 6-membered heterocyclylene, each optionally substituted with one or more substituents Q. In certain embodiments, $R^3$, $R^4$, and $R^5$ together with the carbon atoms to which they are attached form 3,6-dihydro-1,4-oxazindiyl, optionally substituted with one or more substituents Q. In certain embodiments, $R^3$, $R^4$, and $R^5$ together with the carbon atoms to which they are attached form 3,6-dihydro-1,4-oxazin-5,6-diyl, optionally substituted with one or more substituents Q. In certain embodiments, $R^3$, $R^4$, $R^5$, and $R^6$ together with the carbon atoms to which they are attached form 6-hydroxy-3,6-dihydro-1,4-oxazin-5,6-diyl.

In certain embodiments, $R^3$, $R^5$, and $R^6$ together with the carbon atoms to which they are attached form unsaturated heterocyclylene, optionally substituted with one or more substituents Q. In certain embodiments, $R^3$, $R^5$, and $R^6$ together with the carbon atoms to which they are attached form unsaturated monocyclic heterocyclylene, optionally substituted with one or more substituents Q. In certain embodiments, $R^3$, $R^5$, and $R^6$ together with the carbon atoms to which they are attached form unsaturated 5- or 6-membered heterocyclylene, each optionally substituted with one or more substituents Q. In certain embodiments, $R^3$, $R^5$, and $R^6$ together with the carbon atoms to which they are attached form 3,6-dihydro-1,4-oxazindiyl, optionally substituted with one or more substituents Q. In certain embodiments, $R^3$, $R^5$, and $R^6$ together with the carbon atoms to which they are attached form 3,6-dihydro-1,4-oxazin-5,6-diyl, optionally substituted with one or more substituents Q. In certain embodiments, $R^3$, $R^5$, and $R^6$ together with the carbon atoms to which they are attached form 2-oxo-3,6-dihydro-1,4-oxazin-5,6-diyl.

In certain embodiments, $R^{3a}$ is hydrogen. In certain embodiments, $R^{3a}$ is $C_{1-6}$ alkyl, optionally substituted with one or more substituents Q. In certain embodiments, $R^{3a}$ is —C(O)$R^{1a}$, wherein $R^{1a}$ is as defined herein. In certain embodiments, $R^{3a}$ is —C(O)—$C_{1-6}$ alkyl, optionally substituted with one or more substituents Q. In certain embodiments, $R^{3a}$ is —C(O)CH$_2$CH$_2$CH$_3$. In certain embodiments, $R^{3a}$ is —C(O)OR$^{1a}$, wherein $R^{1a}$ is as defined herein. In certain embodiments, $R^{3a}$ is —C(O)NR$^{1b}$R$^{1c}$, wherein $R^{1b}$ and $R^{1c}$ are each as defined herein. In certain embodiments, $R^{3a}$ is —C(O)SR$^{1a}$, wherein $R^{1a}$ is as defined herein. In certain embodiments, $R^{3a}$ is —C(=NR$^{1a}$)NR$^{1b}$R$^{1c}$, wherein $R^{1a}$, $R^{1b}$, and $R^{1c}$ are each as defined herein. In certain embodiments, $R^{3a}$ is —C(S)R$^{1a}$ wherein $R^{1a}$ is as defined herein. In certain embodiments, $R^{3a}$ is —C(S)OR$^{1a}$, wherein $R^{1a}$ is as defined herein. In certain embodiments, $R^{3a}$ is —C(S)NR$^{1b}$R$^{1c}$, wherein $R^{1b}$ and $R^{1c}$ are each as defined herein. In certain embodiments, $R^{3a}$ is —P(O)(OR$^{1a}$)OR$^{1d}$, wherein $R^{1a}$ and $R^{1d}$ are each as defined herein. In certain embodiments, $R^{3a}$ is —S(O)R$^{1a}$, wherein $R^{a}$ is as defined herein. In certain embodiments, $R^{3a}$ is —S(O)$_2$R$^{1a}$, wherein $R^{1a}$ is as defined herein. In certain embodiments, $R^{3a}$ is —S(O)$_2$OR$^{1a}$, wherein $R^{1a}$ is as defined herein. In certain embodiments, $R^{3a}$ is —S(O)NR$^{1b}$R$^{1c}$, wherein $R^{1b}$ and $R^{1c}$ are each as defined herein. In certain embodiments, $R^{3a}$ is —S(O)$_2$NR$^{1b}$R$^{1c}$, wherein $R^{1b}$ and $R^{1c}$ are each as defined herein.

In certain embodiments, $R^{3b}$ is hydrogen. In certain embodiments, $R^{3b}$ is deuterium. In certain embodiments, $R^{3b}$ is $C_{1-6}$ alkyl, optionally substituted with one or more substituents Q. In certain embodiments, $R^{3b}$ is $C_{2-6}$ alkenyl, optionally substituted with one or more substituents Q. In certain embodiments, $R^{3b}$ is $C_{2-6}$ alkynyl, optionally substituted with one or more substituents Q. In certain embodiments, $R^{3b}$ is $C_{3-10}$ cycloalkyl, optionally substituted with one or more substituents Q. In certain embodiments, $R^{3b}$ is $C_{6-14}$ aryl, optionally substituted with one or more substituents Q. In certain embodiments, $R^{3b}$ is $C_{7-15}$ aralkyl, optionally substituted with one or more substituents Q. In certain embodiments, $R^{3b}$ is heteroaryl, optionally substituted with one or more substituents Q. In certain embodiments, $R^{3b}$ is heterocyclyl, optionally substituted with one or more substituents Q.

In certain embodiments, $R^{5a}$ is hydrogen. In certain embodiments, $R^{5a}$ is $C_{1-6}$ alkyl, optionally substituted with one or more substituents Q. In certain embodiments, $R^{5a}$ is —C(O)R$^{1a}$, wherein $R^{1a}$ is as defined herein. In certain embodiments, $R^{5a}$ is —C(O)—$C_{1-6}$ alkyl, optionally substituted with one or more substituents Q. In certain embodiments, $R^{5a}$ is —C(O)CH$_2$CH$_2$CH$_3$. In certain embodiments, $R^{5a}$ is —C(O)OR$^{1a}$, wherein $R^{1a}$ is as defined herein. In certain embodiments, $R^{5a}$ is —C(O)NR$^{1b}$R$^{1c}$, wherein $R^{1b}$ and $R^{1c}$ are each as defined herein. In certain embodiments, $R^{5a}$ is —C(O)SR$^{1a}$, wherein $R^{1a}$ is as defined herein. In certain embodiments, $R^{5a}$ is —C(=NR$^{1a}$)NR$^{1b}$R$^{1c}$, wherein $R^{1a}$, $R^{1b}$, and $R^{1c}$ are each as defined herein. In certain embodiments, $R^{5a}$ is —C(S)R$^{1a}$, wherein $R^{1a}$ is as defined herein. In certain embodiments, $R^{5a}$ is —C(S)OR$^{1a}$, wherein $R^{1a}$ is as defined herein. In certain embodiments, $R^{5a}$ is —C(S)NR$^{1b}$R$^{1c}$, wherein $R^{1b}$ and $R^{1c}$ are each as defined herein. In certain embodiments, $R^{5a}$ is —P(O)(OR$^{1a}$)OR$^{1d}$, wherein $R^{1a}$ and $R^{1d}$ are each as defined herein. In certain embodiments, $R^{5a}$ is —S(O)R$^{1a}$, wherein $R^{1a}$ is as defined herein. In certain embodiments, $R^{5a}$ is —S(O)$_2$R$^{1a}$, wherein $R^{1a}$ is as defined herein. In certain embodiments, Rea is —S(O)$_2$OR$^{1a}$, wherein $R^{1a}$ is as defined herein. In certain embodiments, $R^{5a}$ is —S(O)NR$^{1b}$R$^{1c}$, wherein $R^{1a}$ and $R^{1c}$ are each as defined herein. In certain embodiments, $R^{5a}$ is —S(O)$_2$NR$^{1b}$R$^{1c}$, wherein $R^{1b}$ and $R^{1c}$ are each as defined herein.

In one embodiment, provided herein is a compound, which is:

(2R,4aS,6aS,9S,12bR,14aS,14bR)-9-methoxy-2,4a,6a,9, 12b,14a-hexamethyl-10,11-dioxo-1,2,3,4,4a,5,6,6a,9,10, 11,12b,13,14,14a,14b-hexadecahydropicene-2-carboxylic acid A1;

(2R,4aS,6aS,9S,12bR,14aS,14bR)-9-(methoxy-d$_3$)-2,4a,6a, 9,12b,14a-hexamethyl-10,11-dioxo-1,2,3,4,4a,5,6,6a,9, 10,11,12b,13,14,14a,14b-hexadecahydropicene-2-carboxylic acid A2;

(2R,4aS,6aS,12bR,14aS,14bR)-9-(acetyloxy)-2,4a,6a,9, 12b,14a-hexamethyl-10,11-dioxo-1,2,3,4,4a,5,6,6a,9,10, 11,12b,13,14,14a,14b-hexadecahydropicene-2-carboxylic acid A3;

methyl (2R,4aS,6aS,12bR,14aS,14bR)-9-(1H-indol-3-yl)-2, 4a,6a,9,12b,14a-hexamethyl-10,11-dioxo-1,2,3,4,4a,5,6, 6a,9,10,11,12b,13,14,14a,14b-hexadecahydropicene-2-carboxylate A4;

methyl (2R,4aS,6aS,9S,12bR,14aS,14bR)-9-methoxy-2,4a, 6a,9,12b,14a-hexamethyl-10,11-dioxo-1,2,3,4,4a,5,6,6a, 9,10,11,12b,13,14,14a,14b-hexadecahydropicene-2-carboxylate A5;

1H-1,2,3-benzotriazol-1-yl (2R,4aS,6aS,9S,12bR,14aS, 14bR)-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxylate A6;

(2R,4aS,6aS,9S,12bR,14aS,14bR)-9-methoxy-N,2,4a,6a,9, 12b,14a-heptamethyl-10,11-dioxo-1,2,3,4,4a,5,6,6a,9,10, 11,12b,13,14,14a,14b-hexadecahydropicene-2-carboxamide A7;

(2R,4aS,6aS,9S,12bR,14aS,14bR)-9-methoxy-2,4a,6a,9, 12b,14a-hexamethyl-10,11-dioxo-1,2,3,4,4a,5,6,6a,9,10, 11,12b,13,14,14a,14b-hexadecahydropicene-2-carbonyl fluoride A8;

(2R,4aS,6aS,9S,12bR,14aS,14bR)-9-methoxy-2,4a,6a,9, 12b,14a-hexamethyl-10,11-dioxo-1,2,3,4,4a,5,6,6a,9,10, 11,12b,13,14,14a,14b-hexadecahydropicene-2-carboxamide A9;

(2R,4aS,6aS,9S,12bR,14aS,14bR)—N-ethyl-9-methoxy-2, 4a,6a,9,12b,14a-hexamethyl-10,11-dioxo-1,2,3,4,4a,5,6, 6a,9,10,11,12b,13,14,14a,14b-hexadecahydropicene-2-carboxamide A10;

benzyl (2R,4aS,6aS,9S,12bR,14aS,14bR)-9-methoxy-2,4a, 6a,9,12b,14a-hexamethyl-10,11-dioxo-1,2,3,4,4a,5,6,6a, 9,10,11,12b,13,14,14a,14b-hexadecahydropicene-2-carboxylate A11;

(2R,4aS,6aS,9S,12bR,14aS,14bR)—N-propyl-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A12;

(2R,4aS,6aS,9S,12bR,14aS,14bR)-9-methoxy-N,N,2,4a,6a,9,12b,14a-octamethyl-10,11-dioxo-1,2,3,4,4a,5,6,6a,9,10,11,12b,13,14,14a,14b-hexadecahydropicene-2-carboxamide A13;

(4S,6bS,8aS,11R,12aR,12bS,14aR)-11-(hydroxymethyl)-4-methoxy-4,6b,8a,11,12b,14a-hexamethyl-4,6b,7,8,8a,9,10,11,12,12a,12b,13,14,14a-tetradecahydropicene-2,3-dione A14;

(2R,4aS,6aS,9S,12bR,14aS,14bR)-9-ethoxy-2,4a,6a,9,12b,14a-hexamethyl-10,11-dioxo-1,2,3,4,4a,5,6,6a,9,10,11,12b,13,14,14a,14b-hexadecahydropicene-2-carboxylic acid A28;

methyl (2R,4aS,6aS,12bR,14aS,14bR)-9-hydroxy-2,4a,6a,9,12b,14a-hexamethyl-10,11-dioxo-1,2,3,4,4a,5,6,6a,9,10,11,12b,13,14,14a,14b-hexadecahydropicene-2-carboxylate A32;

(2R,4aS,6aS,9S,12bR,14aS,14bR)-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carbonitrile A39;

(4S,6bS,8aS,11R,12aR,12bS,14aR)-11-(aminomethyl)-4-methoxy-4,6b,8a,11,12b,14a-hexamethyl-4,6b,7,8,8a,9,10,11,12,12a,12b,13,14,14a-tetradecahydropicene-2,3-dione A40;

(4S,6bS,8aS,11R,12aR,12bS,14aR)-11-amino-4-methoxy-4,6b,8a,11,12b,14a-hexamethyl-4,6b,7,8,8a,9,10,11,12,12a,12b,13,14,14a-tetradecahydropicene-2,3-dione A41; or 1-((2R,4aS,6aS,9S,12bR,14aS,14bR)-9-methoxy-2,4a,6a,9,12b,14a-hexamethyl-10,11-dioxo-1,2,3,4,4a,5,6,6a,9,10,11,12b,13,14,14a,14b-hexadecahydropicen-2-yl)urea A42;

or a diastereomer, a mixture of diastereomers, a tautomer, a mixture of two or more tautomers, or an isotopic variant thereof; or a pharmaceutically acceptable salt, solvate, hydrate, or prodrug thereof.

In another embodiment, provided herein is a compound, which is:

(2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A15;

benzyl (2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A16;

(2R,4aS,6aS,9S,10R,12bR,14aS,14bR)-10-hydroxy-9-methoxy-N,2,4a,6a,9,12b,14a-heptamethyl-11-oxo-1,2,3,4,4a,5,6,6a,9,10,11,12b,13,14,14a,14b-hexadecahydropicene-2-carboxamide A17;

(3R,4S,6bS,8aS,11R,12aR,12bS,14aR)-3-hydroxy-11-(hydroxymethyl)-4-methoxy-4,6b,8a,11,12b,14a-hexamethyl-2,3,4,6b,7,8,8a,9,10,11,12,12a,12b,13,14,14a-hexadecahydropicen-2-one A18;

(2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carbaldehyde A19;

methyl (2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A20;

(2R,4aS,6aR,9S,10R,12bR,14aS,14bR)-10-hydroxy-9-methoxy-2,4a,6a,9,12b,14a-hexamethyl-11-oxo-1,2,3,4,4a,5,6,6a,6b,7,8,8a,9,10,11,12b,13,14,14a,14b-icosahydropicene-2-carboxylic acid A21;

methyl (2R,4aS,6aR,9S,10R,12bR,14aS,14bR)-10-hydroxy-9-methoxy-2,4a,6a,9,12b,14a-hexamethyl-11-oxo-1,2,3,4,4a,5,6,6a,6b,7,8,8a,9,10,11,12b,13,14,14a,14b-icosahydropicene-2-carboxylate A22;

(3R,4S,6bS,8aS,11R,12aR,12bS,14aR)-4-methoxy-4,6b,8a,11,12b,14a-hexamethyl-11-(methylcarbamoyl)-2-oxo-2,3,4,6b,7,8,8a,9,10,11,12,12a,12b,13,14,14a-hexadecahydropicen-3-yl butyrate A23;

methyl (2R,4aS,6aS,9S,10R,12bR,14aS,14bR)-10-(butyryloxy)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A24;

methyl (2R,4aS,6aS,9S,12bR,14aS,14bR)-10-hydroxy-9-methoxy-2,4a,6a,9,12b,14a-hexamethyl-10-(methylamino)-11-oxo-1,2,3,4,4a,5,6,6a,9,10,11,12b,13,14,14a,14b-hexadecahydropicene-2-carboxylate A26;

benzyl (2R,4aS,6aS,9S,12bR,14aS,14bR)-10-hydroxy-9-methoxy-2,4a,6a,9,12b,14a-hexamethyl-10-(methylamino)-11-oxo-1,2,3,4,4a,5,6,6a,9,10,11,12b,13,14,14a,14b-hexadecahydropicene-2-carboxylate A27; or methyl (2R,4aS,6aS,12bR,14aS,14bR)-9,10-dihydroxy-2,4a,6a,9,12b,14a-hexamethyl-11-oxo-1,2,3,4,4a,5,6,6a,9,10,11,12b,13,14,14a,14b-hexadecahydropicene-2-carboxylate A35;

or a diastereomer, a mixture of diastereomers, a tautomer, a mixture of two or more tautomers, or an isotopic variant thereof; or a pharmaceutically acceptable salt, solvate, hydrate, or prodrug thereof.

In yet another embodiment, provided herein is a compound, which is:

methyl (2R,4aS,6aS,9S,10S,12bR,14aS,14bR)-10-(butyryloxy)-11-hydroxy-9-methoxy-2,4a,6a,9,12b,14a-hexamethyl-1,2,3,4,4a,5,6,6a,9,10,11,12b,13,14,14a,14b-hexadecahydropicene-2-carboxylate A25; or (2R,4aS,6aS,9S,12bR,14aS,14bR)-10,11-dihydroxy-9-methoxy-2,4a,6a,9,12b,14a-hexamethyl-1,2,3,4,4a,5,6,6a,9,10,11,12b,13,14,14a,14b-hexadecahydropicene-2-carboxylic acid A29;

or a diastereomer, a mixture of diastereomers, a tautomer, a mixture of two or more tautomers, or an isotopic variant thereof; or a pharmaceutically acceptable salt, solvate, hydrate, or prodrug thereof.

In yet another embodiment, provided herein is a compound, which is:

(2R,4aS,6aS,9S,10Z,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A30;

(2R,4aS,6aS,9S,10E,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A31;

methyl (2R,4aS,6aS,10Z,12bR,14aS,14bR)-10-(cyanomethylidene)-9-hydroxy-2,4a,6a,9,12b,14a-hexamethyl-11-oxo-1,2,3,4,4a,5,6,6a,9,10,11,12b,13,14,14a,14b-hexadecahydropicene-2-carboxylate A33;

methyl (2R,4aS,6aS,10E,12bR,14aS,14bR)-10-(cyanomethylidene)-9-hydroxy-2,4a,6a,9,12b,14a-hexamethyl-11-oxo-1,2,3,4,4a,5,6,6a,9,10,11,12b,13,14,14a,14b-hexadecahydropicene-2-carboxylate A34; or (2R,4aS,6aS,9S,10E,12bR,14aS,14bR)-10-(cyanomethylidene)-11-hydroxy-9-methoxy-2,4a,6a,9,12b,14a-hexamethyl-1,2,3,4,4a,5,6,6a,9,10,11,12b,13,14,14a,14b-hexa-
decahydropicene-2-carboxylic acid A36;

or a diastereomer, a mixture of diastereomers, a tautomer, a mixture of two or more tautomers, or an isotopic variant thereof; or a pharmaceutically acceptable salt, solvate, hydrate, or prodrug thereof.

In yet another embodiment, provided herein is a compound, which is:

methyl (2R,4aS,6aS,11E,12bR,14aS,14bR)-11-(cyanomethylidene)-9-hydroxy-2,4a,6a,9,12b,14a-hexamethyl-10-oxo-1,2,3,4,4a,5,6,6a,9,10,11,12b,13,14,14a,14b-hexa-decahydropicene-2-carboxylate A37; or (2R,4aS,6aS,9S,12bR,14aS,14bR)-10-(cyanomethyl)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A38;

or a diastereomer, a mixture of diastereomers, a tautomer, a mixture of two or more tautomers, or an isotopic variant thereof; or a pharmaceutically acceptable salt, solvate, hydrate, or prodrug thereof.

In still another embodiment, provided herein is a compound, which is:

(6bS,8aS,11R,12aR,12bS,14aR)-16a-hydroxy-4a,6b,8a,11,12b,14a-hexamethyl-16-oxo-2,3,4a,6b,7,8,8a,9,10,11,12,12a,12b,13,14,14a,16,16a-octadecahydropiceno[3,4-b][1,4]dioxine-11-carboxylic acid A43;

(2R,4aS,6aS,9S,12bR,14aS,14bR)—N-(2-hydroxyethyl)-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A44;

(2R,4aS,6aS,9S,12bR,14aS,14bR)—N-hydroxy-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A45;

(2R,4aS,6aS,9S,14bR,16aS,16bR)-13a-hydroxy-9-methoxy-2,4a,6a,9,14b,16a-hexamethyl-2,3,4,4a,5,6,6a,9,11,12,13a,14b,15,16,16a,16b-hexadecahydro-1H-piceno[2,3-b][1,4]oxazine-2-carboxylic acid A46;

(2R,4aS,6aS,9S,14bR,16aS,16bR)—N,13a-dihydroxy-9-methoxy-2,4a,6a,9,14b,16a-hexamethyl-2,3,4,4a,5,6,6a,9,11,12,13a,14b,15,16,16a,16b-hexadecahydro-1H-piceno[2,3-b][1,4]oxazine-2-carboxamide A47;

(2R,4aS,6aS,9S,12bR,14aS,14bR)-11-(hydroxyimino)-9-methoxy-2,4a,6a,9,12b,14a-hexamethyl-10-oxo-1,2,3,4,4a,5,6,6a,9,10,11,12b,13,14,14a,14b-hexadecahydropicene-2-carboxylic acid A48;

(2R,4aS,6aS,9S,12bR,14aS,14bR)-10-(2-carbamoylhydrazono)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A49;

(2R,4aS,6aS,9S,10S,12bR,14aS,14bR)-10-hydroxy-11-(hydroxyimino)-9-methoxy-2,4a,6a,9,12b,14a-hexamethyl-1,2,3,4,4a,5,6,6a,9,10,11,12b,13,14,14a,14b-hexadecahydropicene-2-carboxylic acid A50;

(2R,4aS,6aS,9S,12bR,14aS,14bR)-10-(acetamidoimino)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A51;

(2R,4aS,6aS,9S,12bR,14aS,14bR)-9-Methoxy-2,4a,6a,9,12b,14a-hexamethyl-11-oxo-10-{[(pyridin-4-yl)formamido]imino}-1,2,3,4,4a,5,6,6a,9,10,11,12b,13,14,14a,14b-hexadecahydropicene-2-carboxylic acid A52;

(2R,4aS,6aS,9S,12bR,14aS,14bR)-10-(2-benzoylhydrazono)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A53;

(4S,6bS,8aS,11R,12aR,12bS,14aR)-4-methoxy-4,6b,8a,11,12b,14a-hexamethyl-3-oxo-4,6b,7,8,8a,9,10,11,12,12a,12b,13,14,14a-tetradecahydro-3H-spiro[picene-2,2'-[1,3]dioxolane]-11-carboxylic acid A54;

(2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxamide A55;

(3R,4S,6bS,8aS,11R,12aR,12bS,14aR)-3-hydroxy-4-methoxy-4,6b,8a,11,12b,14a-hexamethyl-11-(morpholine-4-carbonyl)-4,6b,7,8,8a,9,10,11,12,12a,12b,13,14,14a-tetradecahydropicen-2(3H)-one A56;

(2R,4aS,6aS,9S,10R,12bR,14aS,14bR)—N,10-dihydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxamide A57;

methyl (2R,4aS,6aS,9S,14bR,16aS,16bR)-9-methoxy-2,4a,6a,9,14b,16a-hexamethyl-11-oxo-1,3,4,4a,5,6,6a,9,9a,11,12,14b,15,16,16a,16b-hexadecahydro-2H-piceno[3,2-b][1,4]oxazine-2-carboxylate A58;

(2R,4aS,6aS,9S,10Z,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexa-decahydropicene-2-carboxamide A59;

benzyl (2R,4aS,6aS,9S,10Z,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A60;

benzyl (2R,4aS,6aS,9S,10E,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A61;

(2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carbonitrile A62; or N-[(2R,4aS,6aS,9S,12bR,14aS,14bR)-9-methoxy-2,4a,6a,9,12b,14a-hexamethyl-10,11-dioxo-1,2,3,4,4a,5,6,6a,9,10,11,12b,13,14,14a,14b-hexadecahydropicen-2-yl]acetamide A63;

or a diastereomer, a mixture of diastereomers, a tautomer, a mixture of two or more tautomers, or an isotopic variant thereof; or a pharmaceutically acceptable salt, solvate, hydrate, or prodrug thereof.

In certain embodiments, a compound provided herein is deuterium-enriched. In certain embodiments, a compound provided herein is carbon-12 enriched. In certain embodiments, a compound provided herein is carbon-13 enriched. In certain embodiments, a compound provided herein contains one or more less prevalent isotopes for other elements, including, but not limited to, $^{15}N$ for nitrogen; $^{17}O$ or $^{18}O$ for oxygen; and $^{34}S$, $^{35}S$, or $^{36}S$ for sulfur.

In certain embodiments, a compound provided herein has an isotopic enrichment factor of no less than about 5, no less than about 10, no less than about 20, no less than about 50, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, at least one of the atoms of a compound provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, a compound provided herein is isolated or purified. In certain embodiments, a compound provided herein has a purity of at least about 50%, at least about 70%, at least about 80%, at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

When a compound provided herein contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011. In certain embodiments, a pharmaceutically acceptable salt of a compound provided herein is a hydrate.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid. In certain embodiments, the compounds provided herein are hydrochloride salts.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med Chem.* 1996, 671-696; Asgharnejad in "Transport Processes in Pharmaceutical Systems," Amidon et al., Ed., Marcell Dekker, 185-218, 2000; Balant et al., *Eur. J Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, Drugs 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J Clin. Pharmac.* 1989, 28, 497-507.

Methods of Synthesis

The compounds provided herein can be prepared, isolated, or obtained by any method known to one of ordinary skill in the art. In certain embodiments, a compound of Formula (IX) is synthesized as shown in Scheme A, where $R^1$ and $R^2$ are each as defined herein. A compound of Formula (A) is treated with $R^2$—H in the presence of a base and oxygen to form a compound of Formula (IX).

Scheme A (A)

(IX)

In certain embodiments, a compound of Formula (XIII) is synthesized as shown in Scheme B, where $R^1$, $R^2$, and $R^{3a}$ are each as defined herein. A compound of Formula (IX) is reduced with a reducing agent (e.g., NaBH$_4$) to form a compound of Formula (B), which is then treated with $R^{3a}$—X to form a compound of Formula (XIII); where X is a leaving group (e.g., iodo, bromo, or chloro).

Scheme B (IX)

(B)

(XIII)

In certain embodiments, a compound of Formula (XIX) is synthesized as shown in Scheme C, where $R^1$, $R^2$, $R^{3a}$, and $R^{5a}$ are each as defined herein. A compound of Formula (XIII) is reduced with a reducing agent (e.g., NaBH$_4$) to form a compound of Formula (C), which is then treated with $R^{5a}$—X to form a compound of Formula (XIX); where X is a leaving group (e.g., iodo, bromo, or chloro).

Scheme C (XIII)

-continued (C)

(XIX)

In certain embodiments, a compound of Formula (XXIIIa) or (XXIIIb) is synthesized as shown in Scheme D, where $R^1$, $R^2$, and $R^{3b}$ are each as defined herein. A compound of Formula (IX) is treated with a reagent such as diethyl cyanomethylphosphonate in the presence of a base to form a compound of Formula (XXIIIa) or (XXIIIb), or a mixture thereof.

Scheme D (IX)

and/or (XXIIa)

-continued (XXIIb)

Pharmaceutical Compositions

In one embodiment, provided herein is a pharmaceutical composition, comprising a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The pharmaceutical composition provided herein can be formulated in various dosage forms, including dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, NY, 2008).

In one embodiment, the pharmaceutical composition provided herein is formulated in a dosage form for oral administration.

In another embodiment, the pharmaceutical composition provided herein is formulated in a dosage form for parenteral administration. In one embodiment, a pharmaceutical composition provided herein is formulated in a dosage form for intravenous administration. In another embodiment, a pharmaceutical composition provided herein is formulated in a dosage form for intramuscular administration. In yet another embodiment, a pharmaceutical composition provided herein is formulated in a dosage form for subcutaneous administration.

In yet another embodiment, a pharmaceutical composition provided herein is formulated in a dosage form for topical administration.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105, and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; algins; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 and CAB-O-SIL®; and mixtures thereof. The pharmaceutical compositions provided herein may contain about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethyl-cellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ and BIOJECT™.

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, ameliorating, or preventing one or more symptoms of a disorder, disease, or condition mediated by nuclear receptor subfamily 4 group A member 1 (Nur77) in a subject, comprising administering to the subject a therapeutically effective amount of a compound of Formula (I), or a diastereomer, a mixture of two or more diastereomers, a tautomer, a mixture of two or more tautomers, or an isotopic variant thereof, or a pharmaceutically acceptable salt, solvate, hydrate, or prodrug thereof.

In one embodiment, the disorder, disease, or condition mediated by Nur77 is a proliferative disease.

In another embodiment, provided herein is a method of treating, ameliorating, or preventing one or more symptoms of a proliferative disease in a subject, comprising administering to the subject a therapeutically effective amount of a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the proliferative disease is cancer. In certain embodiments, the cancer includes, but is not limited to, adrenal cortical cancer, anal cancer, bile duct cancer, bladder cancer, bone cancer, bone metastasis, brain cancer, breast cancer, cervical cancer, colorectal cancer, colon cancer, esophageal cancer, eye cancer, gallbladder cancer, gastrointestinal carcinoid tumor, gestational trophoblastic disease, Hodgkin's disease, non-Hodgkin's lymphoma, Kaposi's sarcoma, kidney cancer, laryngeal and hypopharyngeal cancer, leukemia, liver cancer, lung cancer, lung carcinoid tumor, malignant mesothelioma, metastatic cancer, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary cancer, prostate cancer, rectum cancer, retinoblastoma, salivary gland cancer, sarcoma, skin cancer, stomach cancer, testicular cancer, thymus cancer, thyroid cancer, uterine sarcoma, vaginal cancer, vulva cancer, or Wilm's tumor.

In certain embodiments, the cancer is breast cancer, cervical cancer, colorectal cancer, gastric cancer, hepatic cancer, lymphoma, lung cancer, melanoma, ovarian cancer, pancreatic cancer, or prostate cancer. In certain embodiments, the cancer is breast cancer, colorectal cancer, hepatic cancer, lung cancer, ovarian cancer, pancreatic cancer, or prostate cancer. In certain embodiments, the cancer is breast cancer, colorectal cancer, ovarian cancer, pancreatic cancer, or prostate cancer.

In certain embodiments, the cancer is metastatic. In certain embodiments, the cancer is refractory. In certain embodiments, the cancer is relapsed. In certain embodiments, the cancer is drug-resistant. In certain embodiments, the cancer is multidrug-resistant.

In certain embodiments, the subject is a mammal. In certain embodiments, the subject is a human.

In certain embodiments, the therapeutically effective amount is ranging from about 0.1 to about 100 mg/kg/day, from about 0.1 to about 50 mg/kg/day, from about 0.1 to about 60 mg/kg/day, from about 0.1 to about 50 mg/kg/day, from about 0.1 to about 25 mg/kg/day, from about 0.1 to about 20 mg/kg/day, from about 0.1 to about 15 mg/kg/day, from about 0.1 to about 10 mg/kg/day, or from about 0.1 to about 5 mg/kg/day. In one embodiment, the therapeutically effective amount is ranging from about 0.1 to about 100 mg/kg/day. In another embodiment, the therapeutically effective amount is ranging from about 0.1 to about 50 mg/kg/day. In yet another embodiment, the therapeutically effective amount is ranging from about 0.1 to about 60 mg/kg/day. In yet another embodiment, the therapeutically effective amount is ranging from about 0.1 to about 50 mg/kg/day. In yet another embodiment, the therapeutically effective amount is ranging from about 0.1 to about 25 mg/kg/day. In yet another embodiment, the therapeutically effective amount is ranging from about 0.1 to about 20 mg/kg/day. In yet another embodiment, the therapeutically effective amount is ranging from about 0.1 to about 15 mg/kg/day. In yet another embodiment, the therapeutically effective amount is ranging from about 0.1 to about 10 mg/kg/day. In still another embodiment, the therapeutically effective amount is ranging from about 0.1 to about 5 mg/kg/day.

It is understood that the administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both. For example, a dose of 1 $mg/m^2/day$ for a 65 kg human is approximately equal to 58 mg/kg/day.

Depending on the disease to be treated and the subject's condition, a compound provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein may be formulated in suitable dosage unit with a pharmaceutically acceptable excipient, carrier, adjuvant, or vehicle, appropriate for each route of administration.

In one embodiment, a compound provided herein is administered orally. In another embodiment, a compound provided herein is administered parenterally. In yet another embodiment is administered intravenously. In yet another embodiment, a compound provided herein is administered intramuscularly. In yet another embodiment, a compound provided herein is administered subcutaneously. In still another embodiment, a compound provided herein is administered topically.

A compound provided herein can be delivered as a single dose such as, e.g., a single bolus injection, or oral tablets or pills; or over time such as, e.g., continuous infusion over time or divided bolus doses over time. A compound provided herein can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A compound provided herein can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days.

In certain embodiments, a compound provided herein is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

A compound provided herein can also be combined or used in combination with other therapeutic agents useful in the treatment and/or prevention of a condition, disorder, or disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 50 minutes, 65 minutes, 1 hour, 2 hours, 6 hours, 6 hours, 12 hours, 26 hours, 68 hours, 72 hours, 96 hours, 1 week, 2 weeks, 5 weeks, 6 weeks, 8 weeks, or 12 weeks before), concomitantly with, or subsequent to (e.g., 5 minutes, 15 minutes, 50 minutes, 65 minutes, 1 hour, 2 hours, 6 hours, 12 hours, 26 hours, 68 hours, 72 hours, 96 hours, 1 week, 2 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein is independent of the route of administration of a second therapy. In one embodiment, a compound provided herein is administered orally. In another embodiment, a compound provided herein is administered intravenously. Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, provided herein is a method of inducing apoptosis in a cell, comprising contacting the cell with an effective amount of a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method of modulating the activity of nuclear receptor subfamily 4 group A member 1 in a cell, comprising contacting the cell with an effective amount of a compound of Formula (I), or a diastereomer, a mixture of two or more diastereomers, a tautomer, a mixture of two or more tautomers, or an isotopic variant thereof, or a pharmaceutically acceptable salt, solvate, hydrate, or prodrug thereof.

In certain embodiments, the cell is a cancerous cell. In certain embodiments, the cell is a cell of breast cancer, cervical cancer, colorectal cancer, gastric cancer, hepatic cancer, lymphoma, lung cancer, melanoma, ovarian cancer, pancreatic cancer, or prostate cancer. In certain embodiments, the cell is a cell of breast cancer, colorectal cancer, hepatic cancer, lung cancer, ovarian cancer, pancreatic cancer, or prostate cancer. In certain embodiments, the cell is a cell of breast cancer, colorectal cancer, ovarian cancer, pancreatic cancer, or prostate cancer.

A compound provided herein can also be provided as an article of manufacture using packaging materials well known to those of skill in the art. See, e.g., U.S. Pat. Nos. 5,525,907; 5,052,558; and 5,055,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein is a kit which, when used by a medical practitioner, can simplify the administration of an appropriate amount of a compound provided herein as an active ingredient to a subject. In certain embodiments, the kit provided herein includes a container and a dosage form of a compound provided herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); mmol (millimoles); h (hour or hours); AcOH (acetic acid); DCM (dichloromethane); DMF (dimethylformamide); DMSO (dimethyl sulfoxide); MeOH (methanol);

EtOAc (ethyl acetate); EtOH (ethanol); PE (petroleum ether); t-BuOH (tert-butanol); THF (tetrahydrofuran); DIPEA (N,N-diisopropylethylamine); DAST (diethylamino-sulfur trifluoride); DBU (1,8-diazabicyclo[5.4.0]undec-7-ene); DCC (dicyclohexyl carbodiimide); DMAP (4-dimeth-ylaminopyridine); TEA or Et$_3$N (triethylamine); MeONa (sodium methoxide); PDC (pyridinium dichromate); PyBOP ((benzotriazol-1-yloxy)tripyrrolidinophosphonium hexafluorophosphate); HRMS (high resolution mass spectrometry); LCMS (liquid chromatography-mass spectrometry); and NMR (nuclear magnetic resonance).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1

Preparation of (2R,4aS,6aS,9S,12bR,14aS,14bR)-9-methoxy-2,4a,6a,9,12b,14a-hexamethyl-10,11-di-oxo-1,2,3,4,4a,5,6,6a,9,10,11,12b,13,14,14a,14b-hexadecahydropicene-2-carboxylic acid A1

A1

Compound A1 was synthesized as shown in Scheme 1.

Scheme 1

1

-continued

A1

To a solution of celastrol 1 (200 mg, 0.44 mmol) in MeOH (20 mL) was added MeONa (190 μL, 30 wt % in methanol, ρ=0.97 g/mL). After stirred for 2.5 h in the presence of air, the reaction was quenched with 1N HCl (40 mL) and concentrated in vacuo. The resulting mixture was extracted with ethyl acetate (3×20 mL) and washed by brine (3×15 mL). The organic layers were combined, dried over anhydrous sodium sulfate, and concentrated in vacuo to yield a crude product, which was purified by flash column chromatography on silica gel (ethyl acetate/hexane=1:4) to afford compound A1 in 56% yield. $^1$H NMR (600 MHz, DMSO-d$_6$) δ 12.07 (br. s., 1H), 6.47 (d, J=6.60 Hz, 1H), 6.40 (s, 1H), 6.19 (d, J=6.60 Hz, 1H), 3.17 (s, 3H), 2.32 (d, J=15.59 Hz, 1H), 2.12 (d, J=8.44 Hz, 1H), 2.04 (d, J=13.75 Hz, 1H), 1.94-2.01 (m, 2H), 1.77-1.85 (m, 1H), 1.69-1.73 (m, 1H), 1.62-1.66 (m, J=7.90 Hz, 2H), 1.52-1.55 (m, 2H), 1.48-1.52 (m, 1H), 1.44 (s, 3H), 1.42 (s, 3H), 1.30 (d, J=4.58 Hz, 1H), 1.28 (s, 1H), 1.20 (s, 3H), 1.11 (s, 3H), 1.06 (s, 3H), 0.85-0.90 (m, 1H), 0.68 (s, 3H); $^{13}$C NMR (151 MHz, DMSO-d$_6$) δ 195.9, 181.5, 179.4, 174.2, 162.3, 130.6, 126.7, 122.7, 116.0, 86.2, 53.5, 44.3, 43.6, 42.3, 39.4, 37.8, 36.1, 35.4, 34.4, 32.6, 32.4, 31.3, 30.22, 30.17, 29.4, 29.0, 28.0, 26.3, 22.3, 18.4; HRMS (ESI) m/z: calcd for C$_{30}$H$_{41}$O$_5$$^+$ [M+H]$^+$: 481.2949, found: 481.2950.

Example 2

Preparation of (2R,4aS,6aS,9S,12bR,14aS,14bR)-9-(methoxy-d$_3$)-2,4a,6a,9,12b,14a-hexamethyl-10,11-dioxo-1,2,3,4,4a,5,6,6a,9,10,11,12b,13,14,14a,14b-hexadecahydropicene-2-carboxylic acid A2

A2

To a solution of celastrol 1 (100 mg, 0.22 mmol) in CD$_3$OD (2.5 mL) was added MeONa (95 µL, 30 wt. % in methanol, ρ=0.97 g/mL, 2.3 eq.). After stirred for 2.5 h in the presence of air, the reaction was quenched with 1N HCl (15 mL) and concentrated in vacuo. The resulting mixture was extracted with ethyl acetate (3×20 mL) and washed by brine (3×15 mL). The organic layers were combined, dried over anhydrous sodium sulfate, and concentrated in vacuo to yield a crude product, which was purified by flash column chromatography on silica gel (ethyl acetate/hexane=1:4) to afford compound A2 in 50% yield. $^1$H NMR (600 MHz, DMSO-d$_6$) δ 12.07 (br. s., 1H), 6.47 (dd, J=1.28, 6.60 Hz, 1H), 6.40 (d, J=1.30 Hz, 1H), 6.19 (d, J=6.79 Hz, 1H), 2.29-2.36 (m, 1H), 2.11 (d, J=7.89 Hz, 1H), 2.04 (d, J=13.75 Hz, 1H), 1.94-2.01 (m, 1H), 1.77-1.86 (m, 1H), 1.68-1.74 (m, 1H), 1.67 (s, 1H), 1.64-1.65 (m, J=3.50 Hz, 1H), 1.62-1.63 (m, 1H), 1.52-1.56 (m, 3H), 1.48-1.52 (m, 1H), 1.44 (s, 3H), 1.42 (s, 3H), 1.29-1.33 (m, 1H), 1.20 (s, 3H), 1.11 (s, 3H), 1.06 (s, 3H), 0.86-0.90 (m, 1H), 0.68 (s, 3H). $^{13}$C NMR (151 MHz, DMSO-d$_6$) δ 196.0, 181.6, 179.4, 174.2, 162.2, 130.7, 126.7, 122.6, 116.0, 86.2, 44.3, 43.6, 42.3, 39.4, 37.8, 36.1, 35.3, 34.4, 32.6, 32.4, 31.3, 30.23, 30.16, 29.4, 29.0, 28.0, 26.3, 22.3, 18.4; HRMS (ESI) m/z: calcd for C$_{30}$H$_{36}$D$_3$O$_5$$^-$ [M−H]$^-$: 482.2991, found: 482.2987.

Example 3

Preparation of (2R,4aS,6aS,12bR,14aS,14bR)-9-(acetyloxy)-2,4a,6a,9,12b,14a-hexamethyl-10,11-dioxo-1,2,3,4,4a,5,6,6a,9,10,11,12b,13,14,14a,14b-hexadecahydropicene-2-carboxylic acid A3

A3

To a solution of celastrol 1 (100 mg, 0.22 mmol) in AcOH (20 mL) was added lead tetraacetate (98 mg, 0.22 mmol). After stirred for 2 h in the presence of air, the reaction was quenched with saturated sodium bicarbonate (2×15 mL), extracted with ethyl acetate (3×10 mL), and washed with brine (15 mL). The organic layers were combined, dried over anhydrous sodium sulfate, and concentrated in vacuo to yield a crude product, which was purified by flash column chromatography on silica gel (ethyl acetate/hexane=1:4) to afford compound A3 in 25% yield. $^1$H NMR (600 MHz, DMSO-d$_6$) δ 12.11 (br. s., 1H), 6.49 (dd, J=1.47, 6.60 Hz, 1H), 6.48 (d, J=1.50 Hz, 1H), 6.10 (d, J=6.60 Hz, 1H), 2.32 (d, J=15.59 Hz, 1H), 2.12 (s, 3H), 2.07-2.11 (m, 1H), 2.04 (d, J=13.76 Hz, 1H), 1.96 (dt, J=4.03, 13.94 Hz, 1H), 1.75-1.85 (m, 1H), 1.68-1.74 (m, 1H), 1.60-1.67 (m, 3H), 1.54 (s, 3H), 1.47-1.52 (m, 3H), 1.44 (s, 3H), 1.37-1.43 (m, 1H), 1.29-1.34 (m, 1H), 1.26 (dd, J=4.40, 11.55 Hz, 1H), 1.19 (s, 3H), 1.11 (s, 3H), 1.06 (s, 3H), 0.65 (s, 3H); $^{13}$C NMR (151 MHz, DMSO-d$_6$) δ 190.5, 179.5, 177.8, 171.5, 169.3, 162.7, 131.9, 125.7, 122.6, 115.9, 81.0, 44.3, 43.6, 42.3, 39.4, 37.8, 36.1, 35.3, 34.4, 32.5, 32.3, 31.3, 30.3, 30.2, 29.4, 29.0, 28.0, 24.8, 22.1, 20.2, 18.4. HRMS (ESI) m/z: calcd for C$_{31}$H$_{41}$O$_6$$^+$ [M+H]$^+$: 509.2898, found: 509.2898.

Example 4

Preparation of methyl (2R,4aS,6aS,12bR,14aS, 14bR)-9-(1H-indol-3-yl)-2,4a,6a,9,12b,14a-hexamethyl-10,11-dioxo-1,2,3,4,4a,5,6,6a,9,10,11,12b,13, 14,14a,14b-hexadecahydropicene-2-carboxylate A4

A4

To a solution of pristimerin (50 mg, 0.1 mmol) and indole (70 mg, 0.22 mmol) in MeOH (2 mL) was added aq. NaOH (100 µL, 1 mol/L). After stirred for 2 h in the presence of air, the reaction was quenched with 1N HCl (15 mL), extracted with ethyl acetate (3×15 mL), and washed with brine (15 mL). The organic layers were combined, dried over anhydrous sodium sulfate, and concentrated in vacuo to yield a crude product, which was purified by flash column chromatography on silica gel (ethyl acetate/hexane=1:4) to afford compound A4 in 20% yield. $^1$H NMR (600 MHz, DMSO-d$_6$) δ 11.14 (d, J=1.83 Hz, 1H), 7.38 (d, J=8.25 Hz, 1H), 7.31 (d, J=2.57 Hz, 1H), 7.06 (dt, J=1.28, 7.43 Hz, 1H), 6.84-6.87 (m, 1H), 6.81-6.84 (m, 1H), 6.50 (s, 1H), 5.96 (s, 2H), 3.56 (s, 3H), 2.34 (d, J=15.59 Hz, 1H), 2.13-2.19 (m, 1H), 2.07 (d, J=13.75 Hz, 1H), 1.98-2.03 (m, 1H), 1.92-1.97 (m, 1H), 1.79 (s, 3H), 1.74-1.77 (m, 1H), 1.66-1.72 (m, 4H), 1.53 (d, J=8.07 Hz, 1H), 1.50 (s, 3H), 1.42-1.45 (m, 1H), 1.38-1.41 (m, 1H), 1.33-1.37 (m, 1H), 1.18 (s, 3H), 1.14 (s, 3H), 1.06 (s, 3H), 0.90 (d, J=13.57 Hz, 1H), 0.56 (s, 3H); $^{13}$C NMR (151 MHz, DMSO-d$_6$) δ 196.2, 181.3, 178.3, 173.9, 161.8, 137.0, 134.2, 128.8, 125.1, 125.0, 122.6, 121.2, 119.4, 118.8, 116.4, 114.3, 111.9, 54.7, 51.5, 44.1, 43.6, 42.7, 39.9, 37.9, 36.1, 35.9, 34.4, 32.5, 32.3, 31.4, 30.2, 29.5, 29.2, 27.9, 26.6, 23.4, 22.1, 18.0; HRMS (ESI) m/z: calcd for C$_{38}$H$_{45}$NNaO$_4$$^+$ [M+Na]$^+$: 602.3241, found: 602.3236.

Example 5

Example 6

Preparation of methyl (2R,4aS,6aS,9S,12bR,14aS, 14bR)-9-methoxy-2,4a,6a,9,12b,14a-hexamethyl-10, 11-dioxo-1,2,3,4,4a,5,6,6a,9,10,11,12b,13,14,14a, 14b-hexadecahydropicene-2-carboxylate A5

Preparation of 1H-1,2,3-benzotriazol-1-yl (2R,4aS, 6aS,9S,12bR,14aS,14bR)-9-methoxy-2,4a,6a,9,12b, 14a-hexamethyl-10,11-dioxo-1,2,3,4,4a,5,6,6a,9,10, 11,12b,13,14,14a,14b-hexadecahydropicene-2-carboxylate A6

A5

A6

To a solution of compound A1 (100 mg, 0.21 mmol) in DMF (3 mL) were added CH$_3$I (65.3 mg, 28.6 µL, 0.46 mmol, 2.2 eq.) and K$_2$CO$_3$ (58 mg, 0.42 mmol, 2 eq.). After stirred for 40 min, the reaction was quenched with brine (20 mL), diluted with water (10 mL), and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:8) to afford compound A5 (86 mg) in 83% yield. $^1$H NMR (600 MHz, DMSO-d$_6$) δ 6.46 (dd, J=1.28, 6.60 Hz, 1H), 6.40 (d, J=1.10 Hz, 1H), 6.19 (d, J=6.79 Hz, 1H), 3.50 (s, 3H), 3.16 (s, 3H), 2.32 (d, J=15.96 Hz, 1H), 2.09-2.12 (m, 1H), 2.07 (d, J=14.12 Hz, 1H), 1.97-2.02 (m, 1H), 1.92-1.97 (m, 1H), 1.82 (ddd, J=8.16, 11.78, 14.35 Hz, 1H), 1.70 (d, J=8.07 Hz, 1H), 1.66-1.68 (m, 1H), 1.65 (br. s, 1H), 1.51-1.55 (m, J=7.90 Hz, 2H), 1.44 (s, 3H), 1.41 (s, 3H), 1.37 (dd, J=4.49, 14.03 Hz, 1H), 1.32-1.35 (m, 1H), 1.28 (dd, J=3.67, 17.61 Hz, 1H), 1.20 (s, 3H), 1.12 (s, 3H), 1.07 (s, 3H), 0.91 (d, J=13.75 Hz, 1H), 0.51 (s, 3H); $^{13}$C NMR (151 MHz, DMSO-d$_6$) δ 195.9, 181.5, 177.9, 174.1, 162.1, 130.7, 126.6, 122.8, 116.0, 86.3, 53.5, 51.4, 44.2, 43.5, 42.3, 39.8, 37.7, 36.0, 35.4, 34.3, 32.5, 32.2, 31.3, 30.3, 30.1, 29.4, 29.1, 28.0, 26.4, 22.1, 18.0; HRMS (ESI) m/z: calcd for C$_{31}$H$_{43}$O$_5$$^+$ [M+H]$^+$: 495.3105, found: 495.3102.

To a solution of compound A1 (100 mg, 0.208 mmol) and PyBOP (130 mg, 0.25 mmol) in DMF (4 mL) was added DIPEA (54 mg, 69 µL, 0.42 mmol). After stirred for 2 h, the reaction was quenched with brine (15 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:4) to afford compound A6 (102 mg) in 82% yield. $^1$H NMR (600 MHz, DMSO-d$_6$) δ 8.12 (d, J=8.44 Hz, 1H), 7.62-7.68 (m, 1H), 7.57-7.61 (m, 1H), 7.47-7.53 (m, 1H), 6.47 (dd, J=1.10, 6.60 Hz, 1H), 6.43 (d, J=1.28 Hz, 1H), 6.22 (d, J=6.79 Hz, 1H), 3.19 (s, 3H), 2.61 (d, J=16.32 Hz, 1H), 2.22 (d, J=14.49 Hz, 1H), 2.18 (d, J=12.29 Hz, 1H), 2.05-2.11 (m, 1H), 2.01-2.05 (m, 1H), 1.96-2.01 (m, 1H), 1.86-1.92 (m, 1H), 1.85 (d, J=8.99 Hz, 1H), 1.74-1.81 (m, 2H), 1.68 (d, J=7.52 Hz, 1H), 1.65 (s, 3H), 1.56-1.61 (m, 2H), 1.49 (d, J=3.48 Hz, 1H), 1.47 (s, 3H), 1.41 (s, 3H), 1.25 (s, 3H), 1.15 (s, 3H), 1.04 (d, J=12.65 Hz, 1H), 0.87 (s, 3H); $^{13}$C NMR (151 MHz, DMSO-d$_6$) δ 195.4, 181.4, 174.4, 173.7, 161.5, 142.6, 130.9, 129.3, 128.0, 126.3, 125.4, 122.7, 120.0, 116.2, 108.7, 86.2, 53.6, 44.3, 43.3, 42.3, 40.3, 37.9, 35.9, 35.3, 33.9, 32.4, 32.3, 31.2, 30.1, 29.9, 29.5, 29.2, 27.9, 26.7, 22.2, 19.3; HRMS (ESI) m/z: calcd for C$_{36}$H$_{44}$N$_3$O$_5$$^+$ [M+H]$^+$: 598.3275, found: 598.3274.

Example 7

Preparation of (2R,4aS,6aS,9S,12bR,14aS,14bR)-9-
methoxy-N,2,4a,6a,9,12b,14a-heptamethyl-10,11-
dioxo-1,2,3,4,4a,5,6,6a,9,10,11,12b,13,14,14a,14b-
hexadecahydropicene-2-carboxamide A7

Example 8

Preparation of (2R,4aS,6aS,9S,12bR,14aS,14bR)-9-
methoxy-2,4a,6a,9,12b,14a-hexamethyl-10,11-di-
oxo-1,2,3,4,4a,5,6,6a,9,10,11,12b,13,14,14a,14b-
hexadecahydropicene-2-carbonyl fluoride A8

A7

A8

To a solution of compound A1 (600 mg, 1.25 mmol) and PyBOP (780 mg, 1.5 mmol) in DMF (24 mL) were added DIPEA (322.5 mg, 412 µL, 2.5 mmol) and $CH_3NH_2$ (33% in absolutely ethanol, 528 µL, 3.75 mmol). After stirred room temperature for 2 h, the reaction was quenched by brine (50 mL) and extracted with ethyl acetate (3×30 mL). The organic layers were combined, dried over anhydrous sodium sulfate, and concentrated in vacuo to yield a crude product, which was purified by flash column chromatography on silica gel (ethyl acetate/hexane=1:2) to afford compound A7 (545 mg) in 88% yield. $^1H$ NMR (600 MHz, DMSO-$d_6$) δ 7.55 (q, J=4.03 Hz, 1H), 6.46 (dd, J=1.28, 6.60 Hz, 1H), 6.41 (d, J=1.47 Hz, 1H), 6.18 (d, J=6.79 Hz, 1H), 3.16 (s, 3H), 2.45 (d, J=4.40 Hz, 3H), 2.38 (d, J=15.41 Hz, 1H), 2.07-2.11 (m, 1H), 2.05 (d, J=14.67 Hz, 1H), 1.98 (dt, J=3.67, 13.94 Hz, 2H), 1.78-1.84 (m, 1H), 1.74-1.78 (m, 1H), 1.62-1.68 (m, 1H), 1.57-1.62 (m, 1H), 1.54-1.57 (m, 1H), 1.50-1.54 (m, 2H), 1.48 (d, J=7.89 Hz, 1H), 1.43 (s, 3H), 1.41 (s, 3H), 1.27-1.35 (m, 1H), 1.19 (s, 3H), 1.06 (s, 3H), 1.02 (s, 3H), 0.86 (d, J=13.94 Hz, 1H), 0.56 (s, 3H); 13C NMR (151 MHz, DMSO-$d_6$) δ 195.9, 181.5, 177.5, 174.2, 162.5, 130.6, 126.7, 122.7, 115.8, 86.2, 53.4, 44.3, 43.9, 42.3, 39.1, 37.8, 36.2, 35.3, 34.8, 33.2, 32.6, 31.4, 30.7, 30.2, 29.4, 28.8, 28.1, 26.4, 26.0, 22.2, 17.5. HRMS (ESI) m/z: calcd for $C_{31}H_{44}NO_4^+$ [M+H]$^+$: 494.3265, found: 494.3265.

To a solution of compound A1 (100 mg, 0.21 mmol) in dichloromethane (3 mL) at −78° C. was added DAST (300 µL, 2.1 mmol, 10 eq.). After stirred for 1 h at −78° C., the reaction was quenched with ice water (20 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:8) to afford compound A8 (78 mg, yield: 78%). $^1H$ NMR (600 MHz, DMSO-$d_6$) δ 6.46 (dd, J=1.38, 6.69 Hz, 1H), 6.41 (d, J=1.28 Hz, 1H), 6.20 (d, J=6.79 Hz, 1H), 3.16 (s, 3H), 2.23 (d, J=16.14 Hz, 1H), 2.11 (d, J=7.70 Hz, 1H), 1.95-2.00 (m, 1H), 1.89-1.95 (m, 1H), 1.78-1.88 (m, 2H), 1.67-1.72 (m, J=9.00 Hz, 1H), 1.65 (d, J=14.67 Hz, 1H), 1.57 (d, J=8.07 Hz, 1H), 1.54-1.56 (m, J=4.20 Hz, 2H), 1.53 (d, J=4.95 Hz, 1H), 1.48-1.52 (m, 1H), 1.45 (s, 3H), 1.42-1.45 (m, J=3.90 Hz, 1H), 1.42 (s, 3H), 1.30 (s, 3H), 1.21 (s, 3H), 1.09 (s, 3H), 0.99 (d, J=15.22 Hz, 1H), 0.63 (s, 3H); $^{13}C$ NMR (151 MHz, DMSO-$d_6$) δ 195.9, 181.5, 174.0, 167.6 (d, J=370.83 Hz), 161.6, 130.8, 126.5, 122.8, 116.2, 86.3, 53.5, 44.1, 43.2, 42.2, 40.2, 37.8, 35.8, 35.4, 33.7, 32.4, 31.1, 29.99, 29.95, 29.5, 29.4, 29.2, 27.9, 26.4, 22.1, 19.0; HRMS (ESI) m/z: calcd for $C_{30}H_{40}FO_4^+$ [M+H]$^+$: 483.2905, found: 483.2915.

Example 9

Preparation of (2R,4aS,6aS,9S,12bR,14aS,14bR)-9-methoxy-2,4a,6a,9,12b,14a-hexamethyl-10,11-di-oxo-1,2,3,4,4a,5,6,6a,9,10,11,12b,13,14,14a,14b-hexadecahydropicene-2-carboxamide A9

Example 10

Preparation of (2R,4aS,6aS,9S,12bR,14aS,14bR)—N-ethyl-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A10

A9

A10

To a mixture of compound A1 (50 mg, 0.10 mmol), $NH_4Cl$ (16 mg, 0.3 mmol), and PyBOP (62 mg, 0.12 mmol) in DMF (2 mL) was added DIPEA (26 mg, 35 µL, 0.2 mmol). After stirred for 2 h, the reaction was quenched with brine (10 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:2) to afford compound A9 in 44% yield. $^1$H NMR (600 MHz, DMSO-d$_6$) δ 7.19 (s, 1H), 6.64 (s, 1H), 6.47 (dd, J=1.47, 6.60 Hz, 1H), 6.40 (d, J=1.28 Hz, 1H), 6.19 (d, J=6.79 Hz, 1H), 3.16 (s, 3H), 2.37 (d, J=15.41 Hz, 1H), 2.08-2.13 (m, 1H), 2.03-2.08 (m, 1H), 1.94-2.02 (m, 1H), 1.80-1.83 (m, 1H), 1.76-1.80 (m, 1H), 1.62-1.67 (m, 1H), 1.57-1.62 (m, 1H), 1.54-1.57 (m, 1H), 1.53 (d, J=5.14 Hz, 1H), 1.49 (d, J=7.89 Hz, 1H), 1.44 (s, 3H), 1.42 (s, 3H), 1.40 (d, J=1.65 Hz, 1H), 1.26-1.29 (m, 1H), 1.23-1.26 (m, 1H), 1.18-1.21 (m, 3H), 1.06 (s, 6H), 0.80-0.85 (m, 1H), 0.73 (s, 3H); $^{13}$C NMR (151 MHz, DMSO-d$_6$) δ 195.9, 181.5, 179.8, 174.3, 162.7, 130.5, 126.8, 122.6, 115.9, 86.2, 53.4, 44.3, 43.8, 42.4, 39.4, 37.8, 36.2, 35.4, 34.8, 33.3, 32.7, 31.4, 30.7, 30.2, 29.5, 28.8, 28.1, 26.3, 22.3, 18.1. HRMS (ESI) m/z: calcd for $C_{30}H_{42}NO_4^+$ [M+H]$^+$: 480.3108, found: 480.3108.

To a solution of compound A1 (40 mg, 0.083 mmol), PyBOP (52 mg, 0.1 mmol), and DIPEA (22 mg, 30 µL, 0.17 mmol) in DMF (2 mL) at −10° C. was added $CH_3CH_2NH_2$ (150 µL, 0.25 mmol). After warmed up to room temperature and stirred for 2 h, the reaction was quenched with brine (10 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:2) to afford compound A10 in 48% yield. $^1$H NMR (600 MHz, DMSO-d$_6$) δ 7.55 (t, J=5.32 Hz, 1H), 6.45 (dd, J=1.28, 6.60 Hz, 1H), 6.40 (d, J=1.28 Hz, 1H), 6.17 (d, J=6.79 Hz, 1H), 3.16 (s, 3H), 2.91-3.01 (m, 2H), 2.41 (d, J=15.41 Hz, 1H), 2.09 (br. s., 1H), 2.08 (d, J=5.14 Hz, 1H), 1.93-1.98 (m, 1H), 1.79-1.83 (m, 1H), 1.78 (d, J=7.15 Hz, 1H), 1.62-1.66 (m, 1H), 1.59-1.62 (m, 1H), 1.54-1.58 (m, 1H), 1.51-1.54 (m, 2H), 1.47-1.49 (m, 1H), 1.43 (s, 3H), 1.41 (s, 3H), 1.28-1.33 (m, 1H), 1.24-1.28 (m, 1H), 1.19 (s, 3H), 1.06 (s, 3H), 1.03 (s, 3H), 0.93 (t, J=7.24 Hz, 3H), 0.85 (d, J=6.90 Hz, 1H), 0.60 (s, 3H); $^{13}$C NMR (151 MHz, DMSO-d$_6$) δ 195.8, 181.5, 176.7, 174.2, 162.4, 130.6, 126.6, 122 0.6, 115.8, 86.2, 53.5, 44.3, 43.9, 42.3, 39.3, 37.8, 36.2, 35.3, 34.8, 33.6, 33.4, 32.5, 31.4, 30.5, 30.2, 29.4, 28.8, 28.1, 26.5, 22.2, 17.8, 14.5. HRMS (ESI) m/z: calcd for $C_{32}H_{46}NO_4^+$ [M+H]$^+$: 508.3421, found: 508.3421.

Example 11

Example 12

Preparation of benzyl (2R,4aS,6aS,9S,12bR,14aS,
14bR)-9-methoxy-2,4a,6a,9,12b,14a-hexamethyl-10,
11-dioxo-1,2,3,4,4a,5,6,6a,9,10,11,12b,13,14,14a,
14b-hexadecahydropicene-2-carboxylate A11

Preparation of (2R,4aS,9S,6aS,12bR,14aS,14bR)—
N-propyl-9-methoxy-2,4a,6a,9,12b,14a-hexamethyl-
10,11-dioxo-1,2,3,4,4a,5,6,6a,9,10,11,12b,13,14,14a,
14b-hexadecahydropicene-2-carboxamide A12

A11

A12

To a solution of compound A1 (200 mg, 0.42 mmol) and PhCH$_2$Br (109 μL, 157 mg, 0.92 mmol) in DMF (6 mL) was added K$_2$CO$_3$ (116 mg, 0.84 mmol). After stirred at 80° C. for 1 h, the reaction was quenched with water (20 mL), extracted with ethyl acetate (30 mL×3), and washed with brine (20 mL). The organic layers were combined, dried over anhydrous sodium sulfate, and concentrated in vacuo to yield a crude product, which was purified by flash column chromatography on silica gel (ethyl acetate/hexane=1:10) to afford compound A11 in 89% yield. $^1$H NMR (600 MHz, DMSO-d$_6$) δ 7.33-7.43 (m, 2H), 7.33 (s, 2H), 7.28 (d, J=6.60 Hz, 1H), 6.45 (d, J=6.60 Hz, 1H), 6.32 (s, 1H), 6.16 (d, J=6.60 Hz, 1H), 5.05 (d, J=12.65 Hz, 1H), 4.92 (d, J=12.47 Hz, 1H), 3.17 (s, 3H), 2.34 (d, J=15.77 Hz, 1H), 2.10 (d, J=13.57 Hz, 1H), 1.94-2.00 (m, 1H), 1.88-1.94 (m, 1H), 1.74-1.83 (m, 1H), 1.64-1.73 (m, 1H), 1.53-1.61 (m, 2H), 1.45-1.52 (m, 3H), 1.41 (br. s., 3H), 1.40 (br. s., 3H), 1.33-1.38 (m, 1H), 1.25-1.32 (m, 1H), 1.19-1.24 (m, 1H), 1.16 (br. s., 3H), 1.16 (br. s., 3H), 1.06 (s, 3H), 0.91 (d, J=13.57 Hz, 1H), 0.45 (s, 3H); $^{13}$C NMR (151 MHz, DMSO-d$_6$) δ 196.0, 181.4, 177.1, 174.2, 162.2, 135.9, 130.6, 128.5 (2C), 128.1 (2C), 128.0, 126.7, 122.8, 116.0, 86.3, 65.6, 53.5, 44.2, 43.5, 42.2, 39.9, 37.7, 36.0, 35.3, 34.2, 32.3, 32.2, 31.3, 30.2 (2C), 29.4, 28.9, 28.0, 26.4, 22.1, 18.2; HRMS (ESI) m/z: calcd for C$_{37}$H$_{47}$O$_5^+$ [M+H]$^+$: 571.3418, found: 571.3419.

To a solution of compound A1 (100 mg, 0.208 mmol), PyBOP (130 mg, 0.25 mmol), and DIPEA (68.7 μL, 0.416 mmol) in 4 mL DMF at −10° C. was added CH$_3$CH$_2$CH$_2$NH$_2$ (51.2 μL, 0.624 mmol). After warmed up to room temperature and stirred for 2 h, the reaction was quenched with brine (30 mL) and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:4) to afford compound A12 in 49% yield. $^1$H NMR (600 MHz, DMSO-d$_6$) δ 7.55 (t, J=5.50 Hz, 1H), 6.46 (dd, J=1.10, 6.60 Hz, 1H), 6.40 (s, 1H), 6.18 (d, J=6.79 Hz, 1H), 3.17 (s, 3H), 2.90-2.98 (m, 1H), 2.79-2.88 (m, 1H), 2.42 (d, J=15.59 Hz, 1H), 2.11 (d, J=4.77 Hz, 1H), 2.09 (d, J=6.42 Hz, 1H), 1.97 (dt, J=3.48, 13.85 Hz, 1H), 1.80-1.84 (m, 1H), 1.75-1.80 (m, 1H), 1.62-1.67 (m, J=3.90 Hz, 1H), 1.59-1.62 (m, 1H), 1.55-1.59 (m, 1H), 1.54 (d, J=5.50 Hz, 1H), 1.52 (d, J=3.48 Hz, 1H), 1.49 (d, J=7.89 Hz, 1H), 1.44 (s, 3H), 1.42 (s, 3H), 1.35-1.37 (m, 1H), 1.32-1.35 (m, 1H), 1.26-1.31 (m, 2H), 1.19 (s, 3H), 1.06 (s, 3H), 1.04 (s, 3H), 0.85-0.89 (m, 1H), 0.78 (t, J=7.43 Hz, 3H), 0.60 (s, 3H); $^{13}$C NMR (151 MHz, DMSO-d$_6$) 9195.8, 181.5, 176.9, 174.2, 162.4, 130.6, 126.6, 122.6, 115.8, 86.2, 53.4, 44.3, 43.9, 42.3, 40.8, 39.4, 37.7, 36.2, 35.3, 34.8, 33.4, 32.5, 31.4, 30.5, 30.2, 29.4, 28.8, 28.1, 26.4, 22.2, 22.0, 17.8, 11.5; HRMS (ESI) m/z: calcd for C$_{33}$H$_{48}$NO$_4^+$ [M+H]$^+$: 522.3578, found: 522.3578.

Example 13

Preparation of (2R,4aS,6aS,9S,12bR,14aS,14bR)-9-methoxy-N,N,2,4a,6a,9,12b,14a-octamethyl-10,11-dioxo-1,2,3,4,4a,5,6,6a,9,10,11,12b,13,14,14a,14b-hexadecahydropicene-2-carboxamide A13

Example 14

Preparation of (4S,6bS,8aS,11R,12aR,12bS,14aR)-11-(hydroxymethyl)-4-methoxy-4,6b,8a,11,12b,14a-hexamethyl-4,6b,7,8,8a,9,10,11,12,12a,12b,13,14,14a-tetradecahydropicene-2,3-dione A14

A14

Compound A14 was synthesized as shown in Scheme 2.

Scheme 2

A13

To a solution of compound A1 (85 mg, 0.208 mmol), PyBOP (130 mg, 0.25 mmol), and DIPEA (68.7 μL, 0.416 mmol) in DMF (4 mL) at −10° C. was added (CH₃)₂NH (91 μL, 0.624 mmol). After warmed up to room temperature and stirred for 2 h, the reaction mixture was quenched with brine (30 mL) and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:4) to afford compound A13 in 62% yield. $^1$H NMR (600 MHz, CCl₃D) δ 6.51 (dd, J=1.47, 6.60 Hz, 1H), 6.44 (d, J=1.47 Hz, 1H), 6.17 (d, J=6.60 Hz, 1H), 3.30 (s, 3H), 3.16 (br. s., 3H), 2.85 (br. s., 3H), 2.40 (d, J=15.77 Hz, 1H), 2.34 (dd, J=1.83, 13.57 Hz, 1H), 2.09 (dt, J=3.67, 14.03 Hz, 1H), 1.97-2.05 (m, 1H), 1.84 (d, J=6.79 Hz, 1H), 1.80-1.83 (m, 1H), 1.77-1.80 (m, 1H), 1.75-1.77 (m, J=3.30 Hz, 1H), 1.73-1.75 (m, J=9.00 Hz, 1H), 1.70-1.73 (m, 1H), 1.67-1.69 (m, 1H), 1.63-1.67 (m, 1H), 1.57-1.59 (m, 1H), 1.55-1.57 (m, 1H), 1.53-1.55 (m, J=2.60 Hz, 1H), 1.53 (s, 3H), 1.50 (s, 3H), 1.33 (dd, J=3.94, 13.85 Hz, 1H), 1.28-1.31 (m, 1H), 1.28 (s, 3H), 1.26 (s, 3H), 1.13 (s, 3H), 0.95-1.01 (m, 1H); $^{13}$C NMR (151 MHz, CCl₃D) δ 195.9, 181.8, 176.9, 175.3, 163.2, 130.8, 127.5, 123.0, 116.4, 86.5, 54.1, 44.8, 44.6, 42.8, 40.1, 38.4, 36.3, 36.1, 36.0, 34.24, 34.2, 33.2, 31.91, 31.88, 30.9, 30.7, 30.3, 30.0, 28.8, 27.2, 23.1, 18.5; HRMS (ESI) m/z: calcd for $C_{32}H_{46}NO_4^+$ [M+H]$^+$: 508.3421, found: 508.3416.

LiAlH₄

SeO₂

MeONa
MeOH

2

3

4

-continued

A14

Compound 3: To a solution of pristemerin 2 (420 mg, 0.90 mmol) in THF (20 mL) was added LiAlH₄ (3.5 mL, 1 mol/L, 4 eq.). After stirred for 2 h, the reaction was quenched with water (20 mL), acidified with HCl (1 mol/L) to pH 2, and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:4) to afford compound 3 in 95% yield.

Compound 4. To a solution of compound 3 (35 mg, 0.08 mmol) in t-BuOH (2 mL) was added SeO₂ (40 mg, 0.32 mmol, purity=99%). After stirred at 60° C. overnight, the reaction was diluted with ethyl acetate (10 mL), quenched by water (10 mL), and extracted with ethyl acetate (3×10 mL). The organic layers were combined, dried over anhydrous sodium sulfate, and concentrated in vacuo to yield a crude product, which was purified by flash column chromatography on silica gel (ethyl acetate/hexane=1:4) to afford compound 4 in 71% yield.

Compound A14. To a solution of compound 4 (100 mg, 0.083 mmol) in MeOH (2 mL) was added 1N NaOH (200 μL). After stirred for 2 h in the presence of air, the reaction was quenched with 1N HCl (2 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:4) to afford compound A14 in 48% yield. ¹H NMR (600 MHz, DMSO-d₆) δ 6.48 (dd, J=1.28, 6.60 Hz, 1H), 6.39 (d, J=1.47 Hz, 1H), 6.20 (d, J=6.60 Hz, 1H), 6.05 (t, J=3.39 Hz, 1H), 4.46 (t, J=4.58 Hz, 1H), 3.21-3.23 (m, 1H), 3.19-3.21 (m, 1H), 3.17 (s, 3H), 2.96 (dd, J=4.58, 10.09 Hz, 1H), 2.02-2.08 (m, 1H), 1.73 (d, J=4.40 Hz, 1H), 1.71 (br. s., 1H), 1.67-1.69 (m, 1H), 1.66 (d, J=4.03 Hz, 1H), 1.64-1.65 (m, 1H), 1.62-1.64 (m, 2H), 1.58-1.62 (m, 1H), 1.55 (dd, J=5.59, 7.61 Hz, 1H), 1.51 (dd, J=4.13, 7.24 Hz, 1H), 1.44 (s, 3H), 1.42 (s, 3H), 1.36-1.41 (m, 1H), 1.28 (s, 3H), 1.12 (s, 3H), 0.89 (s, 3H), 0.88 (br. s., 1H), 0.79 (s, 3H); ¹³C NMR (151 MHz, DMSO-d₆) δ 195.9, 181.5, 174.1, 163.5, 130.5, 126.7, 122.6, 116.1, 86.3, 69.2, 53.5, 43.7, 42.8, 42.6, 37.8, 36.3, 36.0, 35.3, 32.4, 32.3, 31.9, 30.1, 29.7, 29.4, 29.3, 29.2, 27.5, 26.4, 24.5, 18.7; HRMS (ESI) m/z: calcd for $C_{30}H_{43}O_4^+$ [M+H]⁺: 467.3156, found: 467.3147.

Example 15

Preparation of (2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A15

A15

Compound A15 was synthesized as shown in Scheme 3.

Scheme 3

A1

NaBH₄ →

A15

To a solution of compound A1 (440 mg, 0.92 mmol) in dry THF (10 mL) at −10° C. was added NaBH₄ (17 mg, 0.46 mmol, 0.5 eq.). After stirred at −10° C. for 1 h, the reaction was quenched with 1 mol/L HCl (30 mL), diluted with water (15 mL), and extracted with ethyl acetate (3×15 mL). The organic layers were combined, washed with brine (3×15 mL), dried over anhydrous sodium sulfate, and concentrated in vacuo to yield a crude product, which was purified by flash column chromatography on silica gel (ethyl acetate/hexane=1:4) to afford compound A15 in 81% yield. $^1$H NMR (600 MHz, DMSO-d$_6$) δ 12.04 (br. s., 1H), 6.22 (dd, J=1.10, 6.42 Hz, 1H), 6.06 (d, J=6.60 Hz, 1H), 5.83 (d, J=1.10 Hz, 1H), 5.20 (d, J=4.59 Hz, 1H), 4.41 (d, J=4.40 Hz, 1H), 3.23 (s, 3H), 2.32 (d, J=15.59 Hz, 1H), 2.05 (d, J=13.75 Hz, 1H), 1.93-2.01 (m, 2H), 1.79 (d, J=14.12 Hz, 1H), 1.65-1.69 (m, 1H), 1.62 (dd, J=7.98, 15.68 Hz, 1H), 1.54-1.59 (m, 2H), 1.47-1.53 (m, 3H), 1.37-1.43 (m, 1H), 1.32 (s, 3H), 1.27-1.31 (m, 1H), 1.17 (s, 3H), 1.11 (s, 3H), 1.06 (br. s., 3H), 1.06 (br. s., 3H), 0.85-0.90 (m, 1H), 0.69 (s, 3H); $^{13}$C NMR (151 MHz, DMSO-d$_6$) δ 198.5, 179.4, 169.6, 158.9, 131.6, 123.7, 118.6, 115.7, 81.8, 74.7, 50.4, 43.9, 43.6, 40.4, 39.4, 37.6, 36.1, 34.9, 34.4, 32.6, 32.4, 31.3, 30.21, 30.18, 29.4, 29.0, 28.0, 22.5, 19.8, 18.5; HRMS (ESI) m/z: calcd for C$_{30}$H$_{43}$O$_5$$^+$ [M+H]$^+$: 483.3105, found: 483.3105.

Example 16

Preparation of benzyl (2R,4aS,6aS,9S,10R,12bR, 14aS,14bR)-10-hydroxy-9-methoxy-2,4a,6a,9,12b, 14a-hexamethyl-11-oxo-1,2,3,4,4a,5,6,6a,9,10,11, 12b,13,14,14a,14b-hexadecahydropicene-2-carboxylate A16

A16

To a solution of compound A11 (148 mg, 0.26 mmol) in THF (4 mL) at −10° C. was added NaBH$_4$ (5 mg, 0.13 mmol, 0.5 eq.). After stirred at −10° C. for 1 h, the action was quenched with 1 mol/L HCl (15 mL) and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:10) to afford compound A16 in 65% yield. $^1$H NMR (600 MHz, DMSO-d$_6$) δ 7.34-7.36 (m, 1H), 7.31-7.34 (m, 3H), 7.27-7.31 (m, 1H), 6.20 (dd, J=1.56, 6.51 Hz, 1H), 6.02 (d, J=6.60 Hz, 1H), 5.76 (d, J=1.47 Hz, 1H), 5.23 (d, J=4.59 Hz, 1H), 5.06 (d, J=12.65 Hz, 1H), 4.92 (d, J=12.47 Hz, 1H), 4.40 (d, J=4.40 Hz, 1H), 3.23 (s, 3H), 2.34 (d, J=15.77 Hz, 1H), 2.10 (d, J=13.94 Hz, 1H), 1.97 (ddd, J=4.03, 13.39, 13.40 Hz, 1H), 1.78-1.83 (m, 1H), 1.73-1.78 (m, 1H), 1.64-1.73 (m, 1H), 1.52 (d, J=3.12 Hz, 1H), 1.51 (br. s., 1H), 1.48 (br. s., 1H), 1.47 (br. s., 1H), 1.43-1.47 (m, 1H), 1.38-1.41 (m, 1H), 1.37 (d, J=4.58 Hz, 1H), 1.33-1.36 (m, 1H), 1.28 (s, 3H), 1.15 (s, 3H), 1.13 (s, 3H), 1.06 (s, 3H), 1.04 (s, 3H), 0.90 (d, J=13.75 Hz, 1H), 0.47 (s, 3H); $^{13}$C NMR (151 MHz, DMSO-d$_6$) δ 198.9, 177.6, 169.9, 159.2, 136.4, 132.1, 128.9 (2C), 128.5 (2C), 128.4, 124.1, 119.3, 116.2, 82.3, 75.2, 66.0, 50.9, 44.3, 43.9, 40.7, 40.3, 37.9, 36.5, 35.3, 34.7, 32.8, 32.7, 31.7, 30.64, 30.59, 29.9, 29.4, 28.4, 22.8, 20.3, 18.7; HRMS (ESI) m/z: calcd for C$_{37}$H$_{49}$O$_5$$^+$ [M+H]$^+$: 573.3575, found: 573.3575; calcd for C$_{37}$H$_{48}$NaO$_5$$^+$ [M+Na]$^+$: 595.3394, found: 573.3394.

Example 17

Preparation of (2R,4aS,6aS,9S,10R,12bR,14aS, 14bR)-10-hydroxy-9-methoxy-N,2,4a,6a,9,12b,14a-heptamethyl-11-oxo-1,2,3,4,4a,5,6,6a,9,10,11,12b, 13,14,14a,14b-hexadecahydropicene-2-carboxamide A17

A17

A solution of compound A15 (65 mg, 0.135 mmol), PyBOP (84 mg, 0.162 mmol) and DIPEA (45 μL, 0.27 mmol) in DMF (4 mL) was stirred at −10° C. for 30 min, followed by addition of CH$_3$NH$_2$ (19 μL, 0.405 mmol). The reaction mixture was then stirred at room temperature for 2 h, quenched with brine (30 mL), and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:2) to afford compound A17 in 89% yield. $^1$H NMR (600 MHz, DMSO-d$_6$) δ 7.54 (d, J=4.40 Hz, 1H), 6.21 (dd, J=1.28, 6.42 Hz, 1H), 6.04 (d, J=6.42 Hz, 1H), 5.84 (d, J=1.47 Hz, 1H), 5.19 (d, J=4.59 Hz, 1H), 4.42 (d, J=4.58 Hz, 1H), 3.23 (s, 3H), 2.46 (d, J=4.40 Hz, 3H), 2.38 (d, J=15.41 Hz, 1H), 2.05 (d, J=14.31 Hz, 1H), 1.93-2.01 (m, 2H), 1.76-1.83 (m, 1H), 1.73 (d, J=6.24 Hz, 1H), 1.52-1.61 (m, 3H), 1.49 (dd, J=3.12, 9.72 Hz, 2H), 1.46 (d, J=7.70 Hz, 1H), 1.36-1.42 (m, 1H), 1.32-1.35 (m, J=4.20 Hz, 1H), 1.31 (s, 3H), 1.15 (s, 3H), 1.06 (s, 6H), 1.02 (s, 3H), 0.84-0.89 (m, 1H), 0.57 (s, 3H); $^{13}$C NMR (151 MHz, DMSO-d$_6$) δ 198.5, 177.5, 169.6, 159.1, 131.5, 123.7, 118.6, 115.6, 81.8, 74.6, 50.4, 43.92, 43.88, 40.4, 39.4, 37.5, 36.2, 34.9, 34.8, 33.3, 32.7, 31.4, 30.7, 30.3, 29.4, 28.8, 28.0, 26.1, 22.5, 19.9, 17.6; HRMS (ESI) m/z: calcd for C$_{31}$H$_{46}$NO$_4$$^+$ [M+H]$^+$: 496.3421, found: 496.3421.

Example 18

Preparation of (3R,4S,6bS,8aS,11R,12aR,12bS,
14aR)-3-hydroxy-11-(hydroxymethyl)-4-methoxy-4,
6b,8a,11,12b,14a-hexamethyl-2,3,4,6b,7,8,8a,9,10,
11,12,12a,12b,13,14,14a-hexadecahydropicen-2-one
A18

Example 19

Preparation of (2R,4aS,6aS,9S,10R,12bR,14aS,
14bR)-10-hydroxy-9-methoxy-2,4a,6a,9,12b,14a-
hexamethyl-11-oxo-1,2,3,4,4a,5,6,6a,9,10,11,12b,13,
14,14a,14b-hexadecahydropicene-2-carbaldehyde
A19

A19

Compound A19 was synthesized as shown in Scheme 4.

Scheme 4

To a solution of compound A14 (250 mg, 0.54 mmol) in THF (6 mL) at −10° C. was added NaBH$_4$ (10.3 mg, 0.27 mmol, 0.5 eq.). After stirred at −10° C. for 1 h, the reaction was quenched with 1 mol/L HCl (25 mL) and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:2) to afford compound A18 in 44% yield. $^1$H NMR (600 MHz, DMSO-d$_6$) δ 6.23 (d, J=6.42 Hz, 1H), 6.06 (d, J=6.42 Hz, 1H), 5.82 (s, 1H), 5.19 (br. s., 1H), 4.44 (br. s., 1H), 4.41 (s, 1H), 3.24 (s, 3H), 3.20 (d, J=10.27 Hz, 1H), 2.96 (d, J=10.27 Hz, 1H), 1.88-1.96 (m, 1H), 1.69-1.73 (m, 1H), 1.67-1.69 (m, J=1.70 Hz, 1H), 1.65-1.67 (m, J=2.80 Hz, 1H), 1.65 (d, J=8.44 Hz, 1H), 1.62-1.64 (m, 1H), 1.60 (d, J=6.97 Hz, 1H), 1.56-1.59 (m, J=4.00 Hz, 1H), 1.53 (d, J=6.79 Hz, 1H), 1.47-1.52 (m, 1H), 1.32-1.36 (m, J=4.20 Hz, 1H), 1.31 (s, 3H), 1.27-1.31 (m, 1H), 1.24 (s, 3H), 1.22-1.24 (m, 1H), 1.19-1.22 (m, 1H), 1.11 (s, 3H), 1.07 (s, 3H), 0.89 (s, 3H), 0.85 (d, J=12.84 Hz, 1H), 0.79 (s, 3H); $^{13}$C NMR (151 MHz, DMSO-d$_6$) δ 198.5, 169.5, 160.1, 131.5, 123.7, 118.5, 115.9, 81.9, 74.8, 69.2, 50.4, 43.2, 42.7, 40.6, 37.6, 36.3, 36.1, 34.7, 32.43, 32.39, 31.9, 30.1, 29.7, 29.34, 29.25, 29.1, 27.6, 24.8, 19.8, 18.8; HRMS (ESI) m/z: calcd for C$_{30}$H$_{45}$O$_4$$^+$ [M+H]$^+$: 469.3312, found: 469.3309; calcd for C$_{30}$H$_{44}$NaO$_4$$^+$ [M+Na]$^+$: 491.3132, found: 491.3128.

To a solution of compound A18 (65 mg, 0.14 mmol) in DCM (4 mL) were added PDC (pyridinium dichromate) (104 mg, 0.27 mmol) and 3,5-dimethylpyrazole (13 mg, 0.14 mmol). After stirred for 2 h, the reaction mixture was filtered through celite and washed by DCM three times. The filtrate was concentrated in vacuo and purified by flash column chromatography on silica gel (ethyl acetate/hexane=1:8) to afford compound A19 in 19% yield. $^1$H NMR (600 MHz, DMSO-d$_6$) δ 9.35 (s, 1H), 6.21 (d, J=6.42 Hz, 1H), 6.04 (d, J=6.42 Hz, 1H), 5.82 (s, 1H), 5.21 (d, J=4.40 Hz, 1H), 4.39 (d, J=3.67 Hz, 1H), 3.22 (s, 3H), 2.15 (d, J=15.77 Hz, 1H), 1.97-2.02 (m, 1H), 1.93-1.97 (m, 1H), 1.76-1.82 (m, 1H), 1.74-1.76 (m, J=6.40 Hz, 1H), 1.72-1.74 (m, J=9.00 Hz, 1H), 1.69-1.72 (m, J=8.40 Hz, 1H), 1.61-1.65 (m, 1H), 1.57-1.61 (m, 1H), 1.54 (d, J=8.25 Hz, 1H), 1.46-1.51 (m, 1H), 1.43 (dd, J=4.95, 13.75 Hz, 1H), 1.38 (t, J=5.14 Hz, 1H), 1.34-1.37 (m, 1H), 1.33 (s, 3H), 1.16 (s, 3H), 1.07 (s, 3H), 1.06 (s, 3H), 0.89 (s, 3H), 0.86 (d, J=6.42 Hz, 1H), 0.49 (s, 3H); $^{13}$C NMR (151 MHz, DMSO-d$_6$) δ 205.9, 198.5, 169.6, 158.5, 131.7, 123.7, 118.7, 115.8, 81.8, 74.7, 50.4, 44.0, 43.8, 43.1, 40.3, 37.8, 36.1, 35.2, 34.1, 32.7, 31.2, 30.1, 29.3, 28.5, 27.8, 26.9, 25.7, 22.3, 19.8, 19.7; HRMS (ESI) m/z: calcd for C$_{30}$H$_{43}$O$_4$$^+$ [M+H]$^+$: 467.3156, found: 467.3150.

Example 20

Preparation of methyl (2R,4aS,6aS,9S,10R,12bR, 14aS,14bR)-10-hydroxy-9-methoxy-2,4a,6a,9,12b, 14a-hexamethyl-11-oxo-1,2,3,4,4a,5,6,6a,9,10,11, 12b,13,14,14a,14b-hexadecahydropicene-2-carboxylate A20

A20

To a mixture of compound A15 (215 mg, 0.45 mmol) and K$_2$CO$_3$ (123.5 mg, 0.89 mmol) in DMF (5 mL) was added CH$_3$I (42 μL, 0.66 mmol). After stirred for 3 h, the reaction was quenched with brine (20 mL) and extracted with ethyl acetate (3×15 mL). The organic layers were combined, washed with brine (2×10 mL), dried over anhydrous sodium sulfate, and concentrated in vacuo to yield a crude product, which was purified by flash column chromatography on silica gel (ethyl acetate/hexane=1:8) to afford compound A20 (162 mg) in 75% yield. $^1$H NMR (600 MHz, DMSO-d$_6$) δ 6.21 (dd, J=1.56, 6.51 Hz, 1H), 6.05 (d, J=6.60 Hz, 1H), 5.83 (d, J=1.47 Hz, 1H), 5.20 (br. s., 1H), 4.40 (s, 1H), 3.51 (s, 3H), 3.23 (s, 3H), 2.31 (d, J=15.59 Hz, 1H), 2.07 (d, J=13.94 Hz, 1H), 1.93-2.00 (m, 2H), 1.76-1.83 (m, 1H), 1.67 (dd, J=8.16, 15.86 Hz, 1H), 1.56-1.62 (m, 3H), 1.46-1.53 (m, 3H), 1.38-1.43 (m, 1H), 1.33-1.37 (m, 1H), 1.32 (s, 3H), 1.16 (s, 3H), 1.12 (s, 3H), 1.06 (s, 3H), 1.06 (s, 3H), 0.91 (d, J=13.75 Hz, 1H), 0.52 (s, 3H); $^{13}$C NMR (151 MHz, DMSO-d$_6$) δ 198.5, 177.9, 169.5, 158.7, 131.6, 123.7, 118.7, 115.8, 81.8, 74.7, 51.4, 50.4, 43.9, 43.5, 40.3, 39.8, 37.5, 36.1, 34.9, 34.4, 32.5, 32.3, 31.3, 30.3, 30.1, 29.4, 29.1, 27.9, 22.4, 19.9, 18.1; HRMS (ESI) m/z: calcd for C$_{31}$H$_{45}$O$_5$$^+$ [M+H]$^+$: 497.3262, found: 497.3253.

Example 21

Preparation of (2R,4aS,6aR,9S,10R,12bR,14aS, 14bR)-10-hydroxy-9-methoxy-2,4a,6a,9,12b,14a-hexamethyl-11-oxo-1,2,3,4,4a,5,6,6a,6b,7,8,8a,9,10, 11,12b,13,14,14a,14b-icosahydropicene-2-carboxylic acid A21

A21

Compound A21 was synthesized as shown in Scheme 5.

Scheme 5

A15

A21

Compound A15 (897 mg, 1.86 mmol) in MeOH (18 mL) was hydrogenated at room temperature with a balloon of hydrogen for 12 h in the presence of 10% Pd/C (0.5 eq.). The reaction mixture was filtered through celite and washed by MeOH three times. The filtrate was concentrated in vacuo to yield a crude product, which was purified by flash column chromatography on silica gel (ethyl acetate/hexane=1:4) to afford compound A21 in 51% yield. $^1$H NMR (600 MHz, DMSO-$d_6$) δ 12.12 (br. s, 1H), 5.82 (d, J=2.75 Hz, 1H), 4.34 (s, 1H), 3.07-3.14 (m, 1H), 2.19-2.27 (m, 1H), 2.03 (d, J=13.57 Hz, 1H), 1.95-2.00 (m, 1H), 1.90-1.95 (m, 1H), 1.87 (dd, J=7.34, 11.74 Hz, 1H), 1.74-1.79 (m, 1H), 1.71 (d, J=14.12 Hz, 1H), 1.62-1.69 (m, 2H), 1.58 (d, J=12.47 Hz, 1H), 1.53-1.56 (m, 1H), 1.51-1.53 (m, 1H), 1.47-1.51 (m, 1H), 1.41-1.46 (m, 2H), 1.36-1.41 (m, 1H), 1.32-1.36 (m, 1H), 1.31 (d, J=14.86 Hz, 1H), 1.26-1.29 (m, 2H), 1.25 (d, J=4.77 Hz, 1H), 1.16-1.21 (m, 1H), 1.11 (s, 3H), 1.09 (s, 3H), 1.04 (s, 3H), 0.94 (s, 3H), 0.87 (s, 3H), 0.85 (d, J=7.15 Hz, 1H), 0.76 (s, 3H); $^{13}$C NMR (151 MHz, DMSO-$d_6$) δ 199.9, 179.65, 179.58, 118.8, 82.0, 76.5, 49.4, 44.2, 39.7, 39.5, 39.2, 38.4, 38.3, 37.2, 35.9, 35.7, 33.6, 32.1, 31.5, 29.91, 29.89, 29.4, 29.3, 27.9, 25.4, 17.6, 16.7, 16.2, 15.1, 12.8; HRMS (ESI) m/z: calcd for $C_{30}H_{45}O_5^-$ [M−H]$^-$: 485.3272, found: 485.3272.

Example 22

Preparation of methyl (2R,4aS,6aR,9S,10R,12bR, 14aS,14bR)-10-hydroxy-9-methoxy-2,4a,6a,9,12b, 14a-hexamethyl-11-oxo-1,2,3,4,4a,5,6,6a,6b,7,8,8a, 9,10,11,12b,13,14,14a,14b-icosahydropicene-2-carboxylate A22

A22

To a solution of compound A21 (19 mg, 0.2 mmol) in DMF (3 mL) were added CH$_3$I (2.2 eq.) and K$_2$CO$_3$ (2 eq.). After stirred for 45 min, the reaction was quenched with brine (10 mL), diluted with water (10 mL), and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:8) to afford compound A22 in 60% yield. $^1$H NMR (600 MHz, DMSO-$d_6$) δ 7.27 (s, 1H), 6.02 (d, J=2.9 Hz, 1H), 4.37 (d, J=2.4 Hz, 1H), 3.82 (d, J=2.4 Hz, 1H), 3.61 (s, 3H), 3.44 (s, 3H), 2.89-2.94 (m, 1H), 2.33 (d, J=15.2 Hz, 1H), 2.18 (d, J=14.1 Hz, 1H), 2.03 (td, J=14.2, 4.0 Hz, 1H), 1.95 (ddd, J=13.8, 9.6, 4.7 Hz, 1H), 1.82 (dd, J=12.1, 7.3 Hz, 1H), 1.79-1.84 (m, 1H), 1.66-1.76 (m, 3H), 1.56-1.61 (m, 3H), 1.50-1.55 (m, 2H), 1.32-1.39 (m, 4H), 1.22-1.25 (m, 1H), 1.18 (s, 3H), 1.17 (s, 3H), 1.07 (s, 3H), 0.98 (s, 3H), 0.92 (s, 3H), 0.76 (s, 3H); $^{13}$C NMR (151 MHz, DMSO-$d_6$) δ 199.8, 181.8, 179.1, 118.8, 83.0, 78.0, 51.6, 50.8, 44.8, 41.7, 40.6, 40.2, 39.2, 38.8, 38.0, 36.2, 35.9, 34.3, 32.4, 31.7, 30.6, 30.3, 30.0, 29.7, 28.4, 25.9, 18.0, 16.7, 16.6, 15.4, 12; HRMS (ESI) m/z: calcd for $C_{31}H_{49}O_5^+$ [M+H]$^+$: 501.3575, found: 501.3566.

Example 23

Preparation of (3R,4S,6bS,8aS,11R,12aR,12bS, 14aR)-4-methoxy-4,6b,8a,11,12b,14a-hexamethyl-11-(methylcarbamoyl)-2-oxo-2,3,4,6b,7,8,8a,9,10, 11,12,12a,12b,13,14,14a-hexadecahydropicen-3-yl butyrate A23

A23

To a solution of compound A17 (35 mg, 0.07 mmol) and 4-DMAP (7.9 mg, 0.07 mmol) in THF (3.5 mL) were added C$_3$H$_7$COCl (73 μL, 0.7 mmol, 10 eq.) and TEA (200 μL, 1.4 mmol, 20 eq.). After stirred overnight, the reaction was quenched with a saturated ammonium chloride solution (12 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:2) to afford compound A23 (12 mg) in 31% yield. $^1$H NMR (600 MHz, DMSO-$d_6$) δ 7.54 (q, J=3.97 Hz, 1H), 6.27 (dd, J=1.56, 6.51 Hz, 1H), 6.08 (d, J=6.60 Hz, 1H), 5.89 (d, J=1.47 Hz, 1H), 5.65 (s, 1H), 3.13 (s, 3H), 2.46 (d, J=4.40 Hz, 3H), 2.43 (t, J=7.06 Hz, 2H), 2.38 (d, J=15.59 Hz, 1H), 2.06 (d, J=14.12 Hz, 1H), 1.98-2.02 (m, 1H), 1.94-1.98 (m, 1H), 1.77-1.83 (m, 1H), 1.70-1.77 (m, 1H), 1.62-1.66 (m, 1H), 1.59-1.62 (m, 1H), 1.57-1.59 (m, 1H), 1.52-1.57 (m, J=7.20, 14.90 Hz, 2H), 1.48-1.52 (m, J=3.70, 7.20 Hz, 2H), 1.46 (d, J=8.07 Hz, 1H), 1.40 (d, J=13.75 Hz, 1H), 1.33 (s, 3H), 1.27-1.32 (m, 1H), 1.21 (s, 3H), 1.16 (s, 3H), 1.05 (s, 3H), 1.02 (s, 3H), 0.95 (t, J=7.43 Hz, 3H), 0.86 (dt, J=1.74, 7.38 Hz, 1H), 0.58 (s, 3H); $^{13}$C NMR (151 MHz, DMSO-$d_6$) δ 191.9, 177.5, 171.8, 170.4, 160.3, 130.1, 124.9, 118.6, 115.6, 80.0, 74.7, 50.6, 44.0, 43.9, 40.8, 37.7, 36.2, 35.3, 35.21, 35.17, 34.8, 33.3, 32.8, 31.4, 30.7, 30.3, 29.4, 28.8, 28.0, 26.0, 22.4, 21.4, 18.1, 17.5, 13.3; HRMS (ESI) m/z: calcd for $C_{35}H_{52}NO_5^+$ [M+H]$^+$: 566.3840, found: 566.3837; $C_{35}H_{51}NaNO_5^+$ [M+Na]$^+$: 588.3659, found: 588.3655.

Example 24

Preparation of methyl (2R,4aS,6aS,9S,10R,12bR,
14aS,14bR)-10-(butyryloxy)-9-methoxy-2,4a,6a,9,
12b,14a-hexamethyl-11-oxo-1,2,3,4,4a,5,6,6a,9,10,
11,12b,13,14,14a,14b-hexadecahydropicene-2-
carboxylate A24 and methyl (2R,4aS,6aS,9S,10S,
12bR,14aS,14bR)-10-(butyryloxy)-11-hydroxy-9-
methoxy-2,4a,6a,9,12b,14a-hexamethyl-1,2,3,4,4a,5,
6,6a,9,10,11,12b,13,14,14a,14b-
hexadecahydropicene-2-carboxylate A25

A24

A25

Compounds A24 and A25 were synthesized as shown in
Scheme 6.

Scheme 6

A20

-continued

A24

A25

Compound A24. To a solution of compound A20 (75 mg,
0.15 mmol) and 4-DMAP (16.8 mg, 0.15 mmol) in THF (3
mL) were added n-butoyl chloride ($C_3H_7COCl$) (78.3 µL,
0.75 mmol) and TEA (312 µL, 2.25 mmol). After stirred
overnight, the reaction was quenched with a saturated
ammonium chloride solution (12 mL) and extracted with
ethyl acetate (3×15 mL). The organic layers were combined,
dried over anhydrous sodium sulfate, and concentrated in
vacuo to yield a crude product, which was purified by flash
column chromatography on silica gel (ethyl acetate/
hexane=1:10) to afford compound A24 in 74% yield. HRMS
(ESI) m/z: calcd for $C_{35}H_{51}O_6^+$ [M+H]$^+$: 567.3680, found:
567.3672.

Compound A25. To a solution of compound A24 (40 mg,
0.07 mmol) and $CeCl_3·7H_2O$ (26.1 mg, 0.07 mmol) in
MeOH (1.4 mL) at −10° C. was added $NaBH_4$ (13.3, 0.35
mmol). After stirred at −10° C. for 30 min, the reaction was
quenched with 1 mol/L HCl (14 mL) and extracted with
ethyl acetate (3×15 mL). The organic layers were combined,
dried over anhydrous sodium sulfate, and concentrated in
vacuo to yield a crude product, which was purified by flash
column chromatography on silica gel (ethyl acetate/
hexane=1:10) to afford compound A25 (17 mg) in 43%
yield. $^1$H NMR (600 MHz, DMSO-d$_6$) δ 5.90 (s, 2H), 5.45
(d, J=2.93 Hz, 1H), 5.17 (d, J=7.70 Hz, 1H), 4.31 (br. s., 1H),
3.62 (s, 3H), 3.18 (s, 3H), 2.44-2.50 (m, 1H), 2.42-2.44 (m,
1H), 2.40-2.42 (m, 1H), 2.20 (d, J=14.12 Hz, 1H), 2.02-2.12
(m, 1H), 1.84-1.89 (m, 1H), 1.78-1.84 (m, 1H), 1.74 (s, 1H),
1.71-1.73 (m, 2H), 1.67-1.71 (m, 2H), 1.55-1.60 (m, 1H),
1.53-1.55 (m, 1H), 1.50-1.53 (m, 1H), 1.46-1.50 (m, 1H),
1.41-1.46 (m, 1H), 1.38 (dt, J=4.49, 14.08 Hz, 1H), 1.28 (s,
6H), 1.17 (s, 6H), 1.07 (s, 3H), 0.99 (t, J=7.43 Hz, 3H), 0.95
(d, J=14.31 Hz, 1H), 0.62 (s, 3H); $^{13}$C NMR (151 MHz,
DMSO-d$_6$) δ 178.9, 174.4, 156.0, 149.7, 130.4, 120.9, 118.9,
115.6, 78.4, 74.9, 72.9, 51.6, 50.4, 44.2, 43.8, 40.4, 39.2,
37.6, 36.6, 36.5, 36.4, 34.8, 33.7, 32.8, 31.5, 30.9, 30.5, 29.9, 29.8, 28.5, 23.3, 21.7, 18.5, 18.5, 13.6; HRMS (ESI) m/z: calcd for $C_{35}H_{52}NaO_6^+$ [M+Na]$^+$: 591.3656, found: 591.3644.

Example 25

Preparation of methyl (2R,4aS,6aS,9S,12bR,14aS, 14bR)-10-hydroxy-9-methoxy-2,4a,6a,9,12b,14a-hexamethyl-10-(methylamino)-11-oxo-1,2,3,4,4a,5, 6,6a,9,10,11,12b,13,14,14a,14b-hexadecahydropicene-2-carboxylate A26

A26

Compound A26 was synthesized as shown in Scheme 7.

Scheme 7

To a solution of compound A5 (100 mg, 0.2 mmol) in toluene (4 mL) were added $CH_3NH_2$ (112.8 μL, 0.8 mmol, 4 eq., 33% in absolutely ethanol) and TEA (278 μL, 10 eq.)

at room temperature, followed by addition of $TiCl_4$ (113.8 μL, 1.0 mol/L in toluene) at 0° C. After stirred at 0° C. for 9 h and then at room temperature for additional 15 h, the reaction was quenched with water (15 mL) and extracted with diethyl ether (3×15 mL). The organic layers were combined, dried over anhydrous sodium sulfate, and concentrated in vacuo to yield a crude product, which was purified by flash column chromatography on silica gel (ethyl acetate/hexane=1:4) to afford compound A26 (69 mg) in 65% yield. $^1$H NMR (600 MHz, $CCl_3D$) δ 5.85 (d, J=6.24 Hz, 1H), 5.72 (dd, J=1.65, 6.05 Hz, 1H), 5.65 (d, J=4.58 Hz, 1H), 5.39 (d, J=1.65 Hz, 1H), 4.70 (s, 1H), 3.59 (s, 3H), 3.30 (s, 3H), 2.82 (d, J=4.95 Hz, 3H), 2.41 (d, J=15.77 Hz, 1H), 2.20 (d, J=14.31 Hz, 1H), 1.99-2.09 (m, 1H), 1.75-1.89 (m, 2H), 1.68-1.73 (m, 1H), 1.66-1.68 (m, 1H), 1.62-1.66 (m, 2H), 1.54-1.59 (m, 1H), 1.53-1.54 (m, 1H), 1.50-1.53 (m, 1H), 1.47 (s, 3H), 1.43-1.46 (m, 1H), 1.38-1.42 (m, 1H), 1.34 (s, 3H), 1.19 (s, 3H), 1.17 (s, 3H), 1.07 (s, 3H), 0.91-0.98 (m, 1H), 0.59 (s, 3H); $^{13}$C NMR (151 MHz, $CCl_3D$) δ 179.1, 174.0, 158.7, 153.3, 143.7, 128.4, 116.5, 113.5, 89.1, 86.8, 52.5, 51.5, 44.3, 43.7, 40.4, 38.3, 37.2, 36.5, 34.7, 34.0, 33.5, 32.8, 31.5, 30.8, 30.6, 29.8, 29.4, 28.6, 27.3, 23.0, 19.5, 18.0; HRMS (ESI) m/z: calcd for $C_{32}H_{48}NO_5^+$ [M+H]$^+$: 526.3527, found: 526.3524.

Example 26

Preparation of benzyl (2R,4aS,6aS,9S,12bR,14aS, 14bR)-10-hydroxy-9-methoxy-2,4a,6a,9,12b,14a-hexamethyl-10-(methylamino)-11-oxo-1,2,3,4,4a,5, 6,6a,9,10,11,12b,13,14,14a,14b-hexadecahydropicene-2-carboxylate A27

A27

To a solution of compound A11 (50 mg, 0.088 mmol) in toluene (1 mL) were added $CH_3NH_2$ (12.4 μL, 0.088 mmol, 1 eq., 33% in absolutely ethanol) and TEA (88 mg, 122 μL, 10 eq.) at room temperature, followed by addition of $TiCl_4$ (16.6 μL, 1.0 mol/L in toluene) at 0° C. After stirred at 0° C. for 10 h, the reaction was quenched with water (10 mL) and extracted with ethyl acetate (3×10 mL). The organic layers were combined, dried over anhydrous sodium sulfate, and concentrated in vacuo to yield a crude product, which was purified by flash column chromatography on silica gel (ethyl acetate/hexane=1:4) to afford compound A27 (13 mg) in 25% yield. $^1$H NMR (600 MHz, $CCl_3D$) δ 7.31-7.36 (m, 4H), 7.28-7.31 (m, 1H), 5.83 (d, J=6.24 Hz, 1H), 5.71 (dd, J=1.65, 6.05 Hz, 1H), 5.64 (q, J=4.77 Hz, 1H), 5.32 (d, J=1.65 Hz, 1H), 5.11 (d, J=12.47 Hz, 1H), 4.93 (d, J=12.47 Hz, 1H), 4.73 (s, 1H), 3.31 (s, 3H), 2.86 (d, J=4.95 Hz, 3H),

115

2.44 (d, J=15.77 Hz, 1H), 2.25 (d, J=14.31 Hz, 1H), 2.06 (d, J=4.22 Hz, 1H), 1.81 (d, J=6.05 Hz, 1H), 1.68-1.72 (m, 1H), 1.64-1.68 (m, 1H), 1.60-1.64 (m, 1H), 1.52-1.56 (m, 1H), 1.51-1.52 (m, 1H), 1.48-1.51 (m, 1H), 1.47 (s, 3H), 1.45 (d, J=6.05 Hz, 1H), 1.41-1.44 (m, 1H), 1.39-1.41 (m, 1H), 1.36-1.39 (m, 1H), 1.30 (s, 3H), 1.21 (s, 3H), 1.17 (s, 3H), 1.07 (s, 3H), 0.95 (d, J=14.31 Hz, 1H), 0.56 (s, 3H); $^{13}$C NMR (151 MHz, CCl$_3$D) δ 178.2, 174.1, 158.7, 153.3, 143.6, 135.8, 128.5 (2C), 128.4, 128.2, 128.0 (2C), 116.5, 113.5, 89.1, 86.8, 66.1, 52.5, 44.3, 43.7, 40.5, 38.3, 37.2, 36.5, 34.5, 33.9, 33.1, 32.8, 31.5, 30.6, 30.6, 29.9, 29.2, 28.6, 27.4, 23.0, 19.5, 18.2; HRMS (ESI) m/z: calcd for C$_{38}$H$_{51}$NaNO$_5$$^+$ [M+Na]$^+$: 624.3659, found: 624.3658.

Example 27

Preparation of (2R,4aS,6aS,9S,12bR,14aS,14bR)-9-ethoxy-2,4a,6a,9,12b,14a-hexamethyl-10,11-dioxo-1,2,3,4,4a,5,6,6a,9,10,11,12b,13,14,14a,14b-hexa-decahydropicene-2-carboxylic acid A28

A28

To a solution of celastrol 1 (150 mg, 0.33 mmol) in ethanol (15 mL) was added EtONa (150 μL, 20% in EtOH). After stirred for 24 h, the reaction was quenched with 1 mol/L HCl (30 mL), the mixture was concentrated to remove the residual EtOH in vacuo, then extracted with ethyl acetate (3×20 mL), and washed by brine (3×15 mL). The organic layers were combined, dried over anhydrous sodium sulfate, and concentrated in vacuo to yield a crude product, which was purified by flash column chromatography on silica gel (ethyl acetate/hexane=1:6) to afford compound A28 (13 mg) in 13% yield. $^1$H NMR (600 MHz, CCl$_3$D) δ 6.51 (dd, J=1.10, 6.60 Hz, 1H), 6.43 (d, J=1.10 Hz, 1H), 6.12 (d, J=6.79 Hz, 1H), 3.59 (qd, J=7.00, 15.80 Hz, 1H), 3.33 (qd, J=7.20, 16.10 Hz, 1H), 2.40 (d, J=15.96 Hz, 1H), 2.12 (d, J=14.12 Hz, 1H), 1.98-2.02 (m, 2H), 1.79-1.85 (m, 3H), 1.68 (dd, J=7.89, 15.77 Hz, 2H), 1.62-1.64 (m, 1H), 1.53 (s, 3H), 1.47 (s, 3H), 1.31-1.38 (m, 3H), 1.28 (t, J=6.97 Hz, 4H), 1.22 (s, 3H), 1.16 (s, 3H), 1.07 (s, 3H), 0.95 (br. s., 1H), 0.68 (s, 3H); $^{13}$C NMR (151 MHz, CCl$_3$D) δ 196.3, 184.3, 182.0, 175.2, 163.1, 131.7, 127.2, 123.0, 116.3, 86.0, 61.5, 44.7, 43.9, 42.8, 40.2, 38.1, 36.2, 35.9, 34.5, 33.2, 32.6, 31.5, 30.7, 30.5, 29.4, 29.3, 28.5, 26.9, 22.5, 18.9, 15.6; HRMS (ESI) m/z: calcd for C$_{31}$H$_{41}$O$_5$$^-$ [M-H]$^-$: 493.2959, found: 493.2960.

116

Example 28

Preparation of (2R,4aS,6aS,9S,12bR,14aS,14bR)-10,11-dihydroxy-9-methoxy-2,4a,6a,9,12b,14a-hex-amethyl-1,2,3,4,4a,5,6,6a,9,10,11,12b,13,14,14a, 14b-hexadecahydropicene-2-carboxylic acid A29

A29

To a solution of compound A25 (102.5 mg, 0.18 mmol) in dioxane/water (6 mL, 1:1 (v/v)) was added KOH (101 mg, 1.8 mmol). After stirred at 100° C. for 4 h, the reaction was cooled down to room temperature, acidized with HCl (1 mol/L) to pH 2.0, and then extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:1) to afford compound A29 (49 mg) in 57% yield. $^1$H NMR (600 MHz, DMSO-d$_6$) δ 11.98 (br. s., 1H), 5.83 (d, J=6.42 Hz, 1H), 5.73 (d, J=6.05 Hz, 1H), 5.32 (br. s., 1H), 4.97 (d, J=5.87 Hz, 1H), 4.88 (d, J=4.95 Hz, 1H), 3.94 (t, J=6.60 Hz, 1H), 3.51 (dd, J=4.86, 7.52 Hz, 1H), 3.13 (s, 3H), 2.32 (d, J=15.59 Hz, 1H), 2.04 (d, J=13.75 Hz, 1H), 1.93-2.01 (m, 1H), 1.78-1.85 (m, 1H), 1.71-1.78 (m, 1H), 1.63-1.67 (m, 1H), 1.61-1.63 (m, 1H), 1.57-1.61 (m, J=7.90 Hz, 1H), 1.48-1.53 (m, 1H), 1.46-1.48 (m, 1H), 1.45-1.46 (m, 1H), 1.40-1.45 (m, 1H), 1.37 (d, J=15.41 Hz, 1H), 1.29 (dt, J=4.22, 13.66 Hz, 1H), 1.18 (s, 3H), 1.12 (s, 3H), 1.11 (br. s., 3H), 1.04 (br. s., 3H), 1.03 (br. s., 3H), 0.85 (d, J=12.65 Hz, 1H), 0.71 (s, 3H); $^{13}$C NMR (151 MHz, DMSO-d$_6$) δ 179.4, 154.0, 147.0, 133.2, 123.8, 116.0, 115.5, 79.0, 73.1, 72.9, 49.2, 43.6, 43.3, 39.4, 38.1, 37.0, 36.3, 35.0, 34.3, 32.9, 32.4, 31.3, 30.23, 30.21, 29.4, 29.1, 28.0, 23.2, 20.3, 18.7; HRMS (ESI) m/z: calcd for C$_{30}$H$_{43}$O$_5$$^-$ [M-H]$^-$: 483.3116, found: 483.3121.

Example 29

Preparation of (2R,4aS,6aS,9S,10Z,12bR,14aS, 14bR)-10-(cyanomethylidene)-9-methoxy-2,4a,6a,9, 12b,14a-hexamethyl-11-oxo-1,2,3,4,4a,5,6,6a,9,10, 11,12b,13,14,14a,14b-hexadecahydropicene-2-carboxylic acid A30

Example 30

Preparation of (2R,4aS,6aS,9S,10E,12bR,14aS, 14bR)-10-(cyanomethylidene)-9-methoxy-2,4a,6a,9, 12b,14a-hexamethyl-11-oxo-1,2,3,4,4a,5,6,6a,9,10, 11,12b,13,14,14a,14b-hexadecahydropicene-2-carboxylic acid A31

A30

A31

To a solution of compound A1 (100 mg, 0.21 mmol) and $K_2CO_3$ (172.5 mg, 1.25 mmol) in 5 mL THF was added diethyl cyanomethylphosphonate (60 mg, 50 μL, 0.34 mmol). After stirred at room temperature for 1.5 h, the reaction was quenched with brine (10 mL) and then extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:4) to afford compound A30 (62 mg) in 59% yield. $^1$H NMR (600 MHz, DMSO-d$_6$) δ 12.07 (br. s., 1H), 6.44 (dd, J=1.28, 6.60 Hz, 1H), 6.17 (d, J=6.60 Hz, 1H), 6.16 (s, 1H), 6.11 (d, J=1.28 Hz, 1H), 2.99 (s, 3H), 2.31 (d, J=15.59 Hz, 1H), 2.08 (d, J=11.55 Hz, 1H), 2.04 (d, J=16.14 Hz, 1H), 1.94-2.01 (m, 1H), 1.76-1.84 (m, 1H), 1.67-1.72 (m, 1H), 1.64 (d, J=8.25 Hz, 1H), 1.61-1.63 (m, J=3.30 Hz, 1H), 1.57-1.60 (m, 1H), 1.53-1.57 (m, 1H), 1.51-1.53 (m, 1H), 1.49-1.51 (m, 1H), 1.42 (s, 3H), 1.39-1.42 (m, 1H), 1.39 (s, 3H), 1.30 (dt, J=4.49, 13.80 Hz, 1H), 1.19 (s, 3H), 1.11 (s, 3H), 1.06 (s, 3H), 0.88 (d, J=11.92 Hz, 1H), 0.67 (s, 3H); $^{13}$C NMR (151 MHz, DMSO-d$_6$) δ 182.1, 179.4, 171.2, 161.5, 156.5, 129.0, 126.8, 120.1, 116.9, 115.9, 102.5, 80.8, 52.1, 44.1, 43.6, 41.7, 39.4, 37.9, 36.1, 35.7, 34.4, 32.8, 32.6, 32.4, 31.3, 30.19, 30.17, 29.4, 29.0, 28.0, 22.3, 18.3; HRMS (ESI) m/z: calcd for $C_{32}H_{40}NO_4^-$ [M−H]$^-$: 502.2963, found: 502.2969.

To a solution of A1 (230 mg, 0.51 mmol) and DBU (230 μL) in $CH_3CN$ (4 mL) was added diethyl cyanomethylphosphonate (92 μL). After stirred at room temperature for 1.5 h, the reaction was quenched with brine (15 mL) and then extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:4) to afford compound A30 (65 mg) in 27% yield and A31 (17 mg) in 7% yield. Compound A31: $^1$H NMR (600 MHz, DMSO-d$_6$) δ 12.04 (br. s., 1H), 6.69 (s, 1H), 6.49 (dd, J=6.6, 1.7 Hz, 1H), 6.19 (d, J=6.8 Hz, 1H), 6.17 (d, J=1.5 Hz, 1H), 3.03 (s, 3H), 2.32 (d, J=15.6 Hz, 1H), 2.03-2.09 (m, 2H), 1.95-2.01 (m, 1H), 1.77-1.84 (m, 1H), 1.68-1.72 (m, 1H), 1.60-1.66 (m, 3H), 1.54 (s, 3H), 1.51 (br. s., 1H), 1.40 (s, 3H), 1.27-1.33 (m, 2H), 1.23-1.27 (m, 2H), 1.20 (s, 3H), 1.12 (s, 3H), 1.06 (s, 3H), 0.89 (br. s., 1H), 0.68 (s, 3H); $^{13}$C NMR (151 MHz, DMSO-d$_6$) δ181.3, 179.4, 172.0, 161.8, 155.6, 128.7, 126.9, 119.8, 116.3, 116.0, 103.9, 79.9, 52.1, 44.2, 43.6, 41.9, 39.4, 37.8, 36.1, 35.6, 34.4, 32.7, 32.3, 31.8, 31.3, 30.2, 30.2, 29.4, 29.0, 28.0, 22.3, 18.4; HRMS (ESI) m/z: calcd for $C_{32}H_{42}NO_4^+$ [M+H]$^+$: 504.3108, found: 504.3105.

Example 31

Preparation of methyl (2R,4aS,6aS,12bR,14aS, 14bR)-9-hydroxy-2,4a,6a,9,12b,14a-hexamethyl-10, 11-dioxo-1,2,3,4,4a,5,6,6a,9,10,11,12b,13,14,14a, 14b-hexadecahydropicene-2-carboxylate A32; methyl (2R,4aS,6aS,10Z,12bR,14aS,14bR)-10-(cya-nomethylidene)-9-hydroxy-2,4a,6a,9,12b,14a-hex-amethyl-11-oxo-1,2,3,4,4a,5,6,6a,9,10,11,12b,13,14, 14a,14b-hexadecahydropicene-2-carboxylate A33; and methyl (2R,4aS,6aS,10E,12bR,14aS,14bR)-10-(cyanomethylidene)-9-hydroxy-2,4a,6a,9,12b,14a-hexamethyl-11-oxo-1,2,3,4,4a,5,6,6a,9,10,11,12b,13, 14,14a,14b-hexadecahydropicene-2-carboxylate A34

Scheme 8

Compounds A32, A33, and A34 were synthesized as shown in Scheme 8.

Compound A32. A solution of pristimerin 5 (1 g, 2.2 mmol) and phenylseleninyl benzeneseleninate (776 mg, 2.2 mmol) in dioxane (20 mL) was stirred at room temperature for 2 h. The reaction was then acidized with HCl (1 mol/L), extracted with ethyl acetate (3×20 mL), and washed by brine (20 mL). The organic layers were combined, dried over anhydrous sodium sulfate, and concentrated in vacuo to yield a crude product, which was purified by flash column chromatography on silica gel (ethyl acetate/hexane=1:4) to afford compound A32 (544 mg) in 53% yield.

Compounds A33 and A34. To a solution of compound A32 (80 mg, 0.166 mmol) and DBU (80 μL) in CH$_3$CN (3 mL) was added diethyl cyanomethylphosphonate (40 L). After stirred at room temperature for 1.5 h, the reaction was quenched with brine (15 mL) and then extracted with ethyl acetate (3×10 mL). The organic layers were combined, dried over anhydrous sodium sulfate, and concentrated in vacuo to yield a crude product, which was purified by flash column chromatography on silica gel (ethyl acetate/hexane=1:4) to afford compound A33 (16 mg) in 18% yield and compound A34 (12 mg) in 16% yield.

Compound A33: $^1$H NMR (600 MHz, DMSO-d$_6$) δ 6.62 (dd, J=1.10, 6.79 Hz, 1H), 6.14 (d, J=6.97 Hz, 1H), 6.06 (s, 1H), 6.05 (d, J=1.00 Hz, 1H), 6.01 (s, 1H), 3.51 (s, 3H), 2.31 (d, J=15.59 Hz, 1H), 2.06-2.10 (m, 1H), 2.02-2.06 (m, 1H), 1.95 (td, J=3.85, 12.10 Hz, 1H), 1.76-1.84 (m, J=14.10 Hz, 1H), 1.66 (dd, J=8.16, 15.86 Hz, 1H), 1.60-1.64 (m, 2H), 1.55-1.60 (m, J=5.30 Hz, 1H), 1.47-1.54 (m, 3H), 1.41-1.45 (m, J=3.30 Hz, 1H), 1.40 (s, 3H), 1.38 (s, 3H), 1.30-1.36 (m, 1H), 1.19 (s, 3H), 1.12 (s, 3H), 1.06 (s, 3H), 0.91 (d, J=13.75 Hz, 1H), 0.47 (s, 3H); $^{13}$C NMR (151 MHz, DMSO-d$_6$) δ 184.5, 177.9, 170.7, 162.5, 162.0, 134.5, 126.5, 120.0, 116.6 (2C), 97.5, 72.7, 51.5, 43.9, 43.6, 42.3, 39.8, 38.1, 37.3, 36.1, 34.4, 32.4, 32.3, 31.3, 30.2, 30.1, 30.0, 29.4, 29.1, 28.1, 22.3, 17.9; HRMS (ESI) m/z: calcd for C$_{32}$H$_{40}$NO$_4^-$ [M−H]$^-$: 502.2963, found: 502.2955.

Compound A34: $^1$H NMR (600 MHz, DMSO-d$_6$) δ 6.49 (dd, J=6.4, 1.3 Hz, 1H), 6.26 (s, 1H), 6.07 (d, J=6.4 Hz, 1H), 6.06 (s, 1H), 6.04 (s, 1H), 3.51 (s, 3H), 2.31 (d, J=15.8 Hz, 1H), 2.06 (d, J=14.1 Hz, 1H), 1.98-2.02 (m, 1H), 1.95 (td, J=14.0, 3.6 Hz, 1H), 1.79 (td, J=13.2, 6.4 Hz, 1H), 1.67 (dd, J=15.9, 8.0 Hz, 1H), 1.62 (br. s., 2H), 1.48-1.53 (m, 3H), 1.43-1.47 (m, 1H), 1.42 (d, J=3.3 Hz, 1H), 1.39 (s, 3H), 1.37 (s, 3H), 1.32-1.36 (m, 1H), 1.16 (s, 3H), 1.12 (s, 3H), 1.06 (s, 3H), 0.90 (d, J=14.3 Hz, 1H), 0.49 (s, 3H); $^{13}$C NMR (151 MHz, DMSO-d$_6$) δ 184.3, 177.9, 171.2, 163.4, 159.9, 134.6, 124.2, 120.3, 116.5, 115.7, 97.7, 74.8, 51.5, 44.1, 43.5, 41.0, 37.6, 36.0, 34.3, 33.9, 32.5, 32.2, 31.3, 30.3, 30.1, 29.4, 29.4, 29.1, 28.0, 22.1, 17.9 (one was buried in solvent peaks); HRMS (ESI) m/z: calcd for C$_{32}$H$_{40}$NO$_4^-$ [M−H]$^-$: 502.2963, found: 502.2961.

Example 32

Preparation of methyl (2R,4aS,6aS,12bR,14aS, 14bR)-9,10-dihydroxy-2,4a,6a,9,12b,14a-hexam-ethyl-11-oxo-1,2,3,4,4a,5,6,6a,9,10,11,12b,13,14, 14a,14b-hexadecahydropicene-2-carboxylate A35

A35

To a solution of compound A32 (50 mg, 0.104 mmol) in THF (1 mL) was added NaBH$_4$ (2 mg, 0.05 mmol). After stirred at −10° C. for 1 h, the reaction was quenched with HCl (1 mol/L, 10 mL), extracted with ethyl acetate (3×10 mL), and washed with brine (3×5 mL). The organic layers were combined, dried over anhydrous sodium sulfate, and concentrated in vacuo to yield a crude product, which was purified by flash column chromatography on silica gel (ethyl acetate/hexane=1:4) to afford compound A35 (28 mg) in 56% yield. $^1$H NMR (600 MHz, DMSO-d$_6$) δ 6.37 (dd, J=1.28, 6.60 Hz, 1H), 6.02 (d, J=6.60 Hz, 1H), 5.73 (d, J=1.30 Hz, 1H), 5.40 (d, J=4.22 Hz, 1H), 5.03 (s, 1H), 3.74 (d, J=3.67 Hz, 1H), 3.51 (s, 3H), 2.31 (d, J=15.59 Hz, 1H), 2.07 (d, J=13.75 Hz, 1H), 1.96-2.01 (m, 1H), 1.91-1.96 (m, 1H), 1.80 (dd, J=4.03, 9.54 Hz, 1H), 1.66 (dd, J=8.07, 15.77 Hz, 1H), 1.60-1.63 (m, J=7.50 Hz, 1H), 1.58-1.60 (m, 1H), 1.54-1.58 (m, 1H), 1.50-1.52 (m, 1H), 1.49-1.50 (m, 1H), 1.46-1.49 (m, 1H), 1.40-1.44 (m, 1H), 1.39 (dd, J=4.03, 7.34 Hz, 1H), 1.36 (s, 3H), 1.21 (s, 3H), 1.18 (s, 3H), 1.12 (s, 3H), 1.06 (s, 3H), 0.91 (d, J=13.57 Hz, 1H), 0.49 (s, 3H); $^{13}$C NMR (151 MHz, CDCl$_3$) δ 196.7, 178.8, 171.0, 162.4, 134.6, 127.5, 117.2, 116.6, 78.8, 74.4, 51.6, 44.2, 44.1, 42.9, 40.4, 39.2, 38.6, 36.4, 34.7, 33.1, 32.7, 31.6, 30.7, 30.5, 29.8, 29.6, 28.6, 23.7, 22.6, 18.1; HRMS (ESI) m/z: calcd for C$_{30}$H$_{43}$O$_5^+$ [M+H]$^+$: 483.3105, found: 483.3097.

Example 33

Preparation of (2R,4aS,6aS,9S,10E,12bR,14aS, 14bR)-10-(cyanomethylidene)-11-hydroxy-9-methoxy-2,4a,6a,9,12b,14a-hexamethyl-1,2,3,4,4a,5, 6,6a,9,10,11,12b,13,14,14a,14b-hexadecahydropicene-2-carboxylic acid A36

A36

To a solution of compound A30 (65 mg, 0.13 mmol) and CeCl$_3$·7H$_2$O (48 mg, 0.13 mmol) in THF (4 mL) at −10° C. was added NaBH$_4$ (5.9 mg, 0.15 mmol). After stirred at −10° C. for 1 h, the reaction was acidized with HCl (1 M) and then extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:3) to afford compound A36 (11 mg) in 16% yield. $^1$H NMR (600 MHz, DMSO-d$_6$) δ 12.01 (br. s., 1H), 5.87-5.90 (m, 1H), 5.85 (d, J=2.4 Hz, 1H), 5.84 (s, 1H), 5.62 (d, J=2.0 Hz, 1H), 5.44 (d, J=2.4 Hz, 1H), 4.97-4.99 (m, 1H), 3.21 (s, 3H), 2.33 (d, J=15.6 Hz, 1H), 2.04 (d, J=13.8 Hz, 1H), 1.94-2.01 (m, 1H), 1.79-1.84 (m, 1H), 1.76 (dt, J=13.3, 6.9 Hz, 1H), 1.64-1.70 (m, 2H), 1.61 (dd, J=15.8, 8.1

Hz, 1H), 1.50-1.55 (m, 1H), 1.42-1.48 (m, 3H), 1.37 (s, 3H), 1.27-1.32 (m, 2H), 1.23 (s, 3H), 1.13 (s, 3H), 1.11 (s, 3H), 1.04 (s, 3H), 0.86 (d, J=2.9 Hz, 1H), 0.72 (s, 3H); HRMS (ESI) m/z: calcd for $C_{32}H_{42}NO_4^-$ [M–H]$^-$: 504.3119, found: 504.3121.

Example 34

Preparation of methyl (2R,4aS,6aS,11E,12bR,14aS, 14bR)-11-(cyanomethylidene)-9-hydroxy-2,4a,6a,9, 12b,14a-hexamethyl-10-oxo-1,2,3,4,4a,5,6,6a,9,10, 11,12b,13,14,14a,14b-hexadecahydropicene-2-carboxylate A37

A37

Example 35

Preparation of (2R,4aS,6aS,9S,12bR,14aS,14bR)-10-(cyanomethyl)-9-methoxy-2,4a,6a,9,12b,14a-hexamethyl-11-oxo-1,2,3,4,4a,5,6,6a,9,10,11,12b,13, 14,14a,14b-hexadecahydropicene-2-carboxylic acid A38

A38

To a solution of compound A32 (100 mg, 0.21 mmol) and $K_2CO_3$ (187 mg, 1.35 mmol) in THF (4 mL) was added diethyl cyanomethylphosphonate (50 μL). After stirred at room temperature for 3.5 h, the reaction was quenched with brine (15 mL) and then extracted with ethyl acetate (3×10 mL). The organic layers were combined, dried over anhydrous sodium sulfate, and concentrated in vacuo to yield a crude product, which was purified by flash column chromatography on silica gel (ethyl acetate/hexane=1:4) to afford compound A37 (17 mg) in 16% yield. $^1$H NMR (600 MHz, DMSO-d$_6$) δ 6.70 (dd, J=1.56, 6.88 Hz, 1H), 6.31 (s, 1H), 6.24 (s, 1H), 6.20 (d, J=6.97 Hz, 1H), 6.09 (d, J=1.47 Hz, 1H), 3.49 (s, 3H), 2.30 (d, J=15.77 Hz, 1H), 2.02-2.11 (m, 2H), 1.95 (dt, J=3.94, 13.98 Hz, 1H), 1.81 (d, J=14.31 Hz, 1H), 1.65-1.69 (m, 1H), 1.60-1.65 (m, 2H), 1.55-1.60 (m, 1H), 1.48-1.54 (m, 3H), 1.44 (s, 3H), 1.40-1.43 (m, 1H), 1.39 (s, 3H), 1.32-1.38 (m, 1H), 1.21 (s, 3H), 1.11 (s, 3H), 1.06 (s, 3H), 0.91 (d, J=14.12 Hz, 1H), 0.46 (s, 3H); $^{13}$C NMR (151 MHz, CHLOROFORM-d) δ 183.7, 178.0, 171.5, 162.5, 160.8, 135.0, 127.4, 119.5, 117.0, 116.7, 100.5, 72.4, 51.5, 43.9, 43.7, 42.7, 39.9, 38.3, 38.2, 36.1, 34.4, 32.4, 32.3, 32.2, 31.4, 30.25, 30.17, 29.4, 29.2, 28.1, 22.3, 17.9; HRMS (ESI) m/z: calcd for $C_{32}H_{42}NO_4^+$ [M+H]$^+$: 504.3108, found: 504.3105.

To a solution of compound A30 (40 mg, 0.08 mmol) in THF (3 mL) at –10° C. was added NaBH$_4$ (2.8 mg, 0.08 mmol). After stirred at –10° C. for 1 h, the reaction was acidized with HCl (1 M) and then extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:4) to afford compound A38 (9 mg) in 23% yield. $^1$H NMR (600 MHz, DMSO-d$_6$) δ 11.87-12.25 (m, 1H), 6.52 (dd, J=6.7, 1.6 Hz, 1H), 6.06 (d, J=6.8 Hz, 1H), 5.84 (d, J=1.5 Hz, 1H), 3.09 (s, 3H), 2.99 (dd, J=7.7, 5.3 Hz, 1H), 2.62 (dd, J=17.4, 5.3 Hz, 1H), 2.43 (dd, J=17.3, 7.8 Hz, 1H), 2.31 (d, J=15.6 Hz, 1H), 2.04 (d, J=16.0 Hz, 1H), 1.95-2.01 (m, 2H), 1.76-1.82 (m, 1H), 1.59-1.66 (m, 2H), 1.50 (d, J=8.1 Hz, 2H), 1.40 (d, J=13.2 Hz, 1H), 1.37 (s, 3H), 1.36 (s, 3H), 1.26-1.32 (m, 2H), 1.25 (d, J=6.2 Hz, 2H), 1.18 (s, 3H), 1.11 (s, 3H), 1.06 (s, 3H), 0.87 (d, J=11.9 Hz, 1H), 0.68 (s, 3H); $^{13}$C NMR (151 MHz, CDCl$_3$) 3196.0, 179.5, 169.1, 160.6, 129.7, 126.8, 119.2, 118.5, 115.9, 76.7, 50.7, 49.6, 44.0, 43.7, 41.0, 40.0, 37.9, 36.3, 35.6, 34.4, 33.1, 32.4, 31.4, 30.4, 30.3, 29.5, 29.2, 28.1, 22.3, 21.0, 18.4, 14.3;

Example 36

Preparation of (2R,4aS,6aS,9S,12bR,14aS,14bR)-9-methoxy-2,4a,6a,9,12b,14a-hexamethyl-10,11-di-oxo-1,2,3,4,4a,5,6,6a,9,10,11,12b,13,14,14a,14b-hexadecahydropicene-2-carbonitrile A39

A39

Compound A39 was synthesized as shown in Scheme 9.

Scheme 9

6

$\xrightarrow{\text{MeONa}}{\text{MeOH}}$

A39

To a solution of compound 6 (50 mg, 0.11 mmol) in MeOH (3 mL) was added MeONa (48 μL, 30 wt % in methanol, ρ=0.97 g/mL). After stirred for 2.5 h in the presence of air, the reaction was quenched with 1N HCl (10 mL) and concentrated in vacuo. The resulting mixture was extracted with ethyl acetate (3×10 mL) and washed by brine (3×10 mL). The organic layers were combined, dried over anhydrous sodium sulfate, and concentrated in vacuo to yield a crude product, which was purified by prep-TLC (hexane/EtOAc=1:1) to afford compound A39 in 23% yield. $^{13}$C NMR (151 MHz, DMSO-d$_6$) δ 195.9, 181.5, 174.1, 161.9, 130.8, 126.9, 126.6, 122.8, 116.0, 86.2, 53.5, 44.0, 43.1, 42.3, 38.0, 35.9, 35.6, 34.6, 32.7, 32.6, 31.3, 31.3, 30.4, 30.1, 29.7, 29.2, 27.9, 26.4, 22.2, 21.2.

Example 37

Preparation of (4S,6bS,8aS,11R,12aR,12bS,14aR)-11-(aminomethyl)-4-methoxy-4,6b,8a,11,12b,14a-hexamethyl-4,6b,7,8,8a,9,10,11,12,12a,12b,13,14,14a-tetradecahydropicene-2,3-dione A40

A40

Compound A40 was synthesized as shown in Scheme 10.

Scheme 10

6

$\xrightarrow{\text{LiAlH}_4}$

7

$\xrightarrow{\text{MeONa}}{\text{MeOH}}$

-continued

A40

Scheme 11

8

A41

Compound 7. To a solution of compound 6 (50 mg, 0.12 mmol) in Et$_2$O (2 mL) was added a solution of LiAlH$_4$ in THF (850 µL, 0.85 mmol), which was diluted up to 2 mL with Et$_2$O at 0° C. After stirred at 40° C. overnight, the reaction was quenched with K$_2$CO$_3$ (sat.aq., 5 mL) and extracted with EtOAc (3×10 mL). The organic layers were combined, dried over anhydrous sodium sulfate, and concentrated in vacuo to yield a crude product, which was purified by prep-TLC (MeOH/DCM=1:10) to afford compound 7 (6 mg) in 12% yield. HRMS (ESI) m/z: calcd for C$_{29}$H$_{42}$NO$_2^+$ [M+H]$^+$: 436.3210, found: 436.3206.

To a solution of compound 7 (38.5 mg, 0.088 mmol) in MeOH (1 mL) was added MeONa (38 µL, 30 wt % in methanol, ρ=0.97 g/mL). After stirred for 2.5 h in the presence of air, the reaction was quenched with 1N HCl (10 mL) and concentrated in vacuo. The resulting mixture was extracted with ethyl acetate (3×10 mL) and washed by brine (3×10 mL). The organic layers were combined, dried over anhydrous sodium sulfate, and concentrated in vacuo to yield a crude product, which was purified by prep-TLC (CH$_2$Cl$_2$/MeOH=10:1) to afford compound A40 (2.13 mg) in 5.17%. LCMS (ESI) m/z: 466 [M+H]$^+$.

Example 38

Preparation of (4S,6bS,8aS,11R,12aR,12bS,14aR)-11-amino-4-methoxy-4,6b,8a,11,12b,14a-hexam-ethyl-4,6b,7,8,8a,9,10,11,12,12a,12b,13,14,14a-tetra-decahydropicene-2,3-dione A41

To a solution of compound 8 (42 mg, 0.1 mmol) in MeOH (1 mL) was added MeONa (45 µL, 30 wt % in methanol, ρ=0.97 g/mL). After stirred for 2.5 h in the presence of air, the reaction was quenched with 1N HCl (10 mL) and concentrated in vacuo. The resulting mixture was extracted with ethyl acetate (3×10 mL) and washed by brine (3×10 mL). The organic layers were combined, dried over anhydrous sodium sulfate, and concentrated in vacuo to yield a crude product, which was purified by prep-TLC(CH$_2$Cl$_2$/MeOH=10:1) to afford compound A41 (9 mg) in 20% yield. HRMS (ESI) m/z: calcd for C$_{29}$H$_{42}$NO$_3^+$ [M+H]$^+$: 452.3159, found: 452.3157.

Example 39

Preparation of 1-((2R,4aS,6aS,9S,12bR,14aS,14bR)-9-methoxy-2,4a,6a,9,12b,14a-hexamethyl-10,11-dioxo-1,2,3,4,4a,5,6,6a,9,10,11,12b,13,14,14a,14b-hexadecahydropicen-2-yl)urea A42

A41

A42

Compound A41 was synthesized as shown in Scheme 11.

Compound A42 was synthesized as shown in Scheme 12.

To a mixture of compound 9 (45 mg, 0.1 mmol) in MeOH (0.5 mL) was added $NH_3$ (aq. 34 mg). After stirred for 2 h at the room temperature, the reaction mixture was extracted with ethyl acetate (3×10 mL) and washed by brine (3×10 mL). The organic layers were combined, dried over anhydrous sodium sulfate, and concentrated in vacuo to yield a crude product, which was purified by prep-TLC ($CH_2Cl_2$/ MeOH=10:1) to afford compound 10 (13.6 mg) in 29% yield. LCMS (ESI) m/z: 465 [M+H]$^+$.

To a mixture of compound 10 (13.6 mg, 0.03 mmol) in MeOH (1 mL) was added MeONa (15 µL, 30 wt % in methanol, ρ=0.97 g/mL). After stirred for 2.5 h in the presence of air, the reaction was quenched with 1N HCl (10 mL) and the mixture was concentrated in vacuo. The resulting mixture was extracted with ethyl acetate (3×10 mL) and washed by brine (3×10 mL). The organic layers were combined, dried over anhydrous sodium sulfate, and concentrated in vacuo to yield a crude product, which was purified by prep-TLC($CH_2Cl_2$/MeOH=10:1) to afford compound A42 (5 mg) in 35% yield. LCMS (ESI) m/z: 495 [M+H]$^+$.

Scheme 12

9

10

A42

Example 40

Preparation of (6bS,8aS,11R,12aR,12bS,14aR)-16a-hydroxy-4a,6b,8a,11,12b,14a-hexamethyl-16-oxo-2,3,4a,6b,7,8,8a,9,10,11,12,12a,12b,13,14,14a,16,16a-octadecahydropiceno[3,4-b][1,4]dioxine-11-carboxylic acid A43

A43

Compound A43 was synthesized as shown in Scheme 13.

To a solution of celastrol 1 (100 mg, 0.2 mmol) in ethylene glycol (5 mL) was added NaH (60 wt % in oil, 145 mg, 30 eq.) at room temperature. After stirred at room temperature overnight, the reaction mixture was quenched by pure water, acidified with HCl (1 mol/L) to pH=2.0, and extracted with ethyl acetate (10 mL×3). The organic layers were combined, dried over anhydrous sodium sulfate, and concentrated in vacuo to yield a crude product, which was purified by flash column chromatography on silica gel (ethyl acetate/hexane=1:8) to yield compound A43 (19 mg) in 17% yield. $^1$H NMR (600 MHz, DMSO-d$_6$) δ 12.02 (br. s., 1H), 6.51 (dd, J=1.56, 6.88 Hz, 1H), 6.25 (s, 1H), 6.17 (d, J=6.97 Hz, 1H), 5.94 (d, J=1.47 Hz, 1H), 3.99 (dt, J=3.03, 11.23 Hz, 1H), 3.69 (dt, J=3.12, 11.37 Hz, 1H), 3.48-3.55 (m, 1H), 3.29-3.31 (m, 1H), 2.31 (d, J=15.77 Hz, 1H), 2.05-2.11 (m, 1H), 2.04 (d, J=15.04 Hz, 1H), 1.76-1.85 (m, 1H), 1.63-1.70 (m, 2H), 1.57-1.63 (m, 1H), 1.47-1.57 (m, 4H), 1.43 (s, 3H), 1.38-1.42 (m, 1H), 1.29-1.33 (m, 1H), 1.25-1.29 (m, 1H), 1.22 (s, 3H), 1.11 (s, 6H), 1.06 (s, 3H), 0.85-0.92 (m, 1H), 0.64 (s, 3H); HRMS (ESI) m/z: calcd for $C_{31}H_{43}O_6^+$ [M+H]$^+$: 511.3054, found: 511.3054.

Scheme 13

1

-continued

A43

Example 41

Preparation of (2R,4aS,6aS,9S,12bR,14aS,14bR)—N-(2-hydroxyethyl)-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A44

A44

Compound A44 was synthesized as shown in Scheme 14.

Scheme 14

A1

-continued

A44

To a solution of compound A1 (100 mg, 0.2 mmol) and PyBOP (237.4 mg, 0.44 mmol) in DMF (2 mL) was added DIPEA (322.5 mg, 75 μL, 0.44 mmol) at 0° C. After the solution was stirred for 30 min, $NH_2CH_2CH_2OH$ (153 mg, 1.2 mmol) was added. The reaction mixture was then warmed up to room temperature and stirred for 2 h. The reaction was quenched with brine (10 mL) and extracted with ethyl acetate (3×15 mL). The organic layers were combined, dried over anhydrous sodium sulfate, and concentrated in vacuo to yield a crude product, which was purified by flash column chromatography on silica gel (ethyl acetate/hexane=1:3) to afford compound A44 in 42% yield. $^1$H NMR (600 MHz, DMSO-$d_6$) δ 7.49 (t, J=5.41 Hz, 2H), 6.45 (d, J=6.60 Hz, 1H), 6.39 (s, 1H), 6.17 (d, J=6.79 Hz, 1H), 3.35-3.40 (m, 2H), 3.32 (t, J=6.60 Hz, 4H), 3.16 (s, 3H), 2.94-3.07 (m, 2H), 2.40 (d, J=15.77 Hz, 1H), 2.07 (d, J=11.74 Hz, 2H), 1.92-2.01 (m, 1H), 1.75-1.84 (m, 2H), 1.64 (dd, J=4.03, 13.02 Hz, 1H), 1.57-1.62 (m, 1H), 1.52-1.57 (m, 2H), 1.46-1.52 (m, 2H), 1.43 (s, 3H), 1.40 (s, 3H), 1.21-1.37 (m, 2H), 1.18 (s, 3H), 1.06 (s, 3H), 1.04 (s, 3H), 0.85 (d, J=13.57 Hz, 1H), 0.59 (s, 3H); $^{13}$C NMR (151 MHz, DMSO-$d_6$) δ 195.8, 181.5, 177.3, 174.2, 162.5, 130.6, 126.6, 122.6, 115.8, 86.2, 59.5, 53.5, 44.3, 43.8, 42.4, 41.9, 40.0, 37.7, 36.2, 35.3, 34.8, 33.4, 32.5, 31.4, 30.5, 30.2, 29.4, 28.8, 28.1, 26.5, 22.2, 17.8; HRMS (ESI) m/z: calcd for $C_{32}H_{44}NO_5^-$ [M–H]$^-$: 522.3225, found: 522.3221.

Compounds A45, A55, A56, and A57 were synthesized similarly.

(2R,4aS,6aS,9S,12bR,14aS,14bR)—N-Hydroxy-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A45. $^1$H NMR (600 MHz, DMSO-$d_6$) δ 10.47 (s, 1H), 8.35 (br. s., 1H), 6.48 (dd, J=0.92, 6.05 Hz, 1H), 6.41 (d, J=0.90 Hz, 1H), 6.18 (d, J=6.79 Hz, 1H), 3.15 (s, 3H), 2.37 (d, J=15.41 Hz, 1H), 2.06-2.13 (m, 1H), 2.04 (d, J=14.31 Hz, 1H), 1.94-2.01 (m, 1H), 1.74-1.84 (m, 2H), 1.63-1.71 (m, 1H), 1.60 (dd, J=3.58, 13.11 Hz, 1H), 1.50-1.58 (m, 3H), 1.47 (d, J=7.89 Hz, 1H), 1.44 (s, 3H), 1.41 (s, 3H), 1.23-1.35 (m, 2H), 1.19 (s, 3H), 1.05 (s, 6H), 0.78-0.87 (m, 1H), 0.63 (s, 3H); HRMS (ESI) m/z: calcd for $C_{30}H_{42}NO_5^+$ [M+H]$^+$: 496.3057, found: 496.3055.

(2R,4aS,6aS,9S,10R,12bR,14aS,14bR)-10-Hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxamide A55. $^1$H NMR (600 MHz, DMSO-$d_6$) δ 7.18 (s, 1H), 6.62 (s, 1H), 6.22 (dd, J=1.47, 6.42 Hz, 1H), 6.05 (d, J=6.60 Hz, 1H), 5.82 (d, J=1.65 Hz, 1H), 5.19 (d, J=4.58 Hz, 1H), 4.40 (d, J=4.40 Hz, 1H), 3.23 (s, 3H), 2.36 (d, J=15.59 Hz, 1H), 2.06 (d, J=14.12 Hz, 1H), 1.94-2.02 (m, 2H), 1.78 (d, J=8.44 Hz, 2H), 1.56-1.62 (m, 2H), 1.51-1.55 (m, 1H), 1.43-1.51 (m, 2H), 1.39 (dd, J=3.85, 9.72 Hz, 2H), 1.31 (s, 3H), 1.24-1.29 (m, 1H), 1.16 (s, 3H), 1.06 (s, 3H), 1.05 (s, 3H), 1.05 (br. s., 3H), 0.83-0.89 (m, 1H), 0.73 (s, 3H); $^{13}$C NMR (151 MHz, DMSO-$d_6$) δ 198.5, 179.8, 169.7, 159.3, 131.5, 123.8, 118.5, 115.6, 81.8, 74.7, 50.4, 43.9, 43.8, 40.4, 39.4, 37.6, 36.2, 34.9, 34.7, 33.3, 32.8, 31.4, 30.6, 30.2, 29.5, 28.7, 28.1, 22.5, 19.8, 18.2.

A45

A55

(3R,4S,6bS,8aS,11R,12aR,12bS,14aR)-3-hydroxy-4-methoxy-4,6b,8a,11,12b,14a-hexamethyl-11-(morpholine-4-carbonyl)-4,6b,7,8,8a,9,10,11,12,12a,12b,13,14,14a-tetra-decahydropicen-2(3H)-one A56. $^1$H NMR (600 MHz, DMSO-$d_6$) δ 6.22 (dd, J=1.47, 6.42 Hz, 1H), 6.06 (d, J=6.60 Hz, 1H), 5.87 (d, J=1.47 Hz, 1H), 5.21 (d, J=4.40 Hz, 1H), 4.43 (d, J=4.03 Hz, 1H), 3.54 (br. s., 5H), 3.23 (s, 3H), 2.34 (d, J=15.96 Hz, 1H), 2.17 (d, J=13.39 Hz, 1H), 1.97-2.04 (m, 2H), 1.75-1.81 (m, 1H), 1.69-1.75 (m, 1H), 1.59-1.69 (m, 3H), 1.48-1.53 (m, 3H), 1.38-1.41 (m, 1H), 1.33 (s, 3H), 1.24-1.28 (m, 1H), 1.20 (s, 3H), 1.17 (s, 3H), 1.09 (s, 3H), 1.07 (s, 3H), 0.84 (d, J=12.65 Hz, 1H), 0.54 (s, 3H); $^{13}$C NMR (151 MHz, DMSO-$d_6$) δ 198.6, 175.1, 169.6, 158.9, 131.6, 123.8, 118.8, 115.9, 81.9, 74.7, 50.4, 44.3, 43.8, 40.5, 40.0, 39.6, 37.8, 36.2, 35.5, 35.0, 34.1, 32.5, 31.7, 30.4, 30.1, 29.8, 29.7, 28.1, 22.9, 19.9, 18.3; LCMS (ESI) m/z: 552 [M+H]$^+$.

(2R,4aS,6aS,9S,10R,12bR,14aS,14bR)—N,10-dihydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxamide A57. LCMS (ESI) m/z: 498 [M+H]$^+$.

A56

A57

Example 42

Preparation of (2R,4aS,6aS,9S,14bR,16aS,16bR)-13a-hydroxy-9-methoxy-2,4a,6a,9,14b,16a-hexam-ethyl-2,3,4,4a,5,6,6a,9,11,12,13a,14b,15,16,16a,16b-hexadecahydro-1H-piceno[2,3-b][1,4]oxazine-2-carboxylic acid A46

A46

Compound A46 was synthesized as shown in Scheme 15.

Scheme 15

A1

A46

To a solution of compound A1 (200 mg, 0.42 mmol) in dry THF (2 mL) was added NH$_2$CH$_2$CH$_2$OH (1 mL). After stirred at room temperature for 6 h, the reaction mixture was filtered. The filter cake was washed with THF (2 mL) and ethyl acetate (10 mL×3) to afford compound A46 (112.5 mg) in 52% yield. $^1$H NMR (600 MHz, DMSO-d$_6$) δ 11.99 (br. s., 1H), 6.04-6.06 (m, 1H), 5.82 (d, J=6.60 Hz, 1H), 5.66 (s, 1H), 5.60 (s, 1H), 3.89 (dt, J=5.41, 10.77 Hz, 1H), 3.60-3.64 (m, 1H), 3.50-3.54 (m, 2H), 3.42 (s, 3H), 2.26 (d, J=15.59 Hz, 1H), 1.97 (d, J=13.57 Hz, 1H), 1.91 (dt, J=3.30, 13.85 Hz, 1H), 1.79-1.84 (m, 1H), 1.71 (ddd, J=8.34, 11.65, 14.12 Hz, 1H), 1.57-1.61 (m, 1H), 1.52-1.56 (m, 2H), 1.48 (dd, J=4.77, 12.29 Hz, 1H), 1.39-1.43 (m, 3H), 1.32 (d, J=14.31 Hz, 1H), 1.22-1.26 (m, 1H), 1.20 (s, 3H), 1.16 (s, 3H), 1.07 (s, 3H), 1.04 (s, 3H), 0.98 (s, 3H), 0.78-0.82 (m, 1H), 0.63 (s, 3H); $^{13}$C NMR (151 MHz, DMSO-d$_6$) δ 179.5, 165.2, 156.7, 156.0, 135.2, 120.2, 119.7, 115.7, 93.0, 79.8, 56.2, 53.3, 47.1, 43.6, 43.6, 39.5, 38.9, 37.3, 36.2, 34.5, 34.0, 32.7, 32.4, 31.4, 30.2, 30.2, 29.4, 29.1, 28.0, 22.8, 18.4, 17.9; HRMS (ESI) m/z: calcd for C$_{32}$H$_{46}$NO$_5$$^+$ [M+H]$^+$: 524.3371, found: 524.3366.

Compound A47 was synthesized similarly.

A47

(2R,4aS,6aS,9S,14bR,16aS,16bR)—N,13a-dihydroxy-9-methoxy-2,4a,6a,9,14b,16a-hexamethyl-2,3,4,4a,5,6,6a,9, 11,12,13a,14b,15,16,16a,16b-hexadecahydro-1H-piceno[2, 3-b][1,4]oxazine-2-carboxamide A47. $^1$H NMR (600 MHz, DMSO-d$_6$) δ 10.46 (s, 1H), 8.35 (br. s., 1H), 6.12 (dd, J=1.28, 6.42 Hz, 1H), 5.88 (d, J=6.60 Hz, 1H), 5.73 (s, 1H), 5.71 (s, 1H), 3.95 (dt, J=5.78, 10.59 Hz, 1H), 3.68 (dd, J=3.85, 10.27 Hz, 1H), 3.56-3.61 (m, 2H), 3.49 (s, 3H), 2.37 (d, J=15.59 Hz, 1H), 2.04 (d, J=15.41 Hz, 1H), 1.98-2.02 (m, 1H), 1.86 (d, J=10.82 Hz, 1H), 1.72-1.76 (m, 1H), 1.68 (dt, J=5.14, 13.48 Hz, 1H), 1.50-1.56 (m, 2H), 1.49 (d, J=4.77 Hz, 1H), 1.46-1.48 (m, 1H), 1.44-1.46 (m, 1H), 1.41-1.44 (m, 1H), 1.36-1.39 (m, 1H), 1.29-1.33 (m, 1H), 1.27 (s, 3H), 1.23 (s, 3H), 1.13 (s, 3H), 1.05 (br. s., 3H), 1.04 (br. s., 3H), 0.83 (d, J=13.39 Hz, 1H), 0.66 (s, 3H); $^{13}$C NMR (151 MHz, DMSO-d$_6$) δ 174.0, 165.2, 156.9, 156.4, 135.2, 120.2, 119.7, 115.6, 93.1, 79.9, 56.2, 53.3, 47.1, 43.8, 43.6, 38.9, 38.3, 37.2, 36.3, 34.7, 34.1, 33.4, 32.9, 31.4, 30.6, 30.3, 28.9, 28.8, 28.1, 22.7, 18.1, 17.9; LCMS (ESI) m/z: 539 [M+H]$^+$.

Example 43

Preparation of (2R,4aS,6aS,9S,12bR,14aS,14bR)-11-(hydroxyimino)-9-methoxy-2,4a,6a,9,12b,14a-hexamethyl-10-oxo-1,2,3,4,4a,5,6,6a,9,10,11,12b,13, 14,14a,14b-hexadecahydropicene-2-carboxylic acid A48

A48

Compound A48 was synthesized as shown in Scheme 16.

Scheme 16

A1

A48

To a solution of compound A1 (100 mg, 0.21 mmol) and NaH (30.3 mg, 1.26 mmol) in dry THF (5 mL) was added NH$_2$OH (50% in water, 138.7 mg). After stirred at room temperature overnight, the reaction mixture was quenched with 1N HCl (30 mL) and extracted with ethyl acetate (20 mL×3). The organic layers were combined, dried over anhydrous sodium sulfate, and concentrated in vacuo to yield a crude product, which was purified by flash column chromatography on silica gel (ethyl acetate/hexane=1:2) to afford compound A48 in 40% yield. HRMS (ESI) m/z: calcd for C$_{30}$H$_{42}$NO$_5$$^+$ [M+H]$^+$: 496.3057, found: 496.3052.

Compounds A49 and A50 were synthesized similarly.

(2R,4aS,6aS,9S,12bR,14aS,14bR)-10-(2-carbamoylhy-drazono)-9-methoxy-2,4a,6a,9,12b,14a-hexamethyl-11-oxo-1,2,3,4,4a,5,6,6a,9,10,11,12b,13,14,14a,14b-hexadeca-hydropicene-2-carboxylic acid A49. HRMS (ESI) m/z: calcd for C$_{31}$H$_{44}$N$_3$O$_5$$^+$ [M+H]$^+$: 538.3275, found: 538.3273.

(2R,4aS,6aS,9S,10S,12bR,14aS,14bR)-10-hydroxy-11-(hydroxyimino)-9-methoxy-2,4a,6a,9,12b,14a-hexamethyl-1,2,3,4,4a,5,6,6a,9,10,11,12b,13,14,14a,14b-hexadecahy-dropicene-2-carboxylic acid A50. $^1$H NMR (600 MHz, DMSO-d$_6$) δ 10.85 (br. s., 1H), 6.40 (s, 1H), 6.11 (d, J=6.24 Hz, 1H), 5.95 (d, J=6.60 Hz, 1H), 4.92 (br. s., 1H), 4.14 (s, 1H), 3.06 (s, 3H), 2.34 (d, J=15.41 Hz, 1H), 2.05 (d, J=13.02 Hz, 1H), 1.95-2.01 (m, 1H), 1.93 (d, J=12.10 Hz, 1H), 1.72-1.81 (m, 1H), 1.68 (d, J=10.64 Hz, 1H), 1.59-1.64 (m, 1H), 1.56-1.59 (m, 1H), 1.51-1.56 (m, 1H), 1.43-1.50 (m, 3H), 1.30-1.42 (m, 1H), 1.28 (s, 3H), 1.25-1.27 (m, 1H), 1.17 (s, 3H), 1.16 (br. s., 3H), 1.08 (s, 3H), 1.04 (s, 3H), 0.81-0.85 (m, 1H), 0.69 (s, 3H); $^{13}$C NMR (151 MHz, DMSO-d$_6$) δ 179.7, 157.5, 155.5, 153.6, 130.6, 121.9, 115.7, 108.4, 78.5, 70.5, 49.7, 43.7, 43.5, 40.1, 39.2, 37.5, 36.7, 36.3, 34.4, 33.4, 32.5, 31.4, 30.3, 30.3, 29.6, 29.2, 28.1, 22.8, 18.6, 18.3.

A49

A50

Example 44

Preparation of (2R,4aS,6aS,9S,12bR,14aS,14bR)-10-(acetamidoimino)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A51

A51

Compound A51 was synthesized as shown in Scheme 17.

Scheme 17

A1

+

A51

A52

A53

Example 44

Preparation of (4S,6bS,8aS,11R,12aR,12bS,14aR)-4-methoxy-4,6b,8a,11,12b,14a-hexamethyl-3-oxo-4,6b,7,8,8a,9,10,11,12,12a,12b,13,14,14a-tetradeca-hydro-3H-spiro[picene-2,2'-[1,3]dioxolane]-11-carboxylic acid A54

A54

Compound A54 was synthesized as shown in Scheme 18.

To a solution of compound A1 (200 mg, 0.42 mmol) in DMF (10 mL) was added acethydrazide (308.7 mg, 4.2 mmol) and MeONa (33% in methanol, 464 μL). After stirred at room temperature for 1 h, the reaction mixture was quenched with brine (15 mL) and extracted with ethyl acetate (15 mL×3). The organic layers were combined, washed with pure water (15 mL×3), dried over anhydrous sodium sulfate, and concentrated in vacuo to yield a crude product, which was purified by flash column chromatography on silica gel (ethyl acetate/hexane=1:1) to afford compound A51 (94.2 mg) in 42% yield. LCMS (ESI) m/z: 537 [M+H]$^+$.

Compounds A52 and A53 were synthesized similarly.

(2R,4aS,6aS,9S,12bR,14aS,14bR)-9-Methoxy-2,4a,6a,9,12b,14a-hexamethyl-11-oxo-10-{[(pyridin-4-yl)forma-mido]imino}-1,2,3,4,4a,5,6,6a,9,10,11,12b,13,14,14a,14b-hexadecahydropicene-2-carboxylic acid A52. LCMS (ESI) m/z: 600 [M+H]$^+$.

(2R,4aS,6aS,9S,12bR,14aS,14bR)-10-(2-benzoylhydra-zono)-9-methoxy-2,4a,6a,9,12b,14a-hexamethyl-11-oxo-1,2,3,4,4a,5,6,6a,9,10,11,12b,13,14,14a,14b-hexadecahy-dropicene-2-carboxylic acid A53.

Scheme 18

A1

1p;2p

PTSA
Toluene

A54

To a solution of compound A1 (200 mg, 0.42 mmol) in toluene (10 mL) was added p-toluenesulfonic acid (PTSA) (15.8 mg, 0.084 mmol) and ethylene glycol (258.4 mg, 4.2 mmol). After stirred at 85° C. for 3 h, the reaction mixture was quenched by brine (15 mL) and extracted with ethyl acetate (15 mL×3). The organic layers were combined, washed with pure water (15 mL×3), dried over anhydrous sodium sulfate, and concentrated in vacuo to yield a crude product, which was purified by flash column chromatography on silica gel (ethyl acetate/hexane: 1:4) to afford compound A54 (52.5 mg) in 24% yield. $^1$H NMR (600 MHz, DMSO-d$_6$) δ 12.02 (br. s., 1H), 6.02 (dd, J=1.56, 6.33 Hz, 1H), 5.94 (d, J=6.60 Hz, 1H), 5.47 (d, J=1.47 Hz, 1H), 4.01-4.16 (m, 3H), 3.88-3.96 (m, 1H), 3.15 (s, 3H), 2.33 (d, J=15.59 Hz, 1H), 2.04 (d, J=13.75 Hz, 1H), 1.94-2.01 (m, 1H), 1.89-1.94 (m, 1H), 1.73-1.81 (m, 1H), 1.64-1.71 (m, 2H), 1.59-1.64 (m, 1H), 1.52-1.57 (m, 1H), 1.45-1.50 (m, 3H), 1.44 (s, 3H), 1.38 (dd, J=2.38, 12.84 Hz, 1H), 1.31 (s, 3H), 1.26-1.30 (m, 1H), 1.15 (s, 3H), 1.11 (s, 3H), 1.05 (s, 3H), 0.85-0.89 (m, 1H), 0.70 (s, 3H); $^{13}$C NMR (151 MHz, DMSO-d$_6$) δ 203.9, 179.4, 156.6, 154.8, 130.1, 120.2, 119.1, 115.5, 101.0, 83.1, 66.3, 65.1, 52.9, 43.7, 43.5, 39.1, 37.0, 36.2, 34.3, 34.0, 32.6, 32.3, 31.3, 30.3, 30.2 (2C), 29.4, 29.0, 28.0, 27.0, 22.9, 18.6.

Example 45

Preparation of methyl (2R,4aS,6aS,14bR,16aS, 16bR)-9-methoxy-2,4a,6a,9,14b,16a-hexamethyl-11-oxo-1,3,4,4a,5,6,6a,9,9a,11,12,14b,15,16,16a,16b-hexadecahydro-2H-piceno[3,2-b][1,4]oxazine-2-carboxylate A58

A58

Compound A58 was synthesized as shown in Scheme 19.

A solution of compound A20 (150 mg, 0.3 mmol), Cbz-Gly-OH (75.3 mg, 0.33 mmol), and 4-DMAP (18.5 mg, 0.15 mmol) in THF (6 mL) was stirred at 0° C. for 15 min, followed by addition of DCC (93 mg, 0.45 mmol). After stirred at 0° C. for 1 h at room temperature for 16 h, the reaction mixture was quenched with brine (30 mL) and extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:8) to afford compound 8 (160.9 mg) in 77% yield. HRMS (ESI) m/z: calcd for C$_{31}$H$_{54}$NO$_6$$^+$ [M+H]$^+$: 688.3844, found: 688.3833.

A solution of compound 8 (70 mg, 0.1 mmol) in EtOH (4 mL) was hydrogenated at room temperature with hydrogen for 12 h in the presence of 10% Pd/C (0.5 eq., 5.5 mg, 0.05 mmol). The reaction mixture was then filtered. The filtrate was concentrated in vacuo to yield a crude product, which was purified by flash column chromatography on silica gel (ethyl acetate/hexane=1:8) to afford compound A58 (8.6 mg) in 16% yield. HRMS (ESI) m/z: calcd for C$_{33}$H$_{46}$NO$_5$$^+$ [M+H]$^+$: 536.3371, found: 536.3365.

Scheme 19

Z-GlyOH

A20

-continued

Pd/C, H₂

Scheme 20

A9

A59

Example 46

Preparation of (2R,4aS,6aS,9S,10Z,12bR,14aS, 14bR)-10-(cyanomethylidene)-9-methoxy-2,4a,6a,9, 12b,14a-hexamethyl-11-oxo-1,2,3,4,4a,5,6,6a,9,10, 11,12b,13,14,14a,14b-hexadecahydropicene-2-carboxamide A59

Compound A59 was synthesized as shown in Scheme 20.

To a mixture of compound A9 (100 mg, 0.21 mmol) and K₂CO₃ (172.5 mg, 1.25 mmol) in THF (5 mL) was added diethyl cyanomethylphosphonate (60 mg, 50 μL, 0.34 mmol). After stirred at room temperature for 1.5 h, the reaction mixture was quenched with brine (10 mL) and then extracted with ethyl acetate (3×20 mL). The organic layers were combined, dried over anhydrous sodium sulfate, and concentrated in vacuo to yield a crude product, which was purified by flash column chromatography on silica gel (ethyl acetate/hexane=1:4) to afford compound A59 (62 mg) in 42% yield. $^1$H NMR (600 MHz, DMSO-d$_6$) δ 7.18 (br. s., 1H), 6.62 (s, 1H), 6.44 (dd, J=1.28, 6.60 Hz, 1H), 6.16 (d, J=6.60 Hz, 1H), 6.15 (s, 1H), 6.11 (d, J=1.30 Hz, 1H), 2.99 (s, 3H), 2.37 (d, J=15.59 Hz, 1H), 2.03-2.10 (m, 2H), 1.98 (dt, J=3.67, 12.29 Hz, 1H), 1.75-1.84 (m, 2H), 1.59 (s, 2H), 1.53-1.58 (m, 2H), 1.49-1.53 (m, 2H), 1.47 (s, 1H), 1.42 (s, 3H), 1.38 (s, 3H), 1.25-1.28 (m, 1H), 1.18 (s, 3H), 1.05 (s, 6H), 0.83 (d, J=13.20 Hz, 1H), 0.72 (s, 3H); $^{13}$C NMR (151 MHz, DMSO-d$_6$) δ 182.1, 179.8, 171.4, 161.9, 156.6, 128.9, 126.9, 120.0, 116.9, 115.8, 102.4, 80.7, 52.1, 44.1, 43.8, 41.7, 39.4, 37.9, 36.2, 35.7, 34.7, 33.2, 32.9, 32.5, 31.4, 30.6, 30.2, 29.5, 28.8, 28.1, 22.3, 18.1.

Compounds A60 and A61 were synthesized similarly.

Benzyl (2R,4aS,6aS,9S,10Z,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A60. $^1$H NMR (600 MHz, DMSO-d$_6$) δ 7.32-7.35 (m, 4H), 7.25-7.29 (m, 4H), 6.72 (s, 1H), 6.47 (dd, J=1.56, 6.69 Hz, 1H), 6.15 (d, J=6.79 Hz, 1H), 6.09 (d, J=1.65 Hz, 1H), 5.07 (d, J=12.47 Hz, 1H), 4.92 (d, J=12.47 Hz, 1H), 3.04 (s, 3H), 2.33 (d, J=15.77 Hz, 1H), 2.10 (d, J=13.94 Hz, 1H), 1.93-1.99 (m, 1H), 1.87 (d, J=13.20 Hz, 1H), 1.76-1.83 (m, 1H), 1.69 (dd, J=8.07, 15.77 Hz, 1H), 1.56 (d, J=3.85 Hz, 1H), 1.54 (s, 3H), 1.46-1.52 (m, 3H), 1.37-1.43 (m, 3H), 1.35 (s, 3H), 1.22-1.27 (m, 1H), 1.16 (s, 6H), 1.06 (s, 3H), 0.91 (d, J=13.02 Hz, 1H), 0.43 (s, 3H); $^{13}$C NMR (151 MHz, DMSO-$d_6$) δ 182.5, 177.5, 171.6, 161.7, 157.1, 136.3, 129.5, 128.9 (2C), 128.6 (2C), 128.4, 127.1, 120.8, 117.4, 116.4, 102.9, 81.2, 66.1, 52.6, 44.5, 43.9, 42.0, 40.5, 40.3, 38.2, 36.5, 36.1, 34.6, 32.9, 32.8, 31.7, 30.6, 30.6, 29.9, 29.4, 28.4, 22.6, 18.6; HRMS (ESI) m/z: calcd for $C_{39}H_{48}NO_4^+$ [M+H]$^+$: 594.3578, found: 594.3575.

Benzyl (2R,4aS,6aS,9S,10E,12bR,14aS,14bR)-10-(cyanomethylidene)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A61. $^1$H NMR (600 MHz, DMSO-$d_6$) δ 7.32-7.38 (m, 4H), 7.29 (dt, J=2.57, 6.24 Hz, 1H), 6.42 (dd, J=1.65, 6.60 Hz, 1H), 6.17 (s, 1H), 6.13 (d, J=6.79 Hz, 1H), 6.04 (d, J=0.92 Hz, 1H), 5.06 (d, J=12.47 Hz, 1H), 4.93 (d, J=12.47 Hz, 1H), 3.01 (s, 3H), 2.34 (d, J=15.77 Hz, 1H), 2.11 (d, J=13.94 Hz, 1H), 1.96 (dt, J=3.85, 13.94 Hz, 1H), 1.85-1.91 (m, 1H), 1.75-1.83 (m, 1H), 1.66-1.74 (m, 1H), 1.52-1.58 (m, 2H), 1.45-1.51 (m, 3H), 1.42 (s, 3H), 1.36-1.41 (m, 3H), 1.35 (s, 3H), 1.16 (s, 3H), 1.16 (s, 3H), 1.06 (s, 3H), 0.91 (d, J=13.57 Hz, 1H), 0.44 (s, 3H); $^{13}$C NMR (151 MHz, DMSO-$d_6$) δ 182.1, 177.1, 171.1, 161.3, 156.6, 135.9, 129.0, 128.4 (2C), 128.1 (2C), 128.0, 126.6, 120.3, 116.9, 115.9, 102.5, 80.8, 65.6, 52.1, 44.0, 43.5, 41.5, 40.0, 39.8, 37.8, 36.0, 35.6, 34.1, 32.4, 32.3, 31.2, 30.2, 30.1, 29.4, 28.9, 27.9, 22.1, 18.1; HRMS (ESI) m/z: calcd for $C_{39}H_{48}NO_4^+$ [M+H]$^+$: 594.3578, found: 594.3576.

A60

A61

Example 47

Preparation of (2R,4aS,6aS,9S,10R,12bR,14aS, 14bR)-10-hydroxy-9-methoxy-2,4a,6a,9,12b,14a-hexamethyl-11-oxo-1,2,3,4,4a,5,6,6a,9,10,11,12b,13, 14,14a,14b-hexadecahydropicene-2-carbonitrile A62

A62

To a solution of compound A39 (15 mg, 0.03 mmol) in dry THF (2 mL) was added NaBH$_4$ (6.8 mg, 0.18 mmol). After stirred at 0° C. for 1.5 h, the reaction mixture was quenched with 1N HCl (5 mL) and extracted with ethyl acetate (5 mL×3). The organic layers were combined, dried over anhydrous sodium sulfate, and concentrated in vacuo to yield a crude product, which was purified by flash column chromatography on silica gel (ethyl acetate/hexane: 1:4) to afford compound A62 (3.2 mg) in 21% yield. LCMS (ESI) m/z: 464 [M+H]$^+$.

Example 48

Preparation of N-[(2R,4aS,6aS,9S,12bR,14aS, 14bR)-9-methoxy-2,4a,6a,9,12b,14a-hexamethyl-10, 11-dioxo-1,2,3,4,4a,5,6,6a,9,10,11,12b,13,14,14a, 14b-hexadecahydropicen-2-yl]acetamide A63

A63

Compound A63 was synthesized as shown in Scheme 21. To a solution of compound 8 (84 mg, 0.2 mmol) in MeCN (5 mL) was added 2,5-dioxopyrrolidin-1-yl acetate (124 mg, 0.8 mmol). After reaction completed, the reaction was quenched with 1N HCl (10 mL). The reaction mixture was extracted with ethyl acetate (3×10 mL) and washed by brine (3×10 mL). The organic layers were combined, dried over anhydrous sodium sulfate, and concentrated in vacuo to yield a crude product, which was purified by prep-TLC (CH$_2$Cl$_2$/MeOH=10:1) to afford compound 11 (22 mg) in 23.8% yield. LCMS (ESI) m/z: 464 [M+H]$^+$.

Scheme 21

8

11

A63

To a solution of compound 11 (23 mg, 0.05 mmol) in MeOH (1 mL) was added MeONa (25 μL, 30 wt % in methanol, ρ=0.97 g/mL). After stirred for 2.5 h in the presence of air, the reaction was quenched with 1N HCl (10 mL). The reaction mixture was concentrated in vacuo, extracted with ethyl acetate (3×10 mL), and washed by brine (3×10 mL). The organic layers were combined, dried over anhydrous sodium sulfate, and concentrated in vacuo to yield a crude product, which was purified by prep-TLC (CH$_2$Cl$_2$/MeOH=10:1) to afford compound A63 (6.5 mg) in 27.8% yield. LCMS (ESI) m/z: 494 [M+H]$^+$.

Example B1

Surface Plasmon Resonance (SPR)

A test compound was analyzed for its binding kinetics with Nur77-LBD at 25° C. on a BIAcore T200 machine with CM5 chips. PBSP was used for all measurements. For SPR measurements, Nur77-LBD proteins were purified. A blank channel was used as negative control. About 10,000 response units of Nur77-LBD were immobilized on the chips. When the data collection was finished in each cycle, the sensor surface was regenerated with glycine-HCl at pH 2.5. A serial of concentrations ranging from 0.15 to 5.0 μM of the test compound was used. Sensograms were fit globally with BIAcore T200 analysis using 1:1 Langmuir binding mode.

Surface plasma resonance (SPR) analysis revealed that compounds A1, A7, and A9 have K$_d$ of 390 nM, 560 nM, and 890 nM, respectively, when binding to the Nur77-LBD protein.

Example B2

Antiproliferative Activity in Cancerous Cells

The antiproliferative activity of a test compound was determined in cell lines: MDA-MB-231 (breast cancer), HepG2 (liver cancer), SW620 (colon cancer), A375 (malignant melanoma), A431 (epidermoid carcinoma), A549 (lung adenocarcinoma), and HeLa (ovarian cancer). MDA-MB-231, HepG2, SW480, SW620, A375, and A431 cells were cultured in Dulbecco's modified Eagle's medium (DMEM) containing 10% fetal bovine serum (FBS). HeLa cells were cultured in MEM/EBSS (MEM) containing 10% FBS. A549 cells were maintained in Kaighn's modification of Ham's F-12 medium containing 10% FBS. The colorimetric MTT (3-(4,5-dimethylthiazol-2-yl)-2,5-diphenyltetrazolium bromide) assay was used to measure the cell viability of different cells following treatment with the test compound.

Briefly cells were seeded in a 96 well plate at a density of 2,000-5,000 cells/well. Following attachment, the cells were treated with the test compound in media at various concentrations ranging from 0.137 to 100 μM or at a single concentration of 10 μM. After the cells were incubated at 37° C. for 48 or 72 h, MTT (20 μL, 5 mg/mL in PBS) was added to each well and the cells were incubated for another 4 h at 37° C. The supernatant was removed carefully and 150 μL of DMSO was added to each well to dissolve the MTT formazan crystals. The plate was shaken for 15-20 min and the absorbance value of each well was determined using a multi-well plate reader at 490 nm. The wells treated with DMSO were taken as a vehicle control. Data were also obtained similarly for all the replicates and the percentage viability was determined with respect to the DMSO-treated cells. The results are summarized in Table 1 below, wherein A represents no less than 80% inhibition of cell growth at 10 μM; B represents no less than 50% but less than 80% inhibition of cell growth at 10 μM; C represents no less than 30% but less than 50% inhibition of cell growth at 10 μM; and D represents less than 30% inhibition of cell growth at 10 μM.

TABLE 1

| | | | Inhibtion of Cancerous Cells | | | | |
|---|---|---|---|---|---|---|---|
| Cmpd. | MDA-MB-231 | HELA | SW620 | A549 | A431 | A375 | HepG2 |
| A1 | B | A | B | C | B | C | B |
| A2 | B | A | C | C | B | C | B |
| A3 | D | B | D | B | A | D | D |
| A4 | C | A | B | B | A | B | B |
| A5 | A | A | B | C | A | B | A |
| A6 | B | A | B | B | B | C | A |
| A7 | A | A | C | C | B | B | B |
| A8 | B | B | B | B | A | C | A |
| A9 | A | A | B | C | B | C | B |
| A10 | A | A | B | C | B | C | B |
| A11 | A | A | A | D | D | B | A |
| A12 | B | A | B | A | A | C | A |
| A13 | A | A | A | A | A | C | A |
| A14 | D | C | D | D | D | D | D |
| A15 | A | B | C | D | B | B | C |
| A16 | A | A | A | A | A | B | A |
| A17 | A | B | A | C | A | B | A |
| A18 | A | A | A | C | A | B | A |
| A19 | B | A | B | B | A | C | B |
| A20 | A | A | A | A | A | B | A |
| A21 | D | D | D | D | D | D | D |
| A23 | A | A | A | A | A | B | A |
| A25 | D | D | D | D | D | D | D |
| A26 | C | C | C | D | C | C | C |
| A28 | B | A | C | C | B | C | B |
| A29 | D | B | D | D | D | D | D |
| A30 | A | A | A | C | A | B | A |
| A31 | A | A | A | B | B | B | B |
| A32 | A | A | A | A | A | B | A |
| A33 | A | A | A | C | B | B | A |
| A34 | A | A | A | B | B | B | A |
| A35 | A | A | A | A | A | B | A |
| A36 | B | A | C | D | B | B | C |
| A37 | A | A | B | D | A | C | C |
| A38 | C | A | B | D | C | C | D |
| A43 | D | D | D | D | D | D | D |
| A44 | A | A | B | A | A | C | A |
| A45 | A | A | B | A | A | B | A |
| A46 | B | A | B | B | A | C | A |
| A47 | A | A | B | A | A | C | A |
| A50 | D | D | D | D | D | D | D |
| A51 | D | D | D | D | D | D | D |
| A52 | D | D | D | D | D | D | D |
| A54 | D | D | D | D | D | D | D |
| A55 | B | B | A | B | A | C | A |
| A56 | B | B | A | A | A | C | A |
| A57 | B | B | A | A | A | C | A |
| A59 | A | A | A | A | A | A | A |
| A62 | C | D | A | C | A | C | C |

Example B3

Antiproliferative Activity in MMTV-PyMT
Transgenic Mouse Model

To assess the antitumor effect in vivo, an MMTV-PyMT transgenic mouse model of spontaneous breast tumors was used. Female MMTV-PyMT mice of 12-week old were randomly divided into three groups (n=4). Each group was treated by oral administration for two weeks with vehicle (control), or compound A1 or A7 (20 mg/kg, daily). The mice were then sacrificed and tumor tissues were removed, weighted, and analyzed by Graphpad (*P<0.05, student's t test). The results are shown in FIG. 1.

Example B4

Antiproliferative Activity in B16F10 Xenograft
Mouse Model

Figure 2:
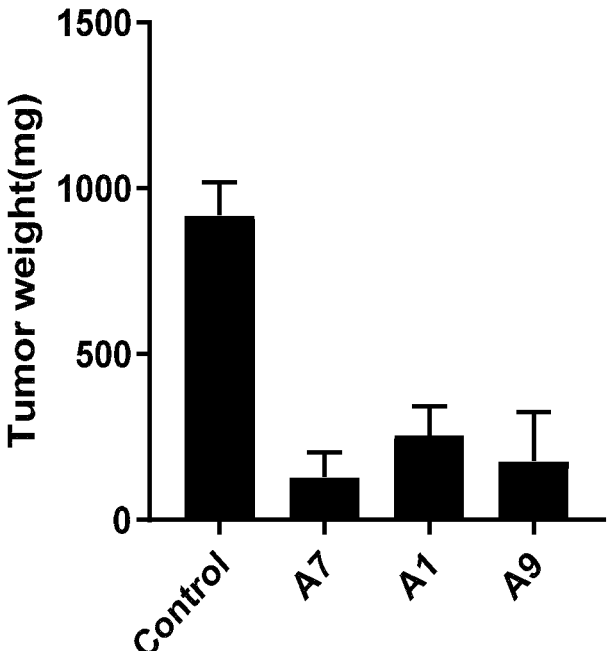
FIG. 2 shows the antiproliferative activity of compounds A1, A7, and A9 in a B16F10 transgenic mouse model of subcutaneous melanoma tumors.

To assess the anti-tumor effect in vivo, a B16F10 xenograft mouse model of subcutaneous melanoma tumors was used. After 3 days of tumor cell injection, mice were randomly divided into four groups (n=2-3). Each group was treated by oral administration for two weeks with vehicle (control), or compound A1, A7, or A9 (20 mg/kg, daily). The mice were then sacrificed and tumor tissues were removed, weighted, and analyzed by Graphpad (*P<0.05, student's t test). The results are shown in FIG. 2.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (I):

(I)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein:

$R^1$ is (i) —C(O)NR$^{1b}$R$^{1c}$, —C(R$^{1a}$)=NR$^{1b}$, —C(R$^{1a}$)=NOR$^{1b}$, —C(O)R$^{1a}$, —C(O)OR$^{1a}$, —C(O)ONR$^{1b}$R$^{1c}$, —C(O)OP(OR$^{1a}$)(OR$^{1b}$), —C(O)N(CN)R$^{1b}$, —C(O)N(R$^{1b}$)OR$^{1c}$, —C(O)SR$^{1a}$, —C(=NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS(O)$_2$R$^{1a}$, —OS(O)$_2$OR$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)SR$^{1d}$, —NR$^{1a}$C(O)NR$^{1b}$R$^{1c}$, —NR$^{1a}$C(=NR$^{1d}$)R$^{1b}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)N$^{1a}$R$^{1b}$R$^{1c}$, —NR$^{1a}$S(O)$_2$NR$^{1b}$R$^{1c}$, —SR$^{1a}$, —SC(O)R$^{1a}$, —SC(O)NR$^{1b}$R$^{1c}$, —S(O)R$^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$;

(ii) hydrogen, deuterium, azido, cyano, halo, isocyanato, isothiocyanato, or nitro; or (iii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl;

$R^2$ is —O—C$_{1-6}$ alkyl, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OP(O)(OR$^{1a}$)OR$^{1d}$, —OS(O)R$^{1a}$, —OS $(O)_2R^{1a}$, $-OS(O)_2OR^{1a}$, $-OS(O)NR^{1b}R^{1c}$, $-OS$ $(O)_2 NR^{1b}R^{1c}$, or heteroaryl; or $R^2$ and $R^3$ together with the carbon atoms to which they are attached form monocyclic heterocyclylene;

$R^3$ and $R^4$ together with the carbon atom to which they are attached form $=CO$, $=CR^{1a}R^{1c}$, $=CR^{1a}CN$, $=NR^{1b}$, $=NOR^{1b}$, $=NNR^{1a}C(O)R^{1d}$, $-NNR^{1a}C(O)NR^{1b}R^{1c}$, or heterocyclylene; or $R^3$ is $C_{1-6}$ alkyl, $-OR^{1a}$, $-OC$ $(O)R^{1a}$, $-OC(O)OR^{1a}$, $-OC(O)NR^{1b}R^{1c}$, $-OC(O)$ $SR^{1a}$, $-OC(=NR^{1a})NR^{1b}R^{1c}$, $-OC(S)R^{1a}$, $-OC(S)$ $OR^{1a}$, $-OC(S)NR^{1b}R^{1c}$, $-OP(O)(OR^{1a})OR^{1d}$, $-OS$ $(O)R^{1a}$, $-OS(O)_2R^{1a}$, $-OS(O)_2OR^{1a}$, $-OS(O)$ $NR^{1b}R^{1c}$, $-OS(O)_2NR^{1b}R^{1c}$, $-NR^{1b}R^{1c}$, $-NR^{1a}C$ $(O)R^{1d}$, $-NR^{1a}C(O)OR^{1d}$, $-NR^{1a}C(O)SR^{1d}$, $-NR^{1a}C(O)NR^{1b}R^{1c}$, $-NR^{1a}C(=NR^{1d})R^{1b}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)$ $R^{1d}$, $-NR^{1a}S(O)_2R^{1d}$, $-NR^{1a}S(O)NR^{1b}R^{1c}$, or $-NR^{1a}S(O)_2NR^{1b}R^{1c}$; and $R^4$ is hydrogen or $R^3$; or $R^3$, $R^4$, and $R^5$ together with the carbon atoms to which they are attached form unsaturated heterocyclylene; or $R^3$, $R^5$, and $R^6$ together with the carbon atoms to which they are attached form unsaturated heterocyclylene;

$R^5$ and $R^6$ together with the carbon atom to which they are attached form $=CO$, $=CR^{1a}R^{1c}$, $=CR^{1a}CN$, $=NR^{1b}$, $=NOR^{1b}$, or heterocyclylene; or $R^5$ is $C_{1-6}$ alkyl, $-OR^{1a}$, $-OC(O)R^{1a}$, $-OC(O)OR^{1a}$, $-OC(O)$ $NR^{1b}R^{1c}$, $-OC(O)SR^{1a}$, $-OC(=NR^{1a})NR^{1b}R^{1c}$, $-OC(S)R^{1a}$, $-OC(S)OR^{1a}$, $-OC(S)NR^{1b}R^{1c}$, $-OP$ $(O)(OR^{1a})OR^{1d}$, $-OS(O)R^{1a}$, $-OS(O)_2R^{1a}$, $-OS$ $(O)_2OR^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)SR^{1d}$, $-NR^{1a}C(O)NR^{1b}R^{1c}$, $-NR^{1a}C(=NR^{1d})R^{1b}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)R^{1d}$, $-NR^{1a}S(O)_2R^{1d}$, $-NR^{1a}S(O)$ $NR^{1b}R^{1c}$, or $-NR^{1a}S(O)_2NR^{1b}R^{1c}$; and $R^6$ is hydrogen or $R^5$; and each $R^{1a}$, $R^{1b}$, $R^{1c}$, and $R^{1d}$ is independently $C_{1-6}$ alkyl, hydrogen, deuterium, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, heterocyclyl, and heterocyclylene is optionally substituted with one or more substituents Q, where each Q is independently selected from (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more substituents $Q^a$; and (c) $-C(O)R^a$, $-C(O)OR^a$, $-C(O)NR^{1b}R^{1c}$, $-C(O)SR^a$, $-C(NR^a)NR^bR^c$, $-C(S)R^a$, $-C(S)OR^a$, $-C(S)NR^bR^c$, $-OR^a$, $-OC(O)R^a$, $-OC(O)OR^a$, $-OC(O)NR^bR^c$, $-OC(O)SR$, $-OC(=NR^a)NR^bR^c$, $-OC(S)R^a$, $-OC(S)OR^a$, $-OC(S)NR^bR^c$, $-OPO_3R^aR^d$, $-OS$ $(O)R^a$, $-OS(O)_2R^a$, $-OSO_3R^a$, $-OS(O)NR^bR^c$, $-OS(O)_2NR^bR^c$, $-NR^bR^c$, $-NR^aC(O)R^d$, $-NR^aC$ $(O)OR^d$, $-NR^aC(O)NR^bR^c$, $-NR^aC(O)SR^d$, $-NR^aC(=NR^d)NR^bR^c$, $-NR^aC(S)R^d$, $-NR^aC(S)$ $OR^d$, $-NR^aC(S)NR^bR^c$, $-NR^aS(O)R^d$, $-NR^aS(O)_2$ $R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2$ $NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents $Q^a$; or (iii) $R^b$ and $R^c$ together with the N atom to which they are attached form heterocyclyl, optionally substituted with one or more substituents $Q^a$;

wherein each $Q^a$ is independently selected from: (a) deuterium, azido, cyano, halo, isocyanato, isothiocyanato, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $-C(O)R^e$, $-C(O)$ $OR^e$, $-C(O)NR^fR^g$, $-C(O)SR^e$, $-C(NR^e)NR^fR^g$, $-C(S)R^e$, $-C(S)OR^e$, $-C(S)NR^fR^g$, $-OR^e$, $-OC$ $(O)R^e$, $-OC(O)OR^e$, $-OC(O)NR^fR^g$, $-OC(O)SR^e$, $-OC(=NR^e)NR^fR^g$, $-OC(S)R^e$, $-OC(S)OR^e$, $-OC(S)NR^fR^g$, $-OS(O)R^e$, $-OS(O)_2R^e$, $-OS(O)$ $NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(O)SR^f$, $-NR^eC(=NR^h)NR^fR^g$, $-NR^eC(S)R^h$, $-NR^eC(S)$ $OR^f$, $-NR^eC(S)NR^fR^g$, $-NR^eS(O)R^h$, $-NR^eS(O)_2$ $R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR$$^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R and $R^g$ together with the N atom to which they are attached form heterocyclyl.

2. The compound of claim 1, wherein the compound is a compound of Formula (V):

(V)

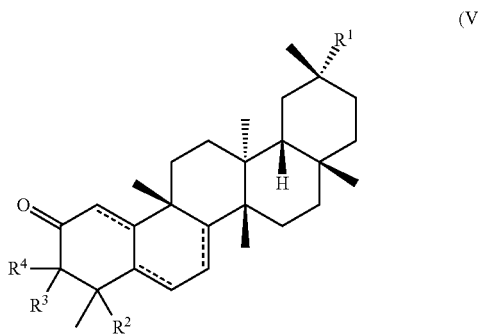

or a diastereomer, a mixture of two or more diastereomers, a tautomer, a mixture of two or more tautomers, or an isotopic variant thereof; or a pharmaceutically acceptable salt, solvate, hydrate, or prodrug thereof.

3. The compound of claim 1, wherein $R^3$ is $C_{1-6}$ alkyl, $-OR^{1a}$, $-OC(O)R^{1a}$, $-OC(O)OR^{1a}$, $-OC(O)ONR^{1b}R^{1c}$, $-OP(O)(OR^{1a})OR^{1d}$, or $-NR^{1b}R^{1c}$; and $R^4$ is hydrogen, $C_{1-6}$ alkyl, $-OR^1a$, $-OC(O)R^{1a}$, $-OC(O)OR^{1a}$, $-OC(O)$ $ONR^{1b}R^{1c}$, $-OP(O)(OR^{1a})OR^{1d}$, or $-NR^{1b}R^{1c}$; or $R^3$ and $R^4$ together with the carbon atom to which they are attached form heterocyclylene optionally substituted with one or more substituents Q, $=CR^{1a}R^{1c}$, $=CR^{1a}CN$, $=CO$, $=NR^{1b}$, or $=NOR^{1b}$.

4. The compound of claim 1, wherein $R^3$ is $-CH_2CN$, $-OH$, or $-OCOCH_2CH_2CH_3$; and $R^4$ is hydrogen, $-OH$, or $-OCOCH_2CH_2CH_3$; or $R^3$ and $R^4$ together with the carbon atom to which they are attached form $=CHCN$ or $=CO$.

5. The compound of claim 1, wherein the compound is a compound of Formula (IX):

(IX)

or a diastereomer, a mixture of two or more diastereomers, a tautomer, a mixture of two or more tautomers, or an isotopic variant thereof; or a pharmaceutically acceptable salt, solvate, hydrate, or prodrug thereof.

6. The compound of claim 1, wherein the compound is a compound of Formula (XIII):

(X)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein $R^{3a}$ is hydrogen, $C_{1-6}$ alkyl, —C(O)$R^{1a}$, —C(O)O$R^{1a}$, —C(O)ONR$^{1b}$R$^{1c}$, —C(O)S$R^{1a}$, —C(=NR$^{1a}$)NR$^{1b}$R$^{1c}$, —C(S)$R^{1a}$, —C(S)O$R^{1a}$, —C(S)NR$^{1b}$R$^{1c}$, —P(O)(OR$^{1a}$)OR$^{1d}$, —S(O)$R^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$; and wherein the alkyl is optionally substituted with one or more substituents Q.

7. The compound of claim 6, wherein $R^{3a}$ is hydrogen, $C_{1-6}$ alkyl, —C(O)$R^{1a}$, —C(O)O$R^{1a}$, —C(O)ONR$^{1b}$R$^{1c}$, or —P(O)(OR$^{1a}$)OR$^{1d}$.

8. The compound of claim 6, wherein $R^{3a}$ is hydrogen or —COCH$_2$CH$_2$CH$_3$.

9. The compound of claim 1, wherein the compound is a compound of Formula (XIX):

(XIX)

or a diastereomer, a mixture of two or more diastereomers, a tautomer, a mixture of two or more tautomers, or an isotopic variant thereof; or a pharmaceutically acceptable salt, solvate, hydrate, or prodrug thereof, wherein $R^{3a}$ and $R^{5a}$ are each independently hydrogen, $C_{1-6}$ alkyl, —C(O) $R^{1a}$, —C(O)O$R^{1a}$, —C(O)ONR$^{1b}$R$^{1c}$, —C(O)S$R^{1a}$, —C(=NR$^{1a}$)NR$^{1b}$R$^{1c}$, —C(S)$R^{1a}$, —C(S)O$R^{1a}$, —C(S) NR$^{1b}$R$^{1c}$, —P(O)(OR$^{1a}$)OR$^{1d}$, —S(O)$R^{1a}$, —S(O)$_2$R$^{1a}$, —S(O)$_2$OR$^{1a}$, —S(O)NR$^{1b}$R$^{1c}$, or —S(O)$_2$NR$^{1b}$R$^{1c}$; wherein the alkyl is optionally substituted with one or more substituents Q.

10. The compound of claim 1, wherein the compound is a compound of Formula (XXIII):

(XXIII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^{3b}$ is (i) hydrogen or deuterium; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q.

11. The compound of claim 10, wherein the compound is a compound of Formula (XXIIIa):

(XXIIIa)

or a diastereomer, a mixture of two or more diastereomers, a tautomer, a mixture of two or more tautomers, or an isotopic variant thereof; or a pharmaceutically acceptable salt, solvate, hydrate, or prodrug thereof.

12. The compound of claim 10, wherein the compound is a compound of Formula (XXIIIb):

(XXIIIb)

or a diastereomer, a mixture of two or more diastereomers, a tautomer, a mixture of two or more tautomers, or an isotopic variant thereof; or a pharmaceutically acceptable salt, solvate, hydrate, or prodrug thereof.

13. The compound of claim 10, wherein $R^{3b}$ is hydrogen, deuterium, or $C_{1-6}$ alkyl, optionally substituted with one or more substituents Q.

14. The compound of claim 10, wherein $R^{3b}$ is hydrogen or deuterium.

15. The compound of claim 1 wherein the compound is a compound of Formula (XXVII):

(XXVII)

or a diastereomer, a mixture of two or more diastereomers, a tautomer, a mixture of two or more tautomers, or an isotopic variant thereof; or a pharmaceutically acceptable salt, solvate, hydrate, or prodrug thereof.

16. The compound of claim 1, wherein the compound is a compound of Formula (XXIX):

(XXIX)

or a diastereomer, a mixture of two or more diastereomers, a tautomer, a mixture of two or more tautomers, or an isotopic variant thereof; or a pharmaceutically acceptable salt, solvate, hydrate, or prodrug thereof.

17. The compound of claim 1, wherein $R^6$ is —$OR^{1a}$.

18. The compound of claim 1, wherein $R^6$ is —OH.

19. The compound of claim 1, wherein $R^1$ is (i) hydrogen, azido, cyano, halo, isocyanato, isothiocyanato, or nitro; (ii) $C_{1-6}$ alkyl, $C_{2-6}$ alkenyl, or $C_{2-6}$ alkynyl, each of which is optionally substituted with one or more substituents Q; or (iii) —$C(R^{1a})$=$NR^{1b}$, —$C(R^{1a})$=$NOR^{1b}$, —$C(O)R^{1a}$, —$C(O)OR^{1a}$, —$C(O)N(R^{1b})CN$, —$C(O)NR^{1b}R^{1c}$, —$C(O)N(R^{1b})OR^{1c}$, —$C(=NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OC(S)NR^{1b}R^{1c}$, —$OP(O)(OR^{1a})OR^{1d}$, —$OS(O)_2R^{1a}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)SR^{1d}$, —$NR^{1a}C(O)NR^{1b}R^{1c}$, —$NR^{1a}C(=NR^{1d})R^{1b}$, —$NR^{1a}C(=NR^{1d})NR^{1b}R^{1c}$, —$NR^{1a}S(O)_2R^{1d}$, —$NR^{1a}S(O)_2NR^{1b}R^{1c}$, —$SR^{1a}$, —$SC(O)R^{1a}$, —$SC(O)NR^{1b}R^{1c}$, —$S(O)R^{1a}$, —$S(O)_2R^{1a}$, —$S(O)_2OR^{1a}$, or —$S(O)_2NR^{1b}R^{1c}$.

20. The compound of claim 1, wherein $R^1$ is (i) hydrogen, azido, cyano, isocyanato, isothiocyanato, or nitro; (ii) —$CH_2OH$, —$CH_2OPO(OH)_2$, —$CH_2NH_2$, morpholin-4-yl-methyl, piperazin-1-ylmethyl, or 4-methyl-piperazin-1-ylm-ethyl; (iii)

157 or (iv) —COH, —COOH, —C(O)OCH₃, —COOCH₂CH₃, 1,2,3-benzotriazol-1-yloxycarbonyl, benzyloxycarbonyl, pyrrolidin-1-ylcarbonyl, —CONH₂, —CONHCH₃, —CONHCH₂CH₃, —CONHCH₂CH₂CH₃, —CON(CH₃)₂, —CONHOH, —CONHCN, —OH, —OPO₃H₂, —NH₂, —NHC(O)NH₂, —NHSO₂NH₂, —SH, —SO₂H, or —SO₃H.

21. The compound of claim 1, wherein R² is indol-3-yl, —OCH₃, —OCD₃, —OCH₂CH₃, or —OCOCH₃.

22. A compound of:

(2R,4aS,6aS,9S,12bR,14aS,14bR)-9-methoxy-2,4a,6a,9, 12b,14a-hexamethyl-10,11-dioxo-1,2,3,4,4a,5,6,6a,9, 10,11,12b,13,14,14a,14b-hexadecahydropicene-2-carboxylic acid A1;

(2R,4aS,6aS,9S,12bR,14aS,14bR)-9-(methoxy-d₃)-2,4a, 6a,9,12b,14a-hexamethyl-10,11-dioxo-1,2,3,4,4a,5,6, 6a,9,10,11,12b,13,14,14a,14b-hexadecahydropicene-2-carboxylic acid A2;

(2R,4aS,6aS,12bR,14aS,14bR)-9-(acetyloxy)-2,4a,6a,9, 12b,14a-hexamethyl-10,11-dioxo-1,2,3,4,4a,5,6,6a,9, 10,11,12b,13,14,14a,14b-hexadecahydropicene-2-carboxylic acid A3;

methyl (2R,4aS,6aS,12bR,14aS,14bR)-9-(1H-indol-3-yl)-2,4a,6a,9,12b,14a-hexamethyl-10,11-dioxo-1,2,3, 4,4a,5,6,6a,9,10,11,12b,13,14,14a,14b-hexadecahydropicene-2-carboxylate A4;

methyl (2R,4aS,6aS,9S,12bR,14aS,14bR)-9-methoxy-2, 4a,6a,9,12b,14a-hexamethyl-10,11-dioxo-1,2,3,4,4a,5, 6,6a,9,10,11,12b,13,14,14a,14b-hexadecahydropicene-2-carboxylate A5;

1H-1,2,3-benzotriazol-1-yl (2R,4aS,6aS,9S,12bR,14aS, 14bR)-9-methoxy-2,4a,6a,9,12b,14a-hexamethyl-10, 11-dioxo-1,2,3,4,4a,5,6,6a,9,10,11,12b,13,14,14a,14b-hexadecahydropicene-2-carboxylate A6;

(2R,4aS,6aS,9S,12bR,14aS,14bR)-9-methoxy-N,2,4a,6a, 9,12b,14a-heptamethyl-10,11-dioxo-1,2,3,4,4a,5,6,6a, 9,10,11,12b,13,14,14a,14b-hexadecahydropicene-2-carboxamide A7;

(2R,4aS,6aS,9S,12bR,14aS,14bR)-9-methoxy-2,4a,6a,9, 12b,14a-hexamethyl-10,11-dioxo-1,2,3,4,4a,5,6,6a,9, 10,11,12b,13,14,14a,14b-hexadecahydropicene-2-carbonyl fluoride A8;

(2R,4aS,6aS,9S,12bR,14aS,14bR)-9-methoxy-2,4a,6a,9, 12b,14a-hexamethyl-10,11-dioxo-1,2,3,4,4a,5,6,6a,9, 10,11,12b,13,14,14a,14b-hexadecahydropicene-2-carboxamide A9;

(2R,4aS,6aS,9S,12bR,14aS,14bR)—N-ethyl-9-methoxy-2,4a,6a,9,12b,14a-hexamethyl-10,11-dioxo-1,2,3,4,4a, 5,6,6a,9,10,11,12b,13,14,14a,14b-hexadecahydropicene-2-carboxamide A10;

benzyl (2R,4aS,6aS,9S,12bR,14aS,14bR)-9-methoxy-2, 4a,6a,9,12b,14a-hexamethyl-10,11-dioxo-1,2,3,4,4a,5, 6,6a,9,10,11,12b,13,14,14a,14b-hexadecahydropicene-2-carboxylate A11;

(2R,4aS,6aS,9S,12bR,14aS,14bR)—N-propyl-9-methoxy-2,4a,6a,9,12b,14a-hexamethyl-10,11-dioxo-1,2,3,4,4a,5,6,6a,9,10,11,12b,13,14,14a,14b-hexadecahydropicene-2-carboxamide A12;

(2R,4aS,6aS,9S,12bR,14aS,14bR)-9-methoxy-N,N,2,4a, 6a,9,12b,14a-octamethyl-10,11-dioxo-1,2,3,4,4a,5,6, 6a,9,10,11,12b,13,14,14a,14b-hexadecahydropicene-2-carboxamide A13;

(4S,6bS,8aS,11R,12aR,12bS,14aR)-11-(hydroxymethyl)-4-methoxy-4,6b,8a,11,12b,14a-hexamethyl-4,6b,7,8, 8a,9,10,11,12,12a,12b,13,14,14a-tetradecahydropicene-2,3-dione A14;

(2R,4aS,6aS,9S,12bR,14aS,14bR)-9-ethoxy-2,4a,6a,9, 12b,14a-hexamethyl-10,11-dioxo-1,2,3,4,4a,5,6,6a,9, 10,11,12b,13,14,14a,14b-hexadecahydropicene-2-carboxylic acid A28;

(2R,4aS,6aS,9S,12bR,14aS,14bR)-9-methoxy-2,4a,6a,9, 12b,14a-hexamethyl-10,11-dioxo-1,2,3,4,4a,5,6,6a,9, 10,11,12b,13,14,14a,14b-hexadecahydropicene-2-carbonitrile A39;

(4S,6bS,8aS,11R,12aR,12bS,14aR)-11-(aminomethyl)-4-methoxy-4,6b,8a,11,12b,14a-hexamethyl-4,6b,7,8,8a, 9,10,11,12,12a,12b,13,14,14a-tetradecahydropicene-2, 3-dione A40;

(4S,6bS,8aS,11R,12aR,12bS,14aR)-11-amino-4-methoxy-4,6b,8a,11,12b,14a-hexamethyl-4,6b,7,8,8a, 9,10,11,12,12a,12b,13,14,14a-tetradecahydropicene-2, 3-dione A41;

1-((2R,4aS,6aS,9S,12bR,14aS,14bR)-9-methoxy-2,4a, 6a,9,12b,14a-hexamethyl-10,11-dioxo-1,2,3,4,4a,5,6, 6a,9,10,11,12b,13,14,14a,14b-hexadecahydropicen-2-yl)urea A42;

(2R,4aS,6aS,9S,10R,12bR,14aS,14bR)-10-hydroxy-9-methoxy-2,4a,6a,9,12b,14a-hexamethyl-11-oxo-1,2,3, 4,4a,5,6,6a,9,10,11,12b,13,14,14a,14b-hexadecahydropicene-2-carboxylic acid A15;

benzyl (2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A16;

(2R,4aS,6aS,9S,10R,12bR,14aS,14bR)-10-hydroxy-9-methoxy-N,2,4a,6a,9,12b,14a-heptamethyl-11-oxo-1, 2,3,4,4a,5,6,6a,9,10,11,12b,13,14,14a,14b-hexadecahydropicene-2-carboxamide A17;

(3R,4S,6bS,8aS,11R,12aR,12bS,14aR)-3-hydroxy-11-(hydroxymethyl)-4-methoxy-4,6b,8a,11,12b,14a-hexamethyl-2,3,4,4,6b,7,8,8a,9,10,11,12,12a,12b,13,14,14a-hexadecahydropicen-2-one A18;

(2R,4aS,6aS,9S,10R,12bR,14aS,14bR)-10-hydroxy-9-methoxy-2,4a,6a,9,12b,14a-hexamethyl-11-oxo-1,2,3, 4,4a,5,6,6a,9,10,11,12b,13,14,14a,14b-hexadecahydropicene-2-carbaldehyde A19;

methyl (2R,4aS,6aS,9S,10R,12bR,14aS,14bR)-10-hydroxy-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A20;

(2R,4aS,6aR,9S,10R,12bR,14aS,14bR)-10-hydroxy-9-methoxy-2,4a,6a,9,12b,14a-hexamethyl-11-oxo-1,2,3, 4,4a,5,6,6a,6b,7,8,8a,9,10,11,12b,13,14,14a,14b-icosahydropicene-2-carboxylic acid A21;

methyl (2R,4aS,6aR,9S,10R,12bR,14aS,14bR)-10-hydroxy-9-methoxy-2,4a,6a,9,12b,14a-hexamethyl-11-oxo-1,2,3,4,4a,5,6,6a,6b,7,8,8a,9,10,11,12b,13,14,14a, 14b-icosahydropicene-2-carboxylate A22;

(3R,4S,6bS,8aS,11R,12aR,12bS,14aR)-4-methoxy-4,6b, 8a,11,12b,14a-hexamethyl-11-(methylcarbamoyl)-2-oxo-2,3,4,6b,7,8,8a,9,10,11,12,12a,12b,13,14,14a-hexadecahydropicen-3-yl butyrate A23;

methyl (2R,4aS,6aS,9S,10R,12bR,14aS,14bR)-10-(butyryloxy)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylate A24;

methyl (2R,4aS,6aS,9S,12bR,14aS,14bR)-10-hydroxy-9-methoxy-2,4a,6a,9,12b,14a-hexamethyl-10-(methylamino)-11-oxo-1,2,3,4,4a,5,6,6a,9,10,11,12b,13,14, 14a,14b-hexadecahydropicene-2-carboxylate A26;

benzyl (2R,4aS,6aS,9S,12bR,14aS,14bR)-10-hydroxy-9-methoxy-2,4a,6a,9,12b,14a-hexamethyl-10-(methylamino)-11-oxo-1,2,3,4,4a,5,6,6a,9,10,11,12b,13,14, 14a,14b-hexadecahydropicene-2-carboxylate A27;

methyl (2R,4aS,6aS,12bR,14aS,14bR)-9,10-dihydroxy-2,4a,6a,9,12b,14a-hexamethyl-11-oxo-1,2,3,4,4a,5,6, 6a,9,10,11,12b,13,14,14a,14b-hexadecahydropicene-2-carboxylate A35;

methyl (2R,4aS,6aS,9S,10S,12bR,14aS,14bR)-10-(bu-tyryloxy)-11-hydroxy-9-methoxy-2,4a,6a,9,12b,14a-hexamethyl-1,2,3,4,4a,5,6,6a,9,10,11,12b,13,14,14a, 14b-hexadecahydropicene-2-carboxylate A25;

(2R,4aS,6aS,9S,12bR,14aS,14bR)-10,11-dihydroxy-9-methoxy-2,4a,6a,9,12b,14a-hexamethyl-1,2,3,4,4a,5,6, 6a,9,10,11,12b,13,14,14a,14b-hexadecahydropicene-2-carboxylic acid A29;

(2R,4aS,6aS,9S,10Z,12bR,14aS,14bR)-10-(cyanometh-ylidene)-9-methoxy-2,4a,6a,9,12b,14a-hexamethyl-11-oxo-1,2,3,4,4a,5,6,6a,9,10,11,12b,13,14,14a,14b-hexa-decahydropicene-2-carboxylic acid A30;

(2R,4aS,6aS,9S,10E,12bR,14aS,14bR)-10-(cyanometh-ylidene)-9-methoxy-2,4a,6a,9,12b,14a-hexamethyl-11-oxo-1,2,3,4,4a,5,6,6a,9,10,11,12b,13,14,14a,14b-hexa-decahydropicene-2-carboxylic acid A31;

methyl (2R,4aS,6aS,10Z,12bR,14aS,14bR)-10-(cyanom-ethylidene)-9-hydroxy-2,4a,6a,9,12b,14a-hexamethyl-11-oxo-1,2,3,4,4a,5,6,6a,9,10,11,12b,13,14,14a,14b-hexadecahydropicene-2-carboxylate A33;

methyl (2R,4aS,6aS,10E,12bR,14aS,14bR)-10-(cyanom-ethylidene)-9-hydroxy-2,4a,6a,9,12b,14a-hexamethyl-11-oxo-1,2,3,4,4a,5,6,6a,9,10,11,12b,13,14,14a,14b-hexadecahydropicene-2-carboxylate A34;

(2R,4aS,6aS,9S,10E,12bR,14aS,14bR)-10-(cyanometh-ylidene)-11-hydroxy-9-methoxy-2,4a,6a,9,12b,14a-hexamethyl-1,2,3,4,4a,5,6,6a,9,10,11,12b,13,14,14a, 14b-hexadecahydropicene-2-carboxylic acid A36;

methyl (2R,4aS,6aS,11E,12bR,14aS,14bR)-11-(cyanom-ethylidene)-9-hydroxy-2,4a,6a,9,12b,14a-hexamethyl-10-oxo-1,2,3,4,4a,5,6,6a,9,10,11,12b,13,14,14a,14b-hexadecahydropicene-2-carboxylate A37;

(2R,4aS,6aS,9S,12bR,14aS,14bR)-10-(cyanomethyl)-9-methoxy-2,4a,6a,9,12b,14a-hexamethyl-11-oxo-1,2,3, 4,4a,5,6,6a,9,10,11,12b,13,14,14a,14b-hexadecahy-dropicene-2-carboxylic acid A38;

(6bS,8aS,11R,12aR,12bS,14aR)-16a-hydroxy-4a,6b,8a, 11,12b,14a-hexamethyl-16-oxo-2,3,4a,6b,7,8,8a,9,10, 11,12,12a,12b,13,14,14a,16,16a-octadecahydropiceno[3,4-b][1,4]dioxine-11-carboxylic acid A43;

(2R,4aS,6aS,9S,12bR,14aS,14bR)—N-(2-hydroxyethyl)-9-methoxy-2,4a,6a,9,12b,14a-hexamethyl-10,11-di-oxo-1,2,3,4,4a,5,6,6a,9,10,11,12b,13,14,14a,14b-hexa-decahydropicene-2-carboxamide A44;

(2R,4aS,6aS,9S,12bR,14aS,14bR)—N-hydroxy-9-methoxy-2,4a,6a,9,12b,14a-hexamethyl-10,11-dioxo-1,2,3,4,4a,5,6,6a,9,10,11,12b,13,14,14a,14b-hexadeca-hydropicene-2-carboxamide A45;

(2R,4aS,6aS,14bR,16aS,16bR)-13a-hydroxy-9-methoxy-2,4a,6a,9,14b,16a-hexamethyl-2,3,4,4a,5,6,6a,9,11,12, 13a,14b,15,16,16a,16b-hexadecahydro-1H-piceno[2,3-b][1,4]oxazine-2-carboxylic acid A46;

(2R,4aS,6aS,14bR,16aS,16bR)—N,13a-dihydroxy-9-methoxy-2,4a,6a,9,14b,16a-hexamethyl-2,3,4,4a,5,6, 6a,9,11,12,13a,14b,15,16,16a,16b-hexadecahydro-1H-piceno[2,3-b][1,4]oxazine-2-carboxamide A47;

(2R,4aS,6aS,9S,12bR,14aS,14bR)-11-(hydroxyimino)-9-methoxy-2,4a,6a,9,12b,14a-hexamethyl-10-oxo-1,2,3, 4,4a,5,6,6a,9,10,11,12b,13,14,14a,14b-hexadecahy-dropicene-2-carboxylic acid A48;

(2R,4aS,6aS,9S,12bR,14aS,14bR)-10-(2-carbamoylhy-drazono)-9-methoxy-2,4a,6a,9,12b,14a-hexamethyl-11-oxo-1,2,3,4,4a,5,6,6a,9,10,11,12b,13,14,14a,14b-hexadecahydropicene-2-carboxylic acid A49;

(2R,4aS,6aS,9S,10S,12bR,14aS,14bR)-10-hydroxy-11-(hydroxyimino)-9-methoxy-2,4a,6a,9,12b,14a-hexam-ethyl-1,2,3,4,4a,5,6,6a,9,10,11,12b,13,14,14a,14b-hexadecahydropicene-2-carboxylic acid A50;

(2R,4aS,6aS,9S,12bR,14aS,14bR)-10-(acetamidoimino)-9-methoxy-2,4a,6a,9,12b,14a-hexamethyl-11-oxo-1,2, 3,4,4a,5,6,6a,9,10,11,12b,13,14,14a,14b-hexadecahy-dropicene-2-carboxylic acid A51;

(2R,4aS,6aS,9S,12bR,14aS,14bR)-9-methoxy-2,4a,6a,9, 12b,14a-hexamethyl-11-oxo-10-{[(pyridin-4-yl)for-mamido]imino}-1,2,3,4,4a,5,6,6a,9,10,11,12b,13, 14,14a,14b-hexadecahydropicene-2-carboxylic acid A52;

(2R,4aS,6aS,9S,12bR,14aS,14bR)-10-(2-benzoylhydra-zono)-9-methoxy-2,4a,6a,9,12b,14a-hexamethyl-11-oxo-1,2,3,4,4a,5,6,6a,9,10,11,12b,13,14,14a,14b-hexa-decahydropicene-2-carboxylic acid A53;

(4S,6bS,8aS,11R,12aR,12bS,14aR)-4-methoxy-4,6b,8a, 11,12b,14a-hexamethyl-3-oxo-4,6b,7,8,8a,9,10,11,12, 12a,12b,13,14,14a-tetradecahydro-3H-spiro[picene-2, 2'-[1,3]dioxolane]-11-carboxylic acid A54;

(2R,4aS,6aS,9S,10R,12bR,14aS,14bR)-10-hydroxy-9-methoxy-2,4a,6a,9,12b,14a-hexamethyl-11-oxo-1,2,3, 4,4a,5,6,6a,9,10,11,12b,13,14,14a,14b-hexadecahy-dropicene-2-carboxamide A55;

(3R,4S,6bS,8aS,11R,12aR,12bS,14aR)-3-hydroxy-4-methoxy-4,6b,8a,11,12b,14a-hexamethyl-11-(morpho-line-4-carbonyl)-4,6b,7,8,8a,9,10,11,12,12a,12b,13,14, 14a-tetradecahydropicen-2(3H)-one A56;

(2R,4aS,6aS,9S,10R,12bR,14aS,14bR)—N,10-dihy-droxy-9-methoxy-2,4a,6a,9,12b,14a-hexamethyl-11-oxo-1,2,3,4,4a,5,6,6a,9,10,11,12b,13,14,14a,14b-hexa-decahydropicene-2-carboxamide A57;

methyl (2R,4aS,6aS,14bR,16aS,16bR)-9-methoxy-2,4a, 6a,9,14b,16a-hexamethyl-11-oxo-1,3,4,4a,5,6,6a,9,9a, 11,12,14b,15,16,16a,16b-hexadecahydro-2H-piceno[3, 2-b][1,4]oxazine-2-carboxylate A58;

(2R,4aS,6aS,9S,10Z,12bR,14aS,14bR)-10-(cyanometh-ylidene)-9-methoxy-2,4a,6a,9,12b,14a-hexamethyl-11-oxo-1,2,3,4,4a,5,6,6a,9,10,11,12b,13,14,14a,14b-hexa-deca-hydropicene-2-carboxamide A59;

benzyl (2R,4aS,6aS,9S,10Z,12bR,14aS,14bR)-10-(cya-nomethylidene)-9-methoxy-2,4a,6a,9,12b,14a-hexam-ethyl-11-oxo-1,2,3,4,4a,5,6,6a,9,10,11,12b,13,14,14a, 14b-hexadeca-hydropicene-2-carboxylate A60;

benzyl (2R,4aS,6aS,9S,10E,12bR,14aS,14bR)-10-(cya-nomethylidene)-9-methoxy-2,4a,6a,9,12b,14a-hexam-ethyl-11-oxo-1,2,3,4,4a,5,6,6a,9,10,11,12b,13,14,14a, 14b-hexadecahydropicene-2-carboxylate A61;

(2R,4aS,6aS,9S,10R,12bR,14aS,14bR)-10-hydroxy-9-methoxy-2,4a,6a,9,12b,14a-hexamethyl-11-oxo-1,2,3, 4,4a,5,6,6a,9,10,11,12b,13,14,14a,14b-hexadecahy-dropicene-2-carbonitrile A62; or N-[(2R,4aS,6aS,9S,12bR,14aS,14bR)-9-methoxy-2,4a, 6a,9,12b,14a-hexamethyl-10,11-dioxo-1,2,3,4,4a,5,6, 6a,9,10,11,12b,13,14,14a,14b-hexadecahydropicen-2-yl]acetamide A63;

or a diastereomer, a mixture of diastereomers, a tautomer, a mixture of two or more tautomers, or an isotopic variant thereof; or a pharmaceutically acceptable salt, solvate, hydrate, or prodrug thereof.

23. A pharmaceutical composition comprising a com-pound of claim 1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

24. A method of treating, ameliorating, or preventing one or more symptoms of a disorder, disease, or condition mediated by nuclear receptor subfamily 4 group A member 1 in a subject, comprising administering to the subject a therapeutically effective amount of a compound of claim 1.

25. A method of treating, ameliorating, or preventing one or more symptoms of a proliferative disease in a subject, comprising administering to the subject a therapeutically effective amount of a compound of claim 1.

26. The compound of claim 1, wherein $R^2$ is heteroaryl, —O—$C_{1-6}$ alkyl, or —OCO—$C_{1-6}$ alkyl.

\* \* \* \* \*